US012663423B2

(12) United States Patent
Shainker et al.

(10) Patent No.: US 12,663,423 B2
(45) Date of Patent: Jun. 23, 2026

(54) BIOMARKERS FOR PLACENTA ACCRETA SPECTRUM (PAS) DISORDERS

(71) Applicant: Beth Israel Deaconess Medical Center, Inc., Boston, MA (US)

(72) Inventors: Scott Shainker, Boston, MA (US); Towia Libermann, Boston, MA (US); S. Ananth Karumanchi, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 947 days.

(21) Appl. No.: 17/794,581

(22) PCT Filed: Jan. 21, 2021

(86) PCT No.: PCT/US2021/014299
§ 371 (c)(1),
(2) Date: Jul. 21, 2022

(87) PCT Pub. No.: WO2021/150672
PCT Pub. Date: Jul. 29, 2021

(65) Prior Publication Data
US 2023/0118097 A1 Apr. 20, 2023

Related U.S. Application Data

(60) Provisional application No. 62/964,449, filed on Jan. 22, 2020.

(51) Int. Cl.
*G01N 33/68* (2006.01)
*C12Q 1/6883* (2018.01)

(52) U.S. Cl.
CPC ......... *G01N 33/689* (2013.01); *C12Q 1/6883* (2013.01); *C12Q 2600/118* (2013.01); *C12Q 2600/158* (2013.01)

(58) Field of Classification Search
CPC ............... G01N 33/689; C12Q 1/6883; C12Q 2600/118; C12Q 2600/158
See application file for complete search history.

(56) References Cited

U.S. PATENT DOCUMENTS 10,359,435 B2 7/2019 Nikrad et al.
2018/0148456 A1 5/2018 Clay et al.

OTHER PUBLICATIONS

Tseng JJ, Hsu SL, Ho ES, Hsieh YT, Wen MC, Chou MM. Differential expression of angiopoietin-1, angiopoietin-2, and Tie receptors in placentas from pregnancies complicated by placenta accreta. Am J Obstet Gynecol. Feb. 2006;194(2):564-71 (Year: 2006).*
Tseng JJ, Chou MM, Hsieh YT, Wen MC, Ho ES, Hsu SL. Differential expression of vascular endothelial growth factor, placenta growth factor and their receptors in placentae from pregnancies complicated by placenta accreta. Placenta. Jan. 2006;27(1):70-8 (Year: 2006).*

(Continued)

*Primary Examiner* — Bao-Thuy L Nguyen
*Assistant Examiner* — Christopher Evans
(74) *Attorney, Agent, or Firm* — Greenberg Traurig, LLP; Melissa Hunter-Ensor; Nicholas R. Ballor

(57) ABSTRACT

Methods and compositions for detecting or determining a subject's risk of developing placenta accreta spectrum (PAS) are provided. Biomarkers are described that can be useful in detecting PAS in the second or third trimester of pregnancy.

4 Claims, 22 Drawing Sheets

Specification includes a Sequence Listing.

(56)                References Cited

OTHER PUBLICATIONS

Tong, An MD; Zhao, Fumin MD; Liu, Ping MD; Zhao, Xia MD; Qi, Xiaorong MD,*. Management of postpartum pulmonary embolism combined with retained placenta accreta: A case report. Medicine 98(38):p. e17219, Sep. 2019. (Year: 2019).*

Gu Shengyi et al., "Research Progress on Factors Related to Placenta Accreta" J Int Obstet Gynecol , Aug. 2018 , vol. 45 , No. 4 (Year: 2018).*

Gu Shengyi et al., "Research Progress on Factors Related to Placenta Accreta" J Int Obstet Gynecol , Aug. 2018 , vol. 45 , No. 4 Machine Translation (Year: 2018).*

GenBank Accession No. AAA35623.1, downloaded Nov. 8, 2022 (1 page).

GenBank Accession No. AAA51796.1, downloaded Nov. 8, 2022 (1 page).

GenBank Accession No. AAH06161.1, downloaded Nov. 8, 2022 (2 pages).

GenBank Accession No. AAH08812.1, downloaded Nov. 8, 2022 (2 pages).

GenBank Accession No. AAH14277.1, downloaded Nov. 8, 2022 (2 pages).

GenBank Accession No. AAH19827.1, downloaded Nov. 8, 2022 (1 page).

GenBank Accession No. AAH31592.1, downloaded Nov. 8, 2022 (2 pages).

GenBank Accession No. AAH32489.1, downloaded Nov. 8, 2022 (2 pages).

GenBank Accession No. AAH36515.1, downloaded Nov. 8, 2022 (2 pages).

GenBank Accession No. AAH53550.1, downloaded Nov. 8, 2022 (2 pages).

GenBank Accession No. AAH69508.1, downloaded Nov. 8, 2022 (1 page).

GenBank Accession No. AAH69525.1, downloaded Nov. 8, 2022 (1 page).

GenBank Accession No. AAH93965.1, downloaded Nov. 8, 2022 (2 pages).

GenBank Accession No. AAI17257.1, downloaded Nov. 8, 2022 (2 pages).

GenBank Accession No. AAI51133.1, downloaded Nov. 8, 2022 (2 pages).

GenBank Accession No. AAK60338.1, downloaded Nov. 8, 2022 (1 page).

GenBank Accession No. AAN37387.1, downloaded Nov. 8, 2022 (1 page).

GenBank Accession No. AAQ01759.1, downloaded Nov. 8, 2022 (2 pages).

GenBank Accession No. AAV38570.1, downloaded Nov. 8, 2022 (1 page).

GenBank Accession No. AQY77246.1, downloaded Nov. 8, 2022 (2 pages).

Gold et al., "Aptamer-Based Multiplexed Proteomic Technology for Biomarker Discovery," PLoS ONE, Dec. 2010, vol. 5, No. 12, e15004, pp. 1-17.

Mehan et al., "Highly Multiplexed Proteomic Platform for Biomarker Discovery, Diagnostics, and Therapeutics," Advances in Experimental Medicine and Biology, 2013, vol. 735, Chapter 20, pp. 283-300.

NCBI Accession No. AAA52555.1, downloaded Nov. 8, 2022 (1 page).

NCBI Accession No. AAA61139.1, downloaded Nov. 8, 2022 (2 pages).

NCBI Accession No. AAC16450.1, downloaded Nov. 8, 2022 (2 pages).

NCBI Accession No. AAG33848.1, downloaded Nov. 8, 2022 (4 pages).

NCBI Accession No. AAH11787.1, downloaded Nov. 8, 2022 (2 pages).

NCBI Accession No. AAH15768.1, downloaded Nov. 8, 2022 (2 pages).

NCBI Accession No. AAH20690.1, downloaded Nov. 8, 2022 (2 pages).

NCBI Accession No. AAH28152.1, downloaded Nov. 8, 2022 (2 pages).

NCBI Accession No. AAH36451.1, downloaded Nov. 8, 2022 (2 pages).

NCBI Accession No. AAH49194.1, downloaded Nov. 8, 2022 (2 pages).

NCBI Accession No. AAH93977.1, downloaded Nov. 8, 2022 (2 pages).

NCBI Accession No. AAH96364.3, downloaded Nov. 8, 2022 (2 pages).

NCBI Accession No. AAI01607.1, downloaded Nov. 8, 2022 (2 pages).

NCBI Accession No. AAI13627.1, downloaded Nov. 8, 2022 (2 pages).

NCBI Accession No. AAI17423.1, downloaded Nov. 8, 2022 (2 pages).

NCBI Accession No. AAI30576.1, downloaded Nov. 8, 2022 (2 pages).

NCBI Accession No. AAI31784.1, downloaded Nov. 8, 2022 (2 pages).

NCBI Accession No. AAI32914.1, downloaded Nov. 8, 2022 (2 pages).

NCBI Accession No. AAI37097.1, downloaded Nov. 8, 2022 (2 pages).

NCBI Accession No. AAI43497.1, downloaded Nov. 8, 2022 (3 pages).

NCBI Accession No. AAI44052.1, downloaded Nov. 8, 2022 (2 pages).

NCBI Accession No. AAI46915.1, downloaded Nov. 8, 2022 (2 pages).

NCBI Accession No. AAI52430.1, downloaded Nov. 8, 2022 (2 pages).

NCBI Accession No. AAP35560.1, downloaded Nov. 8, 2022 (1 page).

NCBI Accession No. AAP36088.1, downloaded Nov. 8, 2022 (1 page).

NCBI Accession No. AAQ88873.1, downloaded Nov. 8, 2022 (1 page).

NCBI Accession No. ABD72606.1, downloaded Nov. 8, 2022 (2 pages).

NCBI Accession No. AQY76658.1, downloaded Nov. 8, 2022 (1 page).

Tong et al., "Management of postpartum pulmonary embolism combined with retained placenta accreta," Medicine (Baltimore), 2019, vol. 98, No. 38, e17219, pp. 1-4.

Tseng et al., "Differential Expression of Growth-, Angiogenesis- and Invasion-Related Factors in The Development of Placenta Accreta," Taiwanese Journal of Obstetrics and Gynecology, Jun. 2006, vol. 45, No. 2, pp. 100-106.

International Search Report and Written Opinion mailed Jul. 8, 2021 in corresponding International PCT Patent Application No. PCT/US2021/014299 (14 pages).

NCBI Accession No. AQY76900.1, downloaded Nov. 8, 2022 (1 page).

NCBI Accession No. AQY76901.1, downloaded Nov. 8, 2022 (1 page).

NCBI Accession No. CAA25240.1, downloaded Nov. 8, 2022 (2 pages).

NCBI Accession No. CAG33708.1, downloaded Nov. 8, 2022 (1 page).

NCBI Accession No. EAW52436.1, downloaded Nov. 8, 2022 (2 pages).

NCBI Accession No. EAX10958.1, downloaded Nov. 8, 2022 (2 pages).

NCBI Accession No. NP_001269314.1, downloaded Nov. 8, 2022 (3 pages).

(56) References Cited

OTHER PUBLICATIONS

NCBI Accession No. XP_011509265.1, downloaded Nov. 8, 2022
(1 page).

* cited by examiner

Observations (axes F1 and F2: 81.70 %)

PCK1
NBAMT1
ESD
COMMD7
GSTP1
IDE

F2 (12.12 %)

F1 (69.58 %)

● Case  ○ Control

Observations (axes F1 and F2: 86.90 %)

PGK1
NBAMT1
ESD
COMMD7
GSTP1

Control Control
Control

Control
Control Control

Control

Control

Case

Case Control

Case
Case
Control
Case

Control Case

Case

Case Case Case

Case Case
Case Case

Case Case
Case

F2 (13.59 %)

F1 (73.30 %)

● Case  ○ Control

Observations (axes F1 and F2: 79.62 %)

BIOMARKERS FOR PLACENTA ACCRETA SPECTRUM (PAS) DISORDERS

CROSS-REFERENCE TO RELATED APPLICATION

This application is the U.S. National Stage Application, pursuant to 35 U.S.C. § 371 of PCT International Application No. PCT/US2021/014299, filed Jan. 21, 2021 designating the United States and published in English, which claims priority to and the benefit of the following U.S. Provisional Application No. 62/964,449, filed Jan. 22, 2020, the entire contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 16, 2021, is named 167688_020301_PCT_SL.txt and is 161,491 bytes in size.

BACKGROUND OF THE INVENTION

Placenta accreta spectrum (PAS) (including histopathologic and/or clinical diagnoses of placenta accreta, placenta increta, or placenta percreta) is a condition where the placenta becomes adherent to the uterus with variable degrees of invasion. PAS is a major cause of maternal morbidity and mortality, often resulting in hysterectomy and large-volume hemorrhage during delivery. Maternal outcomes are optimized when accurate antenatal diagnosis is made, allowing for advanced surgical planning and optimal outcomes at a Center of Excellence. However, a prenatal PAS diagnosis by imaging is imprecise. There are currently no tests that can be used as an aid in the diagnosis or prognosis of PAS. Currently, there are no clinically reliable blood or urine biomarkers for PAS. Impaired decidualization, angiogenesis, and trophoblast-related factors have been suggested to contribute to the pathophysiology of PAS. Investigators have evaluated angiogenic markers, aneuploidy serum analytes, and fetal fraction from non-invasive prenatal screening, but none have resulted in a clinically useful test for PAS. In clinical practice, up to 50% of pregnancies with PAS go undiagnosed prior to delivery, resulting in increased morbidity. Identification of early markers of PAS is necessary for earlier diagnosis as well as identifying pathogenic pathways that could be targeted to prevent or treat PAS. Thus, a new and improved paradigm is urgently needed for early and accurate diagnosis.

SUMMARY OF THE INVENTION

As described below, the present invention features compositions and methods for characterizing placenta accreta spectrum (PAS).

One aspect of the present invention features a panel for characterizing placenta accreta spectrum in a pregnant subject, the panel including one or more distinct capture molecules bound to a substrate, wherein each capture molecule specifically binds a polypeptide or polynucleotide biomarker that is any one or more of antithrombin III, plasminogen activator inhibitor 1, soluble Tie2 and soluble VEGF receptor 2. In some embodiments, the panel includes two, three or four distinct capture molecules. In some embodiments, the panel includes four distinct capture molecules each of which specifically binds polypeptide biomarkers antithrombin III, plasminogen activator inhibitor 1, soluble Tie2 and soluble VEGF receptor 2. In some embodiments, the panel further includes one or more distinct capture molecules, where each capture molecule specifically binds a polypeptide or polynucleotide biomarker selected from the group consisting of Notch1, Tissue inhibitor of metalloproteinase 3, ADAMTS1, SERPINE1, SERPINC1, RGMA, von Willebrand factor, Platelet factor 4, IL37, complement component 8, and Lymphotoxin A2/B1. In some embodiments, the panel further includes a capture molecule that specifically binds a polypeptide or polynucleotide selected from the group consisting of Notch1, SERPINC1, and RGMA. In some embodiments, In some embodiments, the panel further includes one or more distinct capture molecules, where each capture molecule specifically binds a polypeptide or polynucleotide biomarker selected from the group consisting of Complement component C8, Apolipoprotein M, WAP, kazal, immunoglobulin, kunitz and NTR domain-containing protein 1, Growth hormone receptor, Human Chorionic Gonadotropin, CD33, Vascular endothelial growth factor receptor 2, Interleukin-18 receptor 1, Reticulon-4 receptor, Angiopoietin-1 receptor, soluble, Secreted frizzled-related protein 3, Toll-like receptor 4: Lymphocyte antigen 96 complex, Cathepsin F, Interleukin-37, Muellerian-inhibiting factor, CD166 antigen, Mediator of RNA polymerase II transcription subunit 1, Ubiquitin-conjugating enzyme E2 G2, Interleukin-13 receptor subunit alpha-1, Immunoglobulin superfamily containing leucine-rich repeat protein 2, Cadherin-5, Neurogenic locus notch homolog protein 1, C-C motif chemokine 3-like 1, Tumor necrosis factor receptor superfamily member 21, Lymphotoxin alpha2: beta1, Epidermal growth factor receptor, A disintegrin and metalloproteinase with thrombospondin motifs 13, Carbonic anhydrase-related protein 10, Ectodysplasin-A, secreted form, Neural cell adhesion molecule L1-like protein, Repulsive guidance molecule A, Sphingosine kinase 2, Endothelin-converting enzyme 1, Complement C2, Interleukin-1 Receptor accessory protein, and Alpha-2-antiplasmin. In some embodiments, the panel further includes one or more distinct capture molecules, where each capture molecule specifically binds a polypeptide or polynucleotide biomarker selected from the group consisting of Gremlin-1, A disintegrin and metalloproteinase with thrombospondin motifs 1, Calcium/calmodulin-dependent protein kinase 1, Cryptic protein, Cadherin-12, DnaJ homolog subfamily B member 1, Pescadillo homolog, Metalloproteinase inhibitor 3, L-lactate dehydrogenase B chain, Casein kinase II 2-alpha: 2-beta heterotetramer, Peroxiredoxin-6, and Platelet factor 4. In some embodiments, the panel further includes one or more distinct capture molecules, where each capture molecule specifically binds a polypeptide or polynucleotide biomarker selected from the group consisting of Tissue inhibitor of metalloproteinase 3, ADAMTS1, SERPINE1, von Willebrand factor, and Platelet factor 4. In some embodiments, the panel further includes one or more distinct capture molecules, where each capture molecule specifically binds a polypeptide or polynucleotide biomarker selected from the group consisting of Human Chorionic Gonadotropin, Lymphotoxin alpha2: beta1, Cathepsin F, and repulsive guidance molecule bmp co-receptor A. In some embodiments, the panel further includes one or more distinct capture molecules, where each capture molecule specifically binds a polypeptide or polynucleotide biomarker selected from the group consisting of Complement component C8, Apolipoprotein M, WAP, kazal, immunoglobulin, kunitz and NTR domain-containing protein 1, Growth hormone receptor, Human Chorionic Gonadotropin, CD33, Vascular endothelial growth factor receptor 2, Interleukin-18 receptor 1, Reticulon-4 receptor, Angiopoietin-1 receptor, soluble, Secreted frizzled-related protein 3, Toll-like receptor 4, Lymphocyte antigen 96 complex, Cathepsin F, Interleukin-37, Muellerian-inhibiting factor, CD166 antigen, Mediator of RNA polymerase II transcription subunit 1, Ubiquitin-conjugating enzyme E2 G2, Interleukin-13 receptor subunit alpha-1, Immunoglobulin superfamily containing leucine-rich repeat protein 2, Cadherin-5, Neurogenic locus notch homolog protein 1, C-C motif chemokine 3-like 1, Tumor necrosis factor receptor superfamily member 21, Lymphotoxin alpha2: beta1, Epidermal growth factor receptor, A disintegrin and metalloproteinase with thrombospondin motifs 13, Carbonic anhydrase-related protein 10, Ectodysplasin-A, secreted form, Neural cell adhesion molecule L1-like protein, Repulsive guidance molecule A, Sphingosine kinase 2, Endothelin-converting enzyme 1, Complement C2, Interleukin-1 Receptor accessory protein, Alpha-2-antiplasmin, Antithrombin-III, Gremlin-1, A disintegrin and metalloproteinase with thrombospondin motifs 1, Calcium/calmodulin-dependent protein kinase 1, Plasminogen activator inhibitor 1, Cryptic protein, Cadherin-12, DnaJ homolog subfamily B member 1, Pescadillo homolog, Metalloproteinase inhibitor 3, L-lactate dehydrogenase B chain, Casein kinase II 2-alpha': 2-beta heterotetramer, Peroxiredoxin-6, and Platelet factor 4.

In another aspect, a panel is provided for characterizing placenta accreta spectrum in a pregnant subject, the panel including one or more distinct capture molecules bound to a substrate, wherein each capture molecule specifically binds a polypeptide or polynucleotide biomarker selected from the group consisting of LTA/LTB, SERPINC1, SERPINE1, KDR, CD33, IL37, TEK, ADAMTS13, TIMP3, CTSF, and AMH. In some embodiments, the panel includes two, three or four distinct capture molecules. In some embodiments, the panel includes the panel further includes four distinct capture molecules, where each capture molecule specifically binds a polypeptide or polynucleotide biomarker selected from the group consisting of LTA/LTB, SERPINC1, and SERPINE1. In some embodiments, the panel includes four distinct capture molecules, where each capture molecule specifically binds a polypeptide or polynucleotide biomarker selected from the group consisting of KDR, CD33, IL37, and TEK. In some embodiments, the panel includes four distinct capture molecules, where each capture molecule specifically binds a polypeptide or polynucleotide biomarker selected from the group consisting of ADAMTS13, TIMP3, CTSF, and AMH. In some embodiments of either of the foregoing aspects, the subject is in the third trimester of pregnancy.

Another aspect provides a panel for characterizing placenta accreta spectrum in a pregnant subject that includes one or more distinct capture molecules bound to a substrate, where each capture molecule specifically binds a polypeptide or polynucleotide biomarker selected from the group consisting of CD5L, FGF5, ESM1, S100A7, and MMP17. In some embodiments, the panel includes two, three, four or five distinct capture molecules. In some embodiments, the panel includes four distinct capture molecules each of which specifically binds polypeptide or polynucleotide biomarkers CD5 Molecule Like, Fibroblast Growth Factor 5, ESM1, and S100 Calcium Binding Protein A7. In some embodiments, the panel also includes distinct capture molecules each of which specifically binds polypeptide or polynucleotide biomarkers XPNPEP1, EIF4H, IDE, and SMAD3. In some embodiments, the panel also includes distinct capture molecules each of which specifically binds polypeptide or polynucleotide biomarkers Anti-Mullerian Hormone, Interleukin 7 Receptor, Matrix Metallopeptidase 17, Complement C9, Chitinase 3 Like 1, GDNF Family Receptor Alpha 3, Plasminogen Activator, Tissue Type, Colony Stimulating Factor 1 Receptor, Ephrin A2, Dermatopontin, Delta Like Canonical Notch Ligand 1, Interleukin 5 Receptor Subunit Alpha, Lymphocyte Activating 3, Follistatin Like 3, SPARC, SPOCK2, Laminin Subunit Alpha 1, Laminin Subunit Beta 1, Laminin Subunit Gamma 1, Kirre Like Nephrin Family Adhesion Molecule 3, Calcium/Calmodulin Dependent Protein Kinase I, SRC Proto-Oncogene, Non-Receptor Tyrosine Kinase), Glucose-6-Phosphate Isomerase, N-Acetylglucosamine Kinase, Eukaryotic Translation Initiation Factor 5A), N-Myristoyltransferase 1, Vesicle Trafficking 1, Sphingosine Kinase 1, Ribosomal Protein S6 Kinase A5, Protein Kinase C Alpha, Aldolase, Fructose-Bisphosphate A, Mitogen-Activated Protein Kinase 3, Protein Tyrosine Phosphatase Non-Receptor Type 1, Fibronectin Leucine Rich Transmembrane Protein 1 (FLRT1), Growth Factor Receptor Bound Protein 2, Sorting Nexin 4, Enolase 2, Glycogen Synthase Kinase 3 Alpha, Glycogen Synthase Kinase 3 Beta, 3-Phosphoinositide Dependent Protein Kinase 1, C—X—C Motif Chemokine Ligand 6, SMAD Family Member 2, SBDS Ribosome Maturation Factor, CAMP Regulated Phosphoprotein 19, Inhibitor Of Growth Family Member 1, Drebrin Like, Ubiquitin-Fold Modifier Conjugating Enzyme 1, Cytochrome P450 Family 3 Subfamily A Member 4, Glutathione S-Transferase Pi 1, N-6 Adenine-Specific DNA Methyltransferase 1, Histone Deacetylase 8, DEAD-Box Helicase 19B, BCL2 Like 1, SMAD Family Member 3, NME/NM23 Nucleoside Diphosphate Kinase 2, Phosphoglycerate Kinase 1, AKT Serine/Threonine Kinase 2, Protein Kinase C Delta, Casein Kinase 2 Alpha 1, Platelet Activating Factor Acetylhydrolase 1b Catalytic Subunit 2, Protein Tyrosine Phosphatase Non-Receptor Type 11, Copine 1, Interleukin 23 Receptor, and Insulin Degrading Enzyme. In some embodiments, the subject is in the second trimester.

Another aspect provides a panel for characterizing placenta accreta spectrum in a pregnant subject that includes one or more distinct capture molecules bound to a substrate, wherein each capture molecule specifically binds a polypeptide or polynucleotide biomarker selected from the group consisting of PGK1, N6AMT1, ESD, COMMD7, GSTP1, IDE, DBNL, LY86, and DDX19b. In some embodiments, the panel includes five, six, seven, eight, or nine distinct capture molecules. In some embodiments, the panel includes five distinct capture molecules each of which specifically binds polypeptide or polynucleotide biomarkers PGK1, N6AMT1, ESD, COMMD7, and GSTP1. In some embodiments, the panel includes six distinct capture molecules each of which specifically binds polypeptide or polynucleotide biomarkers PGK1, N6AMT1, ESD, COMMD7, GSTP1, and IDE. In some embodiments, the panel includes nine distinct capture molecules each of which specifically binds polypeptide or polynucleotide biomarkers PGK1, N6AMT1, ESD, COMMD7, GSTP1, IDE, DBNL, LY86, and DDX19b.

Another aspect provides a panel for characterizing placenta accreta spectrum in a pregnant subject that includes one or more distinct capture molecules bound to a substrate, wherein each capture molecule specifically binds a polypeptide or polynucleotide biomarker selected from the group consisting of IDE, IL23R, CPNE1, XPNPEP1, PAFAHIB2, PTPN11, PRKCD, and PGK1. In some embodiments, the panel includes five, six, seven, or eight distinct capture molecules. In some embodiments, the panel includes five distinct capture molecules each of which specifically binds polypeptide or polynucleotide biomarkers IDE, IL23R, CPNE1, XPNPEP1, and PAFAHIB2. In some embodiments, the panel includes five distinct capture molecules each of which specifically binds polypeptide or polynucleotide biomarkers IDE, IL23R, CPNE1, XPNPEP1, PAFAHIB2, PTPN11, and PRKCD. In some embodiments, the panel includes eight distinct capture molecules each of which specifically binds polypeptide or polynucleotide biomarkers IDE, IL23R, CPNE1, XPNPEP1, PAFAHIB2, PTPN11, PRKCD, and PGK1. In some embodiments, the subject is in the second trimester.

Another aspect provides a panel for characterizing placenta accreta spectrum in a pregnant subject that includes one or more distinct capture molecules bound to a substrate, wherein each capture molecule specifically binds a polypeptide or polynucleotide biomarker selected from the group consisting of CD5L, FGF5, ESM1, S100A7, IL23R, IDE, CSF1R, and FSTL3. In some embodiments, the panel includes four distinct capture molecules each of which specifically binds polypeptide or polynucleotide biomarkers CD5L, FGF5, ESM1, and S100A7. In some embodiments, the panel includes four distinct capture molecules each of which specifically binds polypeptide or polynucleotide biomarkers IL23R, IDE, CSF1R, and FSTL3. In some embodiments, the subject is in the second trimester.

In some embodiments of any of the foregoing aspects, the capture molecule is a polypeptide, polynucleotide, aptamer, or analog thereof. In some embodiments, the capture molecule is an antibody.

Another aspect provides a method for characterizing placenta accreta spectrum biomarkers in a biological sample, the method involving contacting a biological sample of the subject with a panel of the foregoing aspects and embodiments.

A method is also provided for characterizing placenta accreta spectrum biomarkers in a biological sample of a subject in the third trimester, the method comprising contacting a biological sample of the subject with a capture molecule and detecting an increase in the level of the biomarker, wherein the biomarker is selected from the group consisting of antithrombin III, plasminogen activator inhibitor 1, soluble Tie2, soluble VEGF receptor 2, Complement component C8, Apolipoprotein M, WAP, kazal, immunoglobulin, kunitz and NTR domain-containing protein 1, Growth hormone receptor, Human Chorionic Gonadotropin, CD33, Vascular endothelial growth factor receptor 2, Interleukin-18 receptor 1, Reticulon-4 receptor, Angiopoietin-1 receptor, soluble, Secreted frizzled-related protein 3, Toll-like receptor 4: Lymphocyte antigen 96 complex, Cathepsin F, Interleukin-37, Muellerian-inhibiting factor, CD166 antigen, Mediator of RNA polymerase II transcription subunit 1, Ubiquitin-conjugating enzyme E2 G2, Interleukin-13 receptor subunit alpha-1, Immunoglobulin superfamily containing leucine-rich repeat protein 2, Cadherin-5, Neurogenic locus notch homolog protein 1, C-C motif chemokine 3-like 1, Tumor necrosis factor receptor superfamily member 21, Lymphotoxin alpha2: beta1, Epidermal growth factor receptor, A disintegrin and metalloproteinase with thrombospondin motifs 13, Carbonic anhydrase-related protein 10, Ecto-dysplasin-A, secreted form, Neural cell adhesion molecule L1-like protein, Repulsive guidance molecule A, Sphingosine kinase 2, Endothelin-converting enzyme 1, Complement C2, Interleukin-1 Receptor accessory protein, and Alpha-2-antiplasmin. In some embodiments, the method also involves detecting a reduction in a biomarker selected from the group consisting of Gremlin-1, A disintegrin and metalloproteinase with thrombospondin motifs 1, Calcium/calmodulin-dependent protein kinase kinase 1, Cryptic protein, Cadherin-12, DnaJ homolog subfamily B member 1, Pescadillo homolog, Metalloproteinase inhibitor 3, L-lactate dehydrogenase B chain, Casein kinase II 2-alpha: 2-beta heterotetramer, Peroxiredoxin-6, Platelet factor 4, and plasminogen activator inhibitor 1.

Another method provided herein for characterizing placenta accreta spectrum biomarkers in a biological sample of a subject in the second trimester involves contacting a biological sample of the subject with a capture molecule and detecting an increase in the level of the biomarker, wherein the biomarker is selected from the group consisting of CD5L, FGF5, ESM1, MMP17, and S100A7. In some embodiments, the method also involves detecting a reduction in a biomarker selected from the group consisting of XPNPEP1, EIF4H, IDE, and SMAD3.

Another aspect provides a method for characterizing placenta accreta spectrum biomarkers in a biological sample of a subject in the second trimester, the method comprising contacting a biological sample of the subject with capture molecules each of which specifically binds polypeptide biomarkers selected from the group consisting of PGK1, N6AMT1, ESD, COMMD7, GSTP1, and IDE; PGK1, N6AMT1, ESD, COMMD7, and GSTP1; PGK1, N6AMT1, ESD, COMMD7, GSTP1, IDE, DBNL, LY86, and DDX19b; IDE, IL23R, CPNE1, XPNPEP1, and PAFA-HIB2; IDE, IL23R, CPNE1, XPNPEP1, PAFAHIB2, PTPN11, and PRKCD; and IDE, IL23R, CPNE1, XPN-PEP1, PAFAHIB2, PTPN11, PRKCD, and PGK1, and detecting a change in the levels of the biomarkers.

Another aspect provides a method for characterizing placenta accreta spectrum in a pregnant subject, the method involving characterizing placenta accreta spectrum biomarkers in the pregnant subject using a marker delineated in any of the above aspects and determining the body mass index (BMI) of the subject. In some embodiments, this method also involves acquiring a clinical history for the subject or acquiring images of the subject's uterus.

In one aspect, a method is provided for characterizing a pregnant subject, the method involving characterizing placenta accreta spectrum biomarkers in the pregnant subject using the steps of any one of the above methods of and obtaining ultrasound imaging of the pregnant subject's uterus. In some embodiments, this method also involves acquiring a clinical history for the subject.

Another aspect provides a kit for characterizing markers in a sample, the kit comprising two or more capture molecules fixed to a substrate surface, wherein each capture molecule specifically binds a marker polypeptide of Table 1A, Table 1B, or both, or a polynucleotide encoding said marker polypeptide.

The disclosure provides compositions and methods that are useful in detecting placenta accreta spectrum. Compositions and articles defined in the disclosure were isolated or otherwise manufactured in connection with the examples provided below. Other features and advantages of the aspects and embodiments described herein will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention:

Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "aptamer" is meant a modified DNA or RNA molecule that binds with high affinity to a target protein. Aptamers can be used as tools for biomarker or drug discovery.

By "biologic sample" is meant any tissue, cell, fluid, or other material derived from an organism. For example, placental, uterine, blood, and urine samples are biosamples.

A "biomarker" or "marker" as used herein generally refers to a protein, nucleic acid molecule, clinical indicator, or other analyte that is associated with a disease. In one embodiment, a marker of placenta accreta spectrum is differentially present in a biological sample obtained from a subject having or at risk of developing a pathologic adherence of the placenta, such as placenta increta, placenta percreta, and placenta accreta relative to a reference. A marker is differentially present if the mean or median level of the biomarker present in the sample is statistically different from the level present in a reference. A reference level may be, for example, the level present in a sample obtained from a healthy control subject or the level obtained from the subject at an earlier timepoint, i.e., prior to treatment. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. The differential presence of a marker of the invention in a subject sample can be useful in characterizing the subject as having or at risk of developing a pathologic adherence of the placenta, for determining the prognosis of the subject, for evaluating therapeutic efficacy, or for selecting a treatment regimen (e.g., selecting that the subject be evaluated and/or treated by a surgeon that specializes in gynecology and obstetrics). Markers useful in the panels of the invention include, for example, Complement component C8 (C8A C8B C8G), Apolipoprotein M (APOM), WAP, kazal, immunoglobulin, kunitz and NTR domain-containing protein 1 (WFIKKN1), Growth hormone receptor (GHR), Human Chorionic Gonadotropin (CGA CGB), Myeloid cell surface antigen CD33 (CD33), Vascular endothelial growth factor receptor 2 (KDR), Interleukin-18 receptor 1 (IL18R1), Reticulon-4 receptor (RTN4R), Angiopoietin-1 receptor, soluble (TEK), Secreted frizzled-related protein 3 (FRZB), Toll-like receptor 4: Lymphocyte antigen 96 complex (TLR4 LY96), Cathepsin F (CTSF), Interleukin-37 (IL37), Muellerian-inhibiting factor (AMH), CD166 antigen (ALCAM), Mediator of RNA polymerase II transcription subunit 1 (MED1), Ubiquitin-conjugating enzyme E2 G2 (UBE2G2), Interleukin-13 receptor subunit alpha-1 (IL13RA1), Immunoglobulin superfamily containing leucine-rich repeat protein 2 (ISLR2), Cadherin-5 (CDH5), Neurogenic locus notch homolog protein 1 (NOTCH1), C-C motif chemokine 3-like 1 (CCL3L1), Tumor necrosis factor receptor superfamily member 21 (TNFRSF21), Lymphotoxin alpha2: beta1 (LTA LTB), Epidermal growth factor receptor (EGFR), A disintegrin and metalloproteinase with thrombospondin motifs 13 (ADAMTS13), Carbonic anhydrase-related protein 10 (CA10), Ectodysplasin-A, secreted form (EDA), Neural cell adhesion molecule L1-like protein (CHL1), Repulsive guidance molecule A (RGMA), Sphingosine kinase 2 (SPHK2), Endothelin-converting enzyme 1 (ECE1), Complement C2 (C2), Interleukin-1 Receptor accessory protein (IL1RAP), Alpha-2-antiplasmin (SERPINF2), Antithrombin-III (SERPINC1), Gremlin-1 (GREM1), A disintegrin and metalloproteinase with thrombospondin motifs 1 (ADAMTS1), Calcium/calmodulin-dependent protein kinase 1 (CAMKK1), Plasminogen activator inhibitor 1 (SERPINE1), Cryptic protein (CFC1), Cadherin-12 (CDH12), DnaJ homolog subfamily B member 1 (DNAJB1), Pescadillo homolog (PES1), Metalloproteinase inhibitor 3 (TIMP3), L-lactate dehydrogenase B chain (LDHB), Casein kinase II 2-alpha': 2-beta heterotetramer (CSNK2A2 CSNK2B), Peroxiredoxin-6 (PRDX6), and Platelet factor 4 (PF4), In some embodiments, a panel of second trimester PAS biomarkers comprises Anti-Mullerian Hormone (AMH), CD5 Molecule Like (CD5L), Interleukin 7 Receptor (IL7R), Matrix Metallopeptidase 17 (MMP17), Complement C9 (C9), Chitinase 3 Like 1 (CHI3L1), Endothelial Cell Specific Molecule 1 (ESM1), GDNF Family Receptor Alpha 3 (GFRA3), Plasminogen Activator, Tissue Type (PLAT), S100 Calcium Binding Protein A7 (S100A7), Colony Stimulating Factor 1 Receptor (CSF1R), Ephrin A2 (EFNA2), Dermatopontin (DPT), Delta Like Canonical Notch Ligand 1 (DLL1), Interleukin 5 Receptor Subunit Alpha (IL5RA), Lymphocyte Activating 3 (LAG3), Follistatin Like 3 (FSTL3), Fibroblast Growth Factor 5 (FGF5), SPARC (Osteonectin, Cwcv And Kazal Like Domains Proteoglycan 2 (SPOCK2), Laminin Subunit Alpha 1 (*LAMA*1 Laminin Subunit Beta 1 (LAMB1 Laminin Subunit Gamma 1 (LAMC1), Kirre Like Nephrin Family Adhesion Molecule 3 (KIRREL3), Calcium/Calmodulin Dependent Protein Kinase I (CAMK1), SRC Proto-Oncogene, Non-Receptor Tyrosine Kinase (SRC), Glucose-6-Phosphate Isomerase (GPI), N-Acetylglucosamine Kinase (NAGK), Eukaryotic Translation Initiation Factor 5A (EIF5A), N-Myristoyltransferase 1 (NMT1), Vesicle Trafficking 1 (VTA1), Sphingosine Kinase 1 (SPHK1), Ribosomal Protein S6 Kinase A5 (RPS6KA5), Protein Kinase C Alpha (PRKCA), Aldolase, Fructose-Bisphosphate A (ALDOA), Mitogen-Activated Protein Kinase 3 (MAPK3), Protein Tyrosine Phosphatase Non-Receptor Type 1 (PTPN1), Fibronectin Leucine Rich Transmembrane Protein 1 (FLRT1), Growth Factor Receptor Bound Protein 2 (GRB2), Sorting Nexin 4 (SNX4), Enolase 2 (ENO2), Glycogen Synthase Kinase 3 Alpha (GSK3A Glycogen Synthase Kinase 3 Beta (GSK3B), 3-Phosphoinositide Dependent Protein Kinase 1 (PDPK1), C—X—C Motif Chemokine Ligand 6 (CXCL6), SMAD Family Member 2 (SMAD2), SBDS Ribosome Maturation Factor (SBDS), CAMP Regulated Phosphoprotein 19 (ARPP19), Inhibitor Of Growth Family Member 1 (ING1), Drebrin Like (DBNL), Ubiquitin-Fold Modifier Conjugating Enzyme 1 (UFC1), Cytochrome P450 Family 3 Subfamily A Member 4 (CYP3A4), Glutathione S-Transferase Pi 1 (GSTP1), N-6 Adenine-Specific DNA Methyltransferase 1 (N6AMT1), Histone Deacetylase 8 (HDAC8), DEAD-Box Helicase 19B (DDX19B), BCL2 Like 1 (BCL2L1), SMAD Family Member 3 (SMAD3), NME/NM23 Nucleoside Diphosphate Kinase 2 (NME2), Phosphoglycerate Kinase 1 (PGK1), AKT Serine/Threonine Kinase 2 (AKT2), Protein Kinase C Delta (PRKCD), Casein Kinase 2 Alpha 1 (CSNK2A1), Platelet Activating Factor Acetylhydrolase 1b Catalytic Subunit 2 (PAFAH1B2), Protein Tyrosine Phosphatase Non-Receptor Type 11 (PTPN11), Copine 1 (CPNE1), Interleukin 23 Receptor (IL23R), and Insulin Degrading Enzyme (IDE) as well as the nucleic acid molecules encoding such proteins. Fragments useful in the methods of the invention are sufficient to bind an antibody that specifically recognizes the protein from which the fragment is derived. The invention includes markers that are substantially identical to the following sequences. Preferably, such a sequence is at least 85%, 90%, 95% or even 99% identical at the amino acid level or nucleic acid to the sequence used for comparison.

By "Phosphoglycerate Kinase 1 (PGK1)" is meant a polypeptide or fragment thereof having at least about 85% amino acid identity to GENBANK Accession No. AAI13569.1. An exemplary polypeptide sequence is provided below:

```
>AAI13569.1 Phosphoglycerate kinase 1 [Homo
sapiens]
                              (SEQ ID NO: 1)
MSLSNKLTLDKLDVKGKRVVMRVDFNVPMKNNQITNNQRIKAAVPSIKFC

LDNGAKSVVLMSHLGRPDGVPMPDKYSLEPVAVELKSLLGKDVLFLKDCV

GPEVEKACANPAAGSVILLENLRFHVEEEGKGKDASGNKVKAEPAKIEAF

RASLSKLGDVYVNDAFGTAHRAHSSMVGVNLPQKAGGFLMKKELNYFAKA

LESPERPFLAILGGAKVADKIQLINNMLDKVNEMIIGGGMAFTFLKVLNN

MEIGTSLFDEEGAKIVKDLMSKAEKNGVKITLPVDFVTADKFDENAKTGQ

ATVASGIPAGWMGLDCGPESSKKYAEAVTRAKQIVWNGPVGVFEWEAFAR

GTKALMDEVVKATSRGCITIIGGGDTATCCAKWNTEDKVSHVSTGGGASL

ELLEGKVLPGVDALSNI
```

By "N-6 Adenine-Specific DNA Methyltransferase 1 (N6AMT1)" is meant a polypeptide or fragment thereof having at least about 85% amino acid identity to NCBI Reference Sequence: NP 037372.4. An exemplary polypeptide sequence is provided below:

```
>NP_037372.4 methyltransferase N6AMT1 isoform 1
[Homo sapiens]
                              (SEQ ID NO: 2)
MAGENFATPPFHGHVGRGAFSDVYEPAEDTFLLLDALEAAAAELAGVEICL

EVGSGSGVVSAFLASMIGPQALYMCTDINPEAAACTLETARCNKVHIQPV

ITDLVKGLLPRLTEKVDLLVFNPPYVVTPPQEVGSHGIEAAWAGGRNGRE

VMDRFFPLVPDLLSPRGLFYLVTIKENNPEEILKIMKTKGLQGTTALSRQ

AGQETLSVLKFTKS
```

By "Esterase D (ESD)" is meant a polypeptide or fragment thereof having at least about 85% amino acid identity to GENBANK Accession No. AAC99788.1. An exemplary polypeptide sequence is provided below:

```
>AAC99788.1 esterase D [Homo sapiens]
                              (SEQ ID NO: 3)
MALKQISSNKCFGGLQKVFEHDSVELNCKMKFAVYLPPKAETGKCPALYW

LSGLTCTEQNFISKSGYHQSASEHGLVVIAPDTSPRGCNIKGEDESWDFG
```

```
TGAGFYVDATEDPWKTNYRMYSYVTEELPQLINANFPVDPQRMSIFGHSM

GGHGALICALKNPGKYKSVSAFAPICNPVLCPWGKKAFSGYLGTDQSKWK

AYDATHLVKSYPGSQLDILIDQGKDDQFLLDGQLLPDNFIAACTEKKIPV

VFRLQEGYDHSYYFIATFITDHIRHHAKYLNA
```

By "COMM Domain Containing 7 (COMMD7)" is meant a polypeptide or fragment thereof having at least about 85% amino acid identity to GENBANK Accession No. AAH00628.3. An exemplary polypeptide sequence is provided below:

```
>AAH00628.3 COMM domain containing 7 [Homo
sapiens]
                              (SEQ ID NO: 4)
MGRLHCTEDPVPEAVGGDMQQLNQLGAQQFSALTEVLFHFLTEPKEVERF

LAQLSEFATTNQISLGSLRSIVKSLLLVPNGALKKSLTAKQVQADFITLG

LSEEKATYFSEKWKQNAPTLARWAIGQTLMINQLIDMEWKFGVTSGSSEL

EKVGSIFLQLKLVVKKGNQTENVYIELTLPQFYSFLHEMERVRTSMECFC
```

By "Glutathione S-Transferase Pi 1 (GSTP1)" is meant a polypeptide or fragment thereof having at least about 85% amino acid identity to GENBANK Accession NP_000843.1. An exemplary polypeptide sequence is provided below:

```
>NP_000843.1 glutathione S-transferase P [Homo
sapiens]
                              (SEQ ID NO: 5)
MPPYTVVYFPVRGRCAALRMLLADQGQSWKEEVVTVETWQEGSLKASCLY

GQLPKFQDGDLTLYQSNTILRHLGRTLGLYGKDQQEAALVDMVNDGVEDL

RCKYISLIYTNYEAGKDDYVKALPGQLKPFETLLSQNQGGKTFIVGDQIS

FADYNLLDLLLIHEVLAPGCLDAFPLLSAYVGRLSARPKLKAFLASPEYV

NLPINGNGKQ
```

By "Insulin Degrading Enzyme (IDE)" is meant a polypeptide or fragment thereof having at least about 85% amino acid identity to GENBANK Accession No. AAH96336.1. An exemplary polypeptide sequence is provided below:

```
>AAH96336.1 Insulin-degrading enzyme [Homo
sapiens]
                              (SEQ ID NO: 6)
MRYRLAWLLHPALPSTFRSVLGARLPPPERLCGFQKKTYSKMNNPAIKRI

GNHITKSPEDKREYRGLELANGIKVLLISDPTTDKSSAALDVHIGSLSDP

PNIAGLSHFCEHMLFLGTKKYPKENEYSQFLSEHAGSSNAFTSGEHTNYY

FDVSHEHLEGALDRFAQFFLCPLFDESCKDREVNAVDSEHEKNVMNDAWR

LFQLEKATGNPKHPFSKFGTGNKYTLETRPNQEGIDVRQELLKFHSAYYS

SNLMAVCVLGRESLDDLTNLVVKLFSEVENKNVPLPEFPEHPFQEEHLKQ

LYKIVPIKDIRNLYVTFPIPDLQKYYKSNPGHYLGHLIGHEGPGSLLSEL

KSKGWVNTLVGGQKEGARGFMFFIINVDLTEEGLLHVEDIILHMFQYIQK

LRAEGPQEWVFQECKDLNAVAFRFKDKERPRGYTSKIAGILHYYPLEEVL

TAEYLLEEFRPDLIEMVLDKLRPENVRVAIVSKSFEGKTDRTEEWYGTQY

KQEAIPDEVIKKWQNADLNGKFKLPTKNEFIPTNFEILPLEKEATPYPAL
```

-continued

IKDTAMSKLWFKQDDKFFLPKACLNFEFFSPFAYVDPLHCNMAYLYLELL

KDSLNEYAYAAELAGLSYDLQNTIYGMYLSVKGYNDKQPILLKKIIEKMA

TFEIDEKRFEIIKEAYMRSLNNFRAEQPHQHAMYYLRLLMTEVAWTKDEL

KEALDDVTLPRLKAFIPQLLSRLHIEALLHGNITKQAALGIMQMVEDTLI

EHAHTKPLLPSQLVRYREVQLPDRGWFVYQQRNEVHNNCGIEIYYQTDMQ

STSENMFLELFCQIISEPCFNTLRTKEQLGYIVFSGPRRANGIQGLRFII

QSEKPPHYLESRVEAFLITMEKSIEDMTEEAFQKHIQALAIRRLDKPKKL

SAECAKYWGEIISQQYNFDRDNTEVAYLKTLTKEDIIKFYKEMLAVDAPR

RHKVSVHVLAREMDSCPVVGEFPCQNDINLSQAPALPQPEVIQNMTEFKR

GLPLFPLVKPHINFMAAKL

By "Drebrin Like (DBNL)" is meant a polypeptide or fragment thereof having at least about 85% amino acid identity to GENBANK Accession No. AAH31687.1. An exemplary polypeptide sequence is provided below:

>AAH31687.1 Drebrin-like [Homo sapiens]
(SEQ ID NO: 7)
MAANLSRNGPALQEAYVRVVTEKSPTDWALFTYEGNSNDIRVAGTGEGGL

EEMVEELNSGKVMYAFCRVKDPNSGLPKFVLINWTGEGVNDVRKGACASH

VSTMASFLKGAHVTINARAEEDVEPECIMEKVAKASGANYSFHKESGRFQ

DVGPQAPVGSVYQKTNAVSEIKRVGKDSFWAKAEKEEENRRLEEKRRAEE

AQRQLEQERRERELREAARREQRYQEQGGEASPQRTWEQQQEVVSRNRNE

QESAVHPREIFKQKERAMSTTSISSPQPGKLRSPFLQKQLTQPETHFGRE

PAAAISRPRADLPAEEPAPSTPPCLVQAEEEAVYEEPPEQETFYEQPPLV

QQQGAGSEHIDHHIQGQGLSGQGLCARALYDYQAADDTEISFDPENLITG

IEVIDEGWWRGYGPDGHFGMFPANYVELIE

By "Lymphocyte Antigen 86 (LY86)" is meant a polypeptide or fragment thereof having at least about 85% amino acid identity to GENBANK Accession No. AAH38846.1. An exemplary polypeptide sequence is provided below:

>AAH38846.1 Lymphocyte antigen 86 [Homo sapiens]
(SEQ ID NO: 8)
MKGFTATLFLWTLIFPSCSGGGGGKAWPTHVVCSDSGLEVLYQSCDPLQD

FGFSVEKCSKQLKSNINIRFGIILREDIKELFLDLALMSQGSSVLNFSYP

ICEAALPKFSFCGRRKGEQIYYAGPVNNPEFTIPQGEYQVLLELYTEKRS

TVACANATIMCS

By "DEAD-Box Helicase 19B (DDX19B)" is meant a polypeptide or fragment thereof having at least about 85% amino acid identity to GENBANK Accession No. CAG33496.1. An exemplary polypeptide sequence is provided below:

>CAG33496.1 DDX19 [Homo sapiens]
(SEQ ID NO: 9)
MATDSWALAVDEQEAAAESLSNLHLKEEKIKPDTNGAVVKTNANAEKTDE

EEKEDRAAQSLLNKLIRSNLVDNTNQVEVLQRDPNSPLYSVKSFEELRLK

PQLLQGVYAMGFNRPSKIQENALPLMLVEPPQNLIAQSQSGTGKTAAFVL

AMLSQVEPANKYPQCLCLSPTYELALQTGKVIEQMGKFYPELKLAYAVRG

NKLERGQKISEQIVIGTPGTVLDWCSKLKFIDPKKIKVFVLDEADVMIAT

QGHQDQSIRIQRMLPRNCQMLLFSATFEDSVWKFAQKVVPDPNVIKLKRE

EETLDTIKQYYVLCSSRDEKFQALCNLYGATTIAQAMIFCHTRKTASWLA

AELSKEGHQVALLSGEMMVEQRAAVIERFREGKEKVLVTTNVCARGIDVE

QVSVVINFDLPVDKDGNPDNETYLHRIGRTGRFGKRGLAVNMVDSKHSMN

ILNRIQEHFNKKIERLDTDDLDEIEKIAN

By "Interleukin 23 Receptor (IL23R)" is meant a polypeptide or fragment thereof having at least about 85% amino acid identity to NCBI Reference Sequence: NP_653302.2. An exemplary polypeptide sequence is provided below:

>NP_653302.2 interleukin-23 receptor precursor
[Homo sapiens]
(SEQ ID NO: 10)
MNQVTIQWDAVIALYILFSWCHGGITNINCSGHIWVEPATIFKMGMNISI

YCQAAIKNCQPRKLHFYKNGIKERFQITRINKTTARLWYKNFLEPHASMY

CTAECPKHFQETLICGKDISSGYPPDIPDEVTCVIYEYSGNMTCTWNAGK

LTYIDTKYVVHVKSLETEEEQQYLTSSYINISTDSLQGGKKYLVWVQAAN

ALGMEESKQLQIHLDDIVIPSAAVISRAETINATVPKTIIYWDSQTTIEK

VSCEMRYKATTNQTWNVKEFDTNFTYVQQSEFYLEPNIKYVFQVRCQETG

KRYWQPWSSLFFHKTPETVPQVTSKAFQHDTWNSGLTVASISTGHLTSDN

RGDIGLLLGMIVFAVMLSILSLIGIFNRSFRTGIKRRILLLIPKWLYEDI

PNMKNSNVVKMLQENSELMNNNSSEQVLYVDPMITEIKEIFIPEHKPTDY

KKENTGPLETRDYPQNSLFDNTTVVYIPDLNTGYKPQISNFLPEGSHLSN

NNEITSLTLKPPVDSLDSGNNPRLQKHPNFAFSVSSVNSLSNTIFLGELS

LILNQGECSSPDIQNSVEEETTMLLENDSPSETIPEQTLLPDEFVSCLGI

VNEELPSINTYFPQNILESHFNRISLLEK

By "Copine 1 (CPNE1)" is meant a polypeptide or fragment thereof having at least about 85% amino acid identity to GENBANK Accession No. CAG33071.1. An exemplary polypeptide sequence is provided below:

>CAG33071.1 CPNE1 [Homo sapiens]
(SEQ ID NO: 11)
MAHCVTLVQLSISCDHLIDKDIGSKSDPLCVLLQDVGGGSWAELGRTERV

RNCSSPEFSKTLQLEYRFETVQKLRFGIYDIDNKTPELRDDDFLGGAECS

LGQIVSSQVLTLPLMLKPGKPAGRGTITVSAQELKDNRVVTMEVEARNLD

KKDFLGKSDPFLEFFRQGDGKWHLVYRSEVIKNNLNPTWKRFSVPVQHFC

GGNPSTPIQVQCSDYDSDGSHDLIGTFHTSLAQLQAVPAEFECIHPEKQQ

KKKSYKNSGTIRVKICRVETEYSFLDYVMGGCQINFTVGVDFTGSNGDPS

SPDSLHYLSPTGVNEYLMALWSVGSVVQDYDSDKLFPAFGFGAQVPPDWQ

VSHEFALNFNPSNPYCVGIQGIVDAYRQALPQVRLYGPTNFAPIINHVAR

FAAQAAHQGTASQYFMLLLLTDGAVTDVEATREAVVRASNLPMSVIIVGV

GGADFEAMEQLDADGGPLHTRSGQAAARDIVQFVPYRRFQNAPREALAQT

VLAEVPTQLVSYFRAQGWAPLKPLPPSAKDPAQAPQA

13

By "X-Prolyl Aminopeptidase 1 (XPNPEP1)" is meant a polypeptide or fragment thereof having at least about 85% amino acid identity to GENBANK Accession No. AAH07579.1. An exemplary polypeptide sequence is provided below:

```
>AAH07579.1 X-prolyl aminopeptidase (aminopep-
tidase P) 1, soluble [Homo sapiens]
                                 (SEQ ID NO: 12)
MPPKVTSELLRQLRQAMRNSEYVTEPIQAYIIPSGDAHQSEYIAPCDCRR

AFVSGFDGSAGTAIITEEHAAMWTDGRYFLQAAKQMDSNWTLMKMGLKDT

PTQEDWLVSVLPEGSRVGVDPLIIPTDYWKKMAKVLRSAGHHLIPVKENL

VDKIWTDRPERPCKPLLTLGLDYTGISWKDKVADLRLKMAERNVMWFVVT

ALDEIAWLFNLRGSDVEHNPVFFSYAIIGLETIMLFIDGDRIDAPSVKEH

LLLDLGLEAEYRIQVHPYKSILSELKALCADLSPREKVWVSDKASYAVSE

TIPKDHRCCMPYTPICIAKAVKNSAESEGMRRAHIKDAVALCELFNWLEK

EVPKGGVTEISAADKAEEFRRQQADFVDLSFPTISSTGPNGAIIHYAPVP

ETNRTLSLDEVYLIDSGAQYKDGTTDVTRTMHFGTPTAYEKECFTYVLKG

HIAVSAAVFPTGTKGHLLDSFARSALWDSGLDYLHGTGHGVGSFLNVHEG

PCGISYKTFSDEPLEAGMIVTDEPGYYEDGAFGIRIENVVLVVPVKTKYN

FNNRGSLTFEPLTLVPIQTKMIDVDSLTDKECDWLNNYHLTCRDVIGKEL

QKQGRQEALEWLIRETQPISKQH
```

By "Platelet Activating Factor Acetylhydrolase 1b Catalytic Subunit 2 (PAFAHIB2)" is meant a polypeptide or fragment thereof having at least about 85% amino acid identity to GENBANK Accession No. CAG33017.1. An exemplary polypeptide sequence is provided below:

```
>CAG33017.1 PAFAH1B2 [Homo sapiens]
                                 (SEQ ID NO: 13)
MSQGDSNPAAIPHAAEDIQGDDRWMSQHNRFVLDCKDKEPDVLFVGDSMV

QLMQQYEIWRELFSPLHALNFGIGGDTTRHVLWRLKNGELENIKPKVIVV

WVGTNNHENTAEEVAGGIEAIVQLINTRQPQAKIIVLGLLPRGEKPNPLR

QKNAKVNQLLKVSLPKLANVQLLDTDGGFVHSDGAISCHDMFDFLHLTGG

GYAKICKPLHELIMQLLEETPEEKQTTIA
```

By "Protein Tyrosine Phosphatase Non-Receptor Type 11 (PTPN11)" is meant a polypeptide or fragment thereof having at least about 85% amino acid identity to GENBANK Accession No. AAH08692.1. An exemplary polypeptide sequence is provided below:

```
>AAH08692.1 PTPN11 protein [Homo sapiens]
                                 (SEQ ID NO: 14)
MTSRRWFHPNITGVEAENLLLTRGVDGSFLARPSKSNPGDFTLSVRRNGA

VTHIKIQNTGDYYDLYGGEKFATLAELVQYYMEHHGQLKEKNGDVIELKY

PLNCADPTSERWFHGHLSGKEAEKLLTEKGKHGSFLVRESQSHPGDFVLS

VRTGDDKGESNDGKSKVTHVMIRCQELKYDVGGGERFDSLTDLVEHYKKN

PMVETLGTVLQLKQPLNTTRINAAEIESRVRELSKLAETTDKVKQGFWEE

FETLQQQECKLLYSRKEGQRQENKNKNRYKNILPFDHTRVVLHDGDPNEP

VSDYINANIIMPEFETKCNNSKPKKSYIATQGCLQNTVNDFWRMVFQENS
```

14

-continued

```
RVIVMTTKEVERGKSKCVKYWPDEYALKEYGVMRVRNVKESAAHDYTLRE

LKLSKVGQGNTERTVWQYHFRTWPDHGVPSDPGGVLDFLEEVHHKQESIM

DAGPVVVHCR
```

By "Protein Kinase C Delta (PRKCD)" is meant a polypeptide or fragment thereof having at least about 85% amino acid identity to GENBANK Accession No. AAH43350.1. An exemplary polypeptide sequence is provided below:

```
>AAH43350.1 Protein kinase C, delta [Homo sapiens]
                                 (SEQ ID NO: 15)
MAPFLRIAFNSYELGSLQAEDEANQPFCAVKMKEALSTERGKTLVQKKPT

MYPEWKSTFDAHIYEGRVIQIVLMRAAEEPVSEVTVGVSVLAERCKKNNG

KAEFWLDLQPQAKVLMSVQYFLEDVDCKQSMRSEDEAKFPTMNRRGAIKQ

AKIHYIKNHEFIATFFGQPTFCSVCKDFVWGLNKQGYKCRQCNAAIHKKC

IDKIIGRCTGTAANSRDTIFQKERFNIDMPHRFKVHNYMSPTFCDHCGSL

LWGLVKQGLKCEDCGMNVHHKCREKVANLCGINQKLLAEALNQVTQRASR

RSDSASSEPVGIYQGFEKKTGVAGEDMQDNSGTYGKIWEGSSKCNINNFI

FHKVLGKGSFGKVLLGELKGRGEYFAIKALKKDVVLIDDDVECTMVEKRV

LTLAAENPFLTHLICTFQTKDHLFFVMEFLNGGDLMYHIQDKGRFELYRA

TFYAAEIMCGLQFLHSKGIIYRDLKLDNVLLDRDGHIKIADFGMCKENIF

GESRASTFCGTPDYIAPEILQGLKYTFSVDWWSFGVLLYEMLIGQSPFHG

DDEDELFESIRVDTPHYPRWITKESKDILEKLFEREPTKRLGVTGNIKIH

PFFKTINWTLLEKRRLEPPFRPKVKSPRDYSNFDQEFLNEKARLSYSDKN

LIDSMDQSAFAGFSFVNPKFEHLLED
```

By "Fibroblast Growth Factor 5 (FGF5)" is meant a polypeptide or fragment thereof having at least about 85% amino acid identity to GENBANK Accession No. AAH74858.1. An exemplary polypeptide sequence is provided below:

```
>AAH74858.1 Fibroblast growth factor 5 [Homo
sapiens]
                                 (SEQ ID NO: 16)
MSLSFLLLLFFSHLILSAWAHGEKRLAPKGQPGPAATDRNPRGSSSRQSS

SSAMSSSSASSSPAASLGSQGSGLEQSSFQWSPSGRRTGSLYCRVGIGFH

LQIYPDGKVNGSHEANMLSVLEIFAVSQGIVGIRGVFSNKFLAMSKKGKL

HASAKFTDDCKFRERFQENSYNTYASAIHRTEKTGREWYVALNKRGKAKR

GCSPRVKPQHISTHFLPRFKQSEQPELSFTVTVPEKKKPPSPIKPKIPLS

APRKNTNSVKYRLKFRFG
```

By "Endothelial Cell Specific Molecule 1 (ESM1)" is meant a polypeptide or fragment thereof having at least about 85% amino acid identity to GENBANK Accession No. AAH11989.1. An exemplary polypeptide sequence is provided below:

```
>AAH11989.1 Endothelial cell-specific molecule 1
[Homo sapiens]
                                 (SEQ ID NO: 17)
MKSVLLLTTLLVPAHLVAAWSNNYAVDCPQHCDSSECKSSPRCERTVLDD

CGCCRVCAAGRGETCYRTVSGMDGMKCGPGLRCQPSNGEDPFGEEFGICK
```

-continued

```
DCPYGTFGMDCRETCNCQSGICDRGTGKCLKFPFFQYSVTKSSNRFVSLT

EHDMASGDGNIVREEVVKENAAGSPVMRKWLNPR
```

By "S100 Calcium Binding Protein A7 (S100A7)" is meant a polypeptide or fragment thereof having at least about 85% amino acid identity to GENBANK Accession No. CAG46961.1. An exemplary polypeptide sequence is provided below:

```
>CAG46961.1 S100A7 [Homo sapiens]
                                    (SEQ ID NO: 18)
MSNTQAERSIIGMIDMFHKYTRRDDKIDKPSLLTMMKENFPNFLSACDKK

GTNYLADVFEKKDKNEDKKIDFSEFLSLLGDIATDYHKQSHGAAPCSGGS

Q
```

By "Eukaryotic Translation Initiation Factor 4H (EIF4H)" is meant a polypeptide or fragment thereof having at least about 85% amino acid identity to GENBANK Accession No. AAH66928.1. An exemplary polypeptide sequence is provided below:

```
>AAH66928.1 Eukaryotic translation initiation
factor 4H [Homo sapiens]
                                    (SEQ ID NO: 19)
MADFDTYDDRAYSSFGGGRGSRGSAGGHGSRSQKELPTEPPYTAYVGNLP

FNTVQGDIDAIFKDLSIRSVRLVRDKDTDKFKGFCYVEFDEVDSLKEALT

YDGALLGDRSLRVDIAEGRKQDKGGFGFRKGGPDDRGFRDDFLGGRGGSR

PGDRRTGPPMGSRFRDGPPLRGSNMDFREPTEEERAQRPRLQLKPRTVAT

PLNQVANPNSAIFGGARPREEVVQKEQE
```

By "Matrix Metallopeptidase 17 (MMP17)" is meant a polypeptide or fragment thereof having at least about 85% amino acid identity to GENBANK Accession No. AAH45610.1. An exemplary polypeptide sequence is provided below:

```
>AAH45610.1 MMP17 protein [Homo sapiens]
                                    (SEQ ID NO: 20)
MRRRAARGPGPPPPGPGLSRLPLLPLPLLLLLALGTRGGCAAPAPAPRAE

DLSLGVEWLSRFGYLPPADPTTGQLQTQEELSKAITAMQQFGGLEATGIL

DEATLALMKTPRCSLPDLPVLTQARRRQAPAPTKWNKRNLSWRVRTFPR

DSPLGHDTVRALMYYALKVWSDIAPLNFHEVAGSTADIQIDFSKANHNDG

YPFDGPGGTVAHAFFPGHHNTAGDTHFDDDEAWTFRSSDAHGMDLFAVAV

HEFGHAIGLSHVAAAHSIMRPYYQGPVGDPLRYGLPYEDKVRVWQLYGVR

ESVSPTAQPEEPPLLPEPPDNRSSAPPRKDVPHRCSTHFDAVAQIRGEAF

FFKGKYFWRLTRDRHLVSLQPAQMHRFWRGLPLHLDSVDAVYERTSDHKI

VFFKGDRYWVFKDNNVEEGYPRPVSDFSLPPGGIDAAFSWAHNDRTYFFK

DQLYWRYDDHTRHMDPGYPAQSPLWRGVPSTLDDAMRWSDGAYYFFRGQE

YWKVLDGELEVAPGYPQSTARDWLVCGDSQADGSVAAGVDAAEGPRAPPG

QHDQSRSEDGYEVCSCTSGASSPPGAPGPLVAATMLLLLPPLSPGALWTA

AQALTL
```

By "SMAD Family Member 3 (SMAD3)" is meant a polypeptide or fragment thereof having at least about 85% amino acid identity to GENBANK Accession No. AAH50743.1. An exemplary polypeptide sequence is provided below:

```
>AAH50743.1 SMAD family member 3 [Homo sapiens]
                                    (SEQ ID NO: 21)
MSSILPFTPPIVKRLLGWKKGEQNGQEEKWCEKAVKSLVKKLKKTGQLDE

LEKAITTQNVNTKCITIPRSLDGRLQVSHRKGLPHVIYCRLWRWPDLHSH

HELRAMELCEFAFNMKKDEVCVNPYHYQRVETPVLPPVLVPRHTEIPAEF

PPLDDYSHSIPENTNFPAGIEPQSNIPETPPPGYLSEDGETSDHQMNHSM

DAGSPNLSPNPMSPAHNNLDLQPVTYCEPAFWCSISYYELNQRVGETFHA

SQPSMTVDGFTDPSNSERFCLGLLSNVNRNAAVELTRRHIGRGVRLYYIG

GEVFAECLSDSAIFVQSPNCNQRYGWHPATVCKIPPGCNLKIFNNQEFAA

LLAQSVNQGFEAVYQLTRMCTIRMSFVKGWGAEYRRQTVTSTPCWIELHL

NGPLQWLDKVLTQMGSPSIRCSSVS
```

By "Vascular endothelial growth factor receptor 2 (VEGFR2 or KDR)" is meant a polypeptide or fragment thereof having at least about 85% amino acid identity to GENBANK Accession No. AAC16450.1. An exemplary polypeptide sequence is provided below:

```
>AAC16450.1 vascular endothelial growth factor
receptor 2 [Homo sapiens]
                                    (SEQ ID NO: 22)
MESKVLLAVALWLCVETRAASVGLPSVSLDLPRLSIQKDILTIKANTTLQ

ITCRGQRDLDWLWPNNQSGSEQRVEVTECSDGLFCKTLTIPKVIGNDTGA

YKCFYRETDLASVIYVYVQDYRSPFIASVSDQHGVVYITENKNKTVVIPC

LGSISNLNVSLCARYPEKRFVPDGNRISWDSKKGFTIPSYMISYAGMVFC

EAKINDESYQSIMYIVVVVGYRIYDVVLSPSHGIELSVGEKLVLNCTART

ELNVGIDFNWEYPSSKHQHKKLVNRDLKTQSGSEMKKFLSTLTIDGVTRS

DQGLYTCAASSGLMTKKNSTFVRVHEKPFVAFGSGMESLVEATVGERVRI

PAKYLGYPPPEIKWYKNGIPLESNHTIKAGHVLTIMEVSERDTGNYTVIL

TNPISKEKQSHVVSLVVYVPPQIGEKSLISPVDSYQYGTTQTLTCTVYAI

PPPHHIHWYWQLEEECANEPSQAVSVTNPYPCEEWRSVEDFQGGNKIEVN

KNQFALIEGKNKTVSTLVIQAANVSALYKCEAVNKVGRGERVISFHVTRG

PEITLQPDMQPTEQESVSLWCTADRSTFENLTWYKLGPQPLPIHVGELPT

PVCKNLDTLWKLNATMFSNSTNDILIMELKNASLQDQGDYVCLAQDRKTK

KRHCVVRQLTVLERVAPTITGNLENQTTSIGESIEVSCTASGNPPPQIMW

FKDNETLVEDSGIVLKDGNRNLTIRRVRKEDEGLYTCQACSVLGCAKVEA

FFIIEGAQEKTNLEIIILVGTAVIAMFFWLLLVIILRTVKRANGGELKTG

YLSIVMDPDELPLDEHCERLPYDASKWEFPRDRLKLGKPLGRGAFGQVIE

ADAFGIDKTATCRTVAVKMLKEGATHSEHRALMSELKILIHIGHHLNVVN

LLGACTKPGGPLMVIVEFCKFGNLSTYLRSKRNEFVPYKTKGARFRQGKD

YVGAIPVDLKRRLDSITSSQSSASSGFVEEKSLSDVEEEEAPEDLYKDFL

TLEHLICYSFQVAKGMEFLASRKCIHRDLAARNILLSEKNVVKICDFGLA

RDIYKDPDYVRKGDARLPLKWMAPETIEDRVYTIQSDVWSFGVLLWEIFS

LGASPYPGVKIDEEFCRRLKEGTRMRAPDYTTPEMYQTMLDCWHGEPSQR
```

-continued

```
PTFSELVEHLGNLLQANAQQDGKDYIVLPISETLSMEEDSGLSLPTSPVS

CMEEEEVCDPKFHYDNTAGISQYLQNSKRKSRPVSVKTFEDIPLEEPEVK

VIPDDNQTDSGMVLASEELKTLEDRTKLSPSFGGMVPSKSRESVASEGSN

QTSGYQSGYHSDDTDTTVYSSEEAELLKLIEIGVOTGSTAQILQPDSGTT

LSSPPV
```

By "Angiopoietin-1 receptor, soluble (also referred to as TEK or Tie-2)" is meant a polypeptide or fragment thereof having at least about 85% amino acid identity to GEN-BANK Accession No. AAA61139.1. An exemplary polypeptide sequence is provided below:

```
>AAA61139.1 receptor protein-tyrosine kinase [Homo
sapiens]
                                    (SEQ ID NO: 23)
MDSLASLVLCGVSLLLSGTVEGAMDLILINSLPLVSDAETSLTCIASGWR

PHEPITIGRDFEALMNQHQDPLEVTQDVTREWAKKVVWKREKASKINGAY

FCEGRVRGEAIRIRTMKMRQQASFLPATLTMTVDKGDNVNISFKKVLIKE

EDAVIYKNGSFIHSVPRHEVPDILEVHLPHAQPQDAGVYSARYIGGNLFT

SAFTRLIVRRCEAQKWGPECNHLCTACMNNGVCHEDTGECICPPGFMGRT

CEKACELHTFGRTCKERCSGOEGCKSYVFCLPDPYGCSCATGWKGLQCNE

ACHPGFYGPDCKLRCSCNNGEMCDRFQGCLCSPGWQGLQCEREGIPRMTP

KIVDLPDHIEVNSGKFNPICKASGWPLPTNEEMTLVKPDGTVLHPKDFNH

TDHFSVAIFTIHRILPPDSGVWVCSVNTVAGMVEKPFNISVKVLPKPLNA

PNVIDTGHNFAVINISSEPYFGDGPIKSKKLLYKPVNHYEAWQHIQVTNE

IVTLNYLEPRTEYELCVQLVRRGEGGEGHPGPVRRFTTASIGLPPPRGLN

LLPKSQTTLNLTWQPIFPSSEDDFYVEVERRSVQKSDQQNIKVPGNLTSV

LLNNLHPREQYVVRARVNTKAQGEWSEDLTAWTLSDILPPQPENIKISNI

THSSAVISWTILDGYSISSITIRYKVQGKNEDQHVDVKIKNATIIQYQLK

GLEPETAYQVDIFAENNIGSSNPAFSHELVTLPESQAPADLGGGKMLLIA

ILGSAGMTCLTVLLAFLIILQLKRANVQRRMAQAFQNVREEPAVQFNSGT

LALNRKVKNNPDPTIYPVLDWNDIKFQDVIGEGNFGQVLKARIKKDGLRM

DAAIKRMKEYASKDDHRDFAGELEVLCKLGHHPNIINLLGACEHRGYLYL

AIEYAPHGNLLDFLRKSRVLETDPAFAIANSTASTLSSQQLLHFAADVAR

GMDYLSQKQFIHRDLAARNILVGENYVAKIADFGLSRGQEVYVKKTMGRL

PVRWMAIESLNYSVYTTNSDVWSYGVLLWEIVSLGGTPYCGMTCAELYEK

LPQGYRLEKPLNCDDEVYDLMRQCWREKPYERPSFAQILVSLNRMLEERK

TYVNTTLYEKFTYAGIDCSAEEAA
```

By "Cadherin-5 (CDH5)" is meant a polypeptide or fragment thereof having at least about 85% amino acid identity to GENBANK Accession No. AAH96364.3. An exemplary polypeptide sequence is provided below:

```
>AAH96364.3 CDH5 protein [Homo sapiens]
                                    (SEQ ID NO: 24)
MQRLMMLLATSGACLGLLAVAAVAAAGANPAQRDTHSLLPTHRRQKRDWI

WNQMHIDEEKNTSLPHHVGKIKSSVSRKNAKYLLKGEYVGKVFRVDAETG
```

```
DVFAIERLDRENISEYHLTAVIVDKDTGENLETPSSFTIKVHDVNDNWPV

FTHRLFNASVPESSAVGTSVISVTAVDADDPTVGDHASVMYQILKGKEYF

AIDNSGRIITITKSLDREKQARYEIVVEARDAQGLRGDSGTATVLVTLQD

INDNFPFFTQTKYTFVVPEDTRVGTSVGSLFVEDPDEPQNRMTKYSILRG

DYQDAFTIETNPAHNEGIIKPMKPLDYEYIQQYSFIVEATDPTIDLRYMS

PPAGNRAQVIINITDVDEPPIFQQPFYHFQLVLQISAIDKDITPRNVKFK

FTLNTENNFTLTDNHDNTANITVKYGQFDREHTKVHFLPVVISDNGMPSR

TGTSTLTVAVCKCNEQGEFTFCEDMAAQVGVSIQAVVAILLCILTITVIT

LLIFLRRRLRKQARAHGKSVPEIHEQLVTYDEEGGGEMDTTSYDVSVLNS

VRRGGAKPPRPALDARPSLYAQVQKPPRHAPGAHGGPGEMAAMIEVKKDE

ADHDGDGPPYDTLHIYGYEGSESIAESLSSLGTDSSDSDVDYDFLNDWGP

RFKMLAELYGSDPREELLY
```

By "Neurogenic locus notch homolog protein 1 (NOTCH1)" is meant a polypeptide or fragment thereof having at least about 85% amino acid identity to GEN-BANK Accession No. AAG33848.1. An exemplary polypeptide sequence is provided below:

```
>AAG33848.1 NOTCH 1 [Homo sapiens]
                                    (SEQ ID NO: 25)
MPPLLAPLLCLALLPALAARGPRCSQPGETCLNGGKCEAANGTEACVCGG

AFVGPRCQDPNPCLSTPCKNAGTCHVVDRRGVADYACSCALGFSGPLCLT

PLDNACLTNPCRNGGTCDLLTLTEYKCRCPPGWSGKSCQQADPCASNPCA

NGGQCLPFEASYICHCPPSFHGPTCRQDVNECGQKPRLCRHGGTCHNEVG

SYRCVCRATHTGPNCERPYVPCSPSPCQNGGTCRPTGDVTHECACLPGFT

GQNCEENIDDCPGNNCKNGGACVDGVNTYNCPCPPEWTGQYCTEDVDECQ

LMPNACQNGGTCHNTHGGYNCVCVNGWTGEDCSENIDDCASAACFHGATC

HDRVASFYCECPHGRTGLLCHLNDACISNPCNEGSNCDTNPVNGKAICTC

PSGYTGPACSQDVDECSLGANPCEHAGKCINTLGSFECQCLQGYTGPRCE

IDVNECVSNPCQNDATCLDQIGEFQCMCMPGYEGVHCEVNTDECASSPCL

HNGRCLDKINEFQCECPTGFTGHLCQYDVDECASTPCKNGAKCLDGPNTY

TCVCTEGYTGTHCEVDIDECDPDPCHYGSCKDGVATFTCLCRPGYTGHHC

ETNINECSSQPCRLRGTCQDPDNAYLCFCLKGTTGPNCEINLDDCASSPC

DSGTCLDKIDGYECACEPGYTGSMCNSNIDECAGNPCHNGGTCEDGINGF

TCRCPEGYHDPTCLSEVNECNSNPCVHGACRDSLNGYKCDCDPGWSGTNC

DINNNECESNPCVNGGTCKDMTSGIVCTCREGFSGPNCQTNINECASNPC

LNKGTCIDDVAGYKCNCLLPYTGATCEVVLAPCAPSPCRNGGECRQSEDY

ESFSCVCPTAGAKGQTCEVDINECVLSPCRHGASCQNTHGXYRCHCQAGY

SGRNCETDIDDCRPNPCHNGGSCTDGINTAFCDCLPGFRGTFCEEDINEC

ASDPCRNGANCTDCVDSYTCTCPAGFSGIHCENNTPDCTESSCFNGGTCV

DGINSFTCLCPPGFTGSYCQHVVNECDSRPCLLGGTCQDGRGLHRCTCPQ

GYTGPNCQNLVHWCDSSPCKNGGKCWQTHTQYRCECPSGWTGLYCDVPSV

SCEVAAQRQGVDVARLCQHGGLCVDAGNTHHCRCQAGYTGSYCEDLVDEC
```

-continued

SPSPCQNGATCTDYLGGYSCKCVAGYHGVNCSEEIDECLSHPCQNGGTCL

DLPNTYKCSCPRGTQGVHCEINVDDCNPPVDPVSRSPKCFNNGTCVDQVG

GYSCTCPPGFVGERCEGDVNECLSNPCDARGTQNCVQRVNDFHCECRAGH

TGRRCESVINGCKGKPCKNGGTCAVASNTARGFICKCPAGFEGATCENDA

RTCGSLRCLNGGTCISGPRSPTCLCLGPFTGPECQFPASSPCLGGNPCYN

QGTCEPTSESPFYRCLCPAKFNGLLCHILDYSFGGGAGRDIPPPLIEEAC

ELPECQEDAGNKVCSLQCNNHACGWDGGDCSLNFNDPWKNCTQSLQCWKY

FSDGHCDSQCNSAGCLFDGFDCQRAEGQCNPLYDQYCKDHFSDGHCDQGC

NSAECEWDGLDCAEHVPERLAAGTLVVVVLMPPEQLRNSSFHFLRELSRV

LHTNVVFKRDAHGQQMIFPYYGREEELRKHPIKRAAEGWAAPDALLGQVK

ASLLPGGSEGGRRRRELDPMDVRGSIVYLEIDNRQCVQASSQCFQSATDV

AAFLGALASLGSLNIPYKIEAVQSETVEPPPPAQLHFMYVAAAAFVLLFF

VGCGVLLSRKRRRQHGQLWFPEGFKVSEASKKKRREPLGEDSVGLKPLKN

ASDGALMDDNQNEWGDEDLETKKFRFEEPVVLPDLDDQTDHRQWTQQHLD

AADLRMSAMAPTPPQGEVDADCMDVNVRGPDGFTPLMIASCSGGGLETGN

SEEEEDAPAVISDFIYQGASLHNQTDRTGETALHLAARYSRSDAAKRLLE

ASADANIQDNMGRTPLHAAVSADAQGVFQILIRNRATDLDARMHDGTTPL

ILAARLAVEGMLEDLINSHADVNAVDDLGKSALHWAAAVNNVDAAVVLLK

NGANKDMQNNREETPLFLAAREGSYETAKVLLDHFANRDITDHMDRLPRD

IAQERMHHDIVRLLDEYNLVRSPQLHGAPLGGTPTLSPPLCSPNGYLGSL

KPGVQGKKVRKPSSKGLACGSKEAKDLKARRKKSQDGKGCLLDSSGMLSP

VDSLESPHGYLSDVASPPLLPSPFQQSPSVPLNHLPGMPDTHLGIGHLNV

AAKPEMAALGGGGRLAFETGPPRLSHLPVASGTSTVLGSSSGGALNFTVG

GSTSLNGQCEWLSRLQSGMVPNQYNPLRGSVAPGPLSTQAPSLQHGMVGP

LHSSLAASALSQMMSYQGLPSTRLATQPHLVQTQQVQPQNLQMQQQNLQP

ANIQQQQSLQPPPPPPQPHLGVSSAASGHLGRSFLSGEPSQADVQPLGPS

SLAVHTILPQESPALPTSLPSSLVPPVTAAQFLTPPSQHSYSSPVDNTPS

HQLQVPEHPFLTPSPESPDQWSSSSPHSNVSDWSEGVSSPPTSMQSQIAR

IPEAFK

By "Lymphotoxin alpha2: beta1 (LTA LTB)" is meant a complex comprising polypeptides or fragments thereof having at least about 85% amino acid identity to GENBANK Accession No. AQY76900.1 (LTA) and AQY76901.1 (LTB). Exemplary polypeptide sequences are provided below:

LTA:
>AQY76900.1 LTA [Homo sapiens]

(SEQ ID NO: 26)

MTPPERLFLPRVRGTTLHLLLLGLLLVLLPGAQGLPGVGLTPSAAQTARQ

PPKMHLAHSTLKPAAHLIGDPSKQNSLLWRANTDRAFLQDGFSLSNNSLL

VPTSGIYFVYSQVVFSGKAYSPKATSSPLYLAHEVQLFSSQYPFHVPLLS

SQKMVYPGLQEPWLHSMYHGAAFQLTQGDQLSTHTDGIPHLVLSPSTVFF

GAFAL

-continued

LTB: AQY76901.1

(SEQ ID NO: 27)

MGALGLEGRGGRLQGRGSLLLAVAGATSLVTLLLAVPITVLAVLALVPQD

QGGLVTETADPGAQAQQGLGFQKLPEEEPETDLSPGLPAAHLIGAPLKGQ

GLGWETTKEQAFLTSGTQFSDAEGLALPQDGLYYLYCLVGYRGRAPPGGG

DPQGRSVTLRSSLYRAGGAYGPGTPELLLEGAETVTPVLDPARRQGYGPL

WYTSVGFGGLVQLRRGERVYVNISHPDMVDFARGKTFFGAVMVG

By "A disintegrin and metalloproteinase with thrombospondin motifs 13 (ADAMTS13)" is meant a polypeptide or fragment thereof having at least about 85% amino acid identity to GENBANK Accession No. ABD72606.1. An exemplary polypeptide sequence is provided below:

>ABD72606.1 ADAM metallopeptidase with thrombo-
spondin type 1 motif, 13 [Homo sapiens]

(SEQ ID NO: 28)

MHQRHPRARCPPLCVAGILACGFLLGCWGPSHFQQSCLQALEPQAVSSYL

SPGAPLKGRPPSPGFQRQRQRQRRAAGGILHLELLVAVGPDVFQAHQEDT

ERYVLTNLNIGAELLRDPSLGAQFRVHLVKMVILTEPEGAPNITANLTSS

LLSVCGWSQTINPEDDTDPGHADLVLYITRFDLELPDGNRQVRGVTQLGG

ACSPTWSCLITEDTGFDLGVTIAHEIGHSFGLEHDGAPGSGCGPSGHVMA

SDGAAPRAGLAWSPCSRRQLLSLLSAGRARCVWDPPRPQPGSAGHPPDAQ

PGLYYSANEQCRVAFGPKAVACTFAREHLDMCQALSCHTDPLDQSSCSRL

LVPLLDGTECGVEKWCSKGRCRSLVELTPIAAVHGRWSSWGPRSPCSRSC

GGGVVTRRRQCNNPRPAFGGRACVGADLQAEMCNTQACEKTQLEFMSQQC

ARTDGQPLRSSPGGASFYHWGAAVPHSQGDALCRHMCRAIGESFIMKRGD

SFLDGTRCMPSGPREDGTLSLCVSGSCRTFGCDGRMDSQQVWDRCQVCGG

DNSTCSPRKGSFTAGRAREYVTFLTVTPNLTSVYIANHRPLFTHLAVRIG

GRYVVAGKMSISPNTTYPSLLEDGRVEYRVALTEDRLPRLEEIRIWGPLQ

EDADIQVYRRYGEEYGNLTRPDITFTYFQPKPRQAWVWAAVRGPCSVSCG

AGLRWVNYSCLDQARKELVETVQCQGSQQPPAWPEACVLEPCPPYWAVGD

FGPCSASCGGGLRERPVRCVEAQGSLLKTLPPARCRAGAQQPAVALETCN

PQPCPARWEVSEPSSCTSAGGAGLALENETCVPGADGLEAPVTEGPGSVD

EKLPAPEPCVGMSCPPGWGHLDATSAGEKAPSPWGSIRTGAQAAHVWTPA

AGSCSVSCGRGLMELRFLCMDSALRVPVQEELCGLASKPGSRREVCQAVP

CPARWQYKLAACSVSCGRGVVRRILYCARAHGEDDGEEILLDTQCQGLPR

PEPQEACSLEPCPPRWKVMSLGPCSASCGLGTARRSVACVQLDQGQDVEV

DEAACAALVRPEASVPCLIADCTYRWHVGTWMECSVSCGDGIQRRRDTCL

GPQAQAPVPADFCQHLPKPVTVRGCWAGPCVGQGTPSLVPHEEAAAPGRT

TATPAGASLEWSQARGLLFSPAPQPRRLLPGPQENSVQSSACGRQHLEPT

GTIDMRGPGQADCAVAIGRPLGEVVTLRVLESSLNCSAGDMLLLWGRLTW

RKMCRKLLDMTFSSKTNTLVVRQRCGRPGGGVLLRYGSQLAPETFYRECD

-continued

-continued

MQLFGPWGEIVSPSLSPATSNAGGCRLFINVAPHARIAIHALATNMGAGT

EGANASYILIRDTHSLRTTAFHGQQVLYWESESSQAEMEFSEGFLKAQAS

LRGQYWTLQSWVPEMQDPQSWKGKEGT

By "Repulsive guidance molecule A (RGMA)" is meant a polypeptide or fragment thereof having at least about 85% amino acid identity to GENBANK Accession No. AAI51133.1. An exemplary polypeptide sequence is provided below:

>AAI51133.1 RGM domain family, member A [*Homo sapiens*]
(SEQ ID NO: 29)
MQPPRERLVVTGRAGWMGMGRGAGRSALGFWPTLAFLLCSFPAATSPCKI

LKCNSEFWSATSGSHAPASDDTPEFCAALRSYALCTRRTARTCRGDLAYH

SAVHGIEDLMSQHNCSKDGPTSQPRLRTLPPAGDSQERSDSPEICHYEKS

FHKHSATPNYTHCGLFGDPHLRTFTDRFQTCKVQGAWPLIDNNYLNVQVT

NTPVLPGSAATATSKLTIIFKNFQECVDQKVYQAEMDELPAAFVDGSKNG

GDKHGANSLKITEKVSGQHVEIQAKYIGTTIVVRQVGRYLTFAVRMPEEV

VNAVEDWDSQGLYLCLRGCPLNQQIDFQAFHTNAEGTGARRLAAASPAPT

APETFPYETAVAKCKEKLPVEDLYYQACVFDLLTTGDVNFTLAAYYALED

VKMLHSNKDKLHLYERTRDLPGRAAAGLPLAPRPLLGALVPLLALLPVFC

By "Antithrombin-III (SERPINC1)" is meant a polypeptide or fragment thereof having at least about 85% amino acid identity to GENBANK Accession No. AAA51796.1. An exemplary polypeptide sequence is provided below:

>AAA51796.1 antithrombin III [*Homo sapiens*]
(SEQ ID NO: 30)
MYSNVIGTVTSGKRKVYLLSLLLIGFWDCVTCHGSPVDICTAKPRDIPMN

PMCIYRSPEKKATEDEGSEQKIPEATNRRVWELSKANSRFATTFYQHLAD

SKNDNDNIFLSPLSISTAFAMTKLGACNDTLQQLMEVFKEDTISEKTSDQ

IHFFFAKLNCRLYRKANKSSKLVSANRLFGDKSLTFNETYQDISELVYGA

KLQPLDFKENAEQSRAAINKWVSNKTEGRITDVIPSEAINELTVLVLVNT

IYFKGLWKSKFSPENTRKELFYKADGESCSASMMYQEGKFRYRRVAEGTQ

VLELPFKGDDITMVLILPKPEKSLAKVEKELTPEVLQEWLDELEEMMLVV

HMPRFRIEDGFSLKEQLQDMGLVDLFSPEKSKLPGIVAEGRDDLYVSDAF

HKAFLEVNEEGSEAAASTAVVIAGRSLNPNRVTFKANRLFLVFIREVPLN

TIIFMGRVANPCVK

By "A disintegrin and metalloproteinase with thrombospondin motifs 1 (ADAMTS1)" is meant a polypeptide or fragment thereof having at least about 85% amino acid identity to GENBANK Accession No. AAH36515.1. An exemplary polypeptide sequence is provided below:

>AAH36515.1 ADAM metallopeptidase with thrombospondin type 1 motif, 1 [*Homo sapiens*]
(SEQ ID NO: 31)
MQRAVPEGFGRRKLGSDMGNAERAPGSRSFGPVPTLLLLAAALLAVSDAL

GRPSEEDEELVVPELERAPGHGTTRLRLHAFDQQLDLELRPDSSFLAPGF

TLQNVGRKSGSETPLPETDLAHCFYSGTVNGDPSSAAALSLCEGVRGAFY

LLGEAYFIQPLPAASERLATAAPGEKPPAPLQFHLLRRNRQGDVGGTCGV

VDDEPRPTGKAETEDEDEGTEGEDEGPQWSPQDPALQGVGQPTGTGSIRK

KRFVSSHRYVETMLVADQSMAEFHGSGLKHYLLTLFSVAARLYKHPSIRN

SVSLVVVKILVIHDEQKGPEVTSNAALTLRNFCNWQKQHNPPSDRDAEHY

DTAILFTRQDLCGSQTCDTLGMADVGTVCDPSRSCSVIEDDGLQAAFTTA

HELGHVFNMPHDDAKQCASLNGVNQDSHMMASMLSNLDHSQPWSPCSAYM

ITSFLDNGHGECLMDKPQNPIQLPGDLPGTSYDANRQCQFTFGEDSKHCP

DAASTCSTLWCTGTSGGVLVCQTKHFPWADGTSCGEGKWCINGKCVNKTD

RKHFDTPFHGSWGMWGPWGDCSRTCGGGVQYTMRECDNPVPKNGGKYCEG

KRVRYRSCNLEDCPDNNGKTFREEQCEAHNEFSKASFGSGPAVEWIPKYA

GVSPKDRCKLICQAKGIGYFFVLQPKVVDGTPCSTDSTSVCVQGQCVKAG

CDRIIDSKKKFDKCGVCGGNGSTCKKISGSVTSAKPGYHDIITIPTGATN

IEVKQRNQRGSRNNGSFLAIKAADGTYILNGDYTLSTLEQDIMYKGVVLR

YSGSSAALERIRSFSPLKEPLTIQVLTVGNALRPKIKYTYFVKKKKESFN

AIPTFSAWVIEEWGECSKSCELGWQRRLVECRDINGQPASECAKEVKPAS

TRPCADHPCPQWQLGEWSSCSKTCGKGYKKRSLKCLSHDGGVLSHESCDP

LKKPKHFIDFCTMAECS

By "Plasminogen activator inhibitor 1 (SERPINE1)" is meant a polypeptide or fragment thereof having at least about 85% amino acid identity to GENBANK Accession No. AAK60338.1. An exemplary polypeptide sequence is provided below:

>AAK60338.1 serine-cysteine proteinase inhibitor clade E member 1 [*Homo sapiens*]
(SEQ ID NO: 32)
MQMSPALTCLVLGLALVFGEGSAVHHPPSYVAHLASDFGVRVFQQVAQAS

KDRNVVFSPYGVASVLAMLQLTTGGETQQQIQAAMGFKIDDKGMAPALRH

LYKELMGPWNKDEISTTDAIFVQRDLKLVQGFMPHFFRLFRSTVKQVDFS

EVERARFIINDWVKTHTKGMISNLLGKGAVDQLTRLVLVNALYFNGQWKT

PFPDSSTHRRLFHKSDGSTVSVPMMAQTNKFNYTEFTTPDGHYYDILELP

YHGDTLSMFIAAPYEKEVPLSALTNILSAQLISHWKGNMTRLPRLLVLPK

FSLETEVDLRKPLENLGMTDMFRQFQADFTSLSDQEPLHVAQALQKVKIE

VNESGTVASSSTAVIVSARMAPEEIIMDRPFLFVVRHNPTGTVLFMGQVM

EP

By "Metalloproteinase inhibitor 3 (TIMP3)" is meant a polypeptide or fragment thereof having at least about 85% amino acid identity to GENBANK Accession No. AAH14277.1. An exemplary polypeptide sequence is provided below:

>AAH14277.1 TIMP metallopeptidase inhibitor 3 [*Homo sapiens*]
(SEQ ID NO: 33)
MTPWLGLIVLLGSWSLGDWGAEACTCSPSHPQDAFCNSDIVIRAKVVGKK

LVKEGPFGTLVYTIKQMKMYRGFTKMPHVQYIHTEASESLCGLKLEVNKY

-continued

QYLLTGRVYDGKMYTGLCNFVERWDQLTLSQRKGLNYRYHLGCNCKIKSC

YYLPCFVTSKNECLWTDMLSNFGYPGYQSKHYACIRQKGGYCSWYRGWAP

PDKSIINATDP

By "Platelet factor 4 (PF4)" is meant a polypeptide or fragment thereof having at least about 85% amino acid identity to GENBANK Accession No. AAH93965.1. An exemplary polypeptide sequence is provided below:

>AAH93965.1 Platelet factor 4 [Homo sapiens]
(SEQ ID NO: 34)
MSSAAGFCASRPGLLFLGLLLLPLVVAFASAEAEEDGDLQCLCVKTTSQV

RPRHITSLEVIKAGPHCPTAQLIATLKNGRKICLDLQAPLYKKIIKKLLE

S

Also included in this disclosure are the polynucleotides encoding any of the aforementioned polypeptide biomarkers or any other biomarker described herein.

By "biomarker profile" or "marker profile" is meant a characterization of the expression or expression level of two or more polypeptides or polynucleotides.

By "capture reagent" is meant a reagent that specifically binds a nucleic acid molecule or polypeptide to select or isolate the nucleic acid molecule or polypeptide.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the terms "determining," "assessing," "assaying," "measuring," and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include any disease, condition, or disorder in the placenta accreta spectrum (e.g., placenta increta, placenta percreta, and placenta accreta).

By "placenta accreta spectrum" is meant a group of disorders, for example, placenta increta, placenta percreta, and placenta accreta, characterized by pathologic adherence of the placenta to the uterine wall.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen, or reversed Hoogsteen hydrogen bonding, between complementary nucleobases. For example, adenine and thymine are complementary nucleobases that pair through the formation of hydrogen bonds.

By "Ingenuity Pathway Analysis" is meant a software application that enables analysis of biological data from gene expression, metabolomics and proteomics experiments. For example, upstream regulatory analysis using this software helps identify molecules upstream of genes in the dataset that potentially explain the observed expression changes.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis. As used herein, "obtaining" as in "obtaining an agent" includes synthesizing, purchasing, or otherwise acquiring the agent.

By "principal component analysis" or "PCA" is meant an unsupervised learning method to find patterns without reference to prior knowledge in biological samples from different groups. PCA searches for a linear combination of the initial variables, extracting their maximum variance as the first principal component. After removal of this first variance, PCA derives additional linear combinations of variables which are visualized in 2D or 3D PCA maps based on distances or similarities between the different samples. Each principal component (or eigenvalue) captures a certain percentage of the total variance, with typically the first 2-3 components capturing a high percentage of the variance.

By "proteomics" is meant a large-scale study of proteins in a biological context. The most common methods used to study proteomics in biological fluids include mass-spectrometry based or antibody-based microarray approach. Aptamer based proteomics is a relatively newer proteomics platform that uses SOMAmers (Slow Off--rate Modified Aptamers), modified DNA aptamers, which are oligonucleotides that bind with high specificity to pre-selected proteins. SOMAscan simultaneously quantifies about 1400 human proteins in plasma by transforming each individual protein concentration into a corresponding SOMAmer concentration, which is then quantified using a DNA microarray read-out.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, at least about 20 amino acids, at least about 25 amino acids, or about 35 amino acids, about 50 amino acids, or about 100 amino acids. For nucleic acids, the length of the reference nucleic acid sequence will generally be at least about 50 nucleotides, at least about 60 nucleotides, at least about 75 nucleotides, or about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide. Stringent temperature conditions will ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In an embodiment, hybridization will occur at 30° C. in 750 mM NaCl, 75 mM trisodium citrate, and 1% SDS. In an embodiment, hybridization will occur at 37° C. in 500 mM NaCl, 50 mM trisodium citrate, 1% SDS, 35% formamide, and 100 μg/ml denatured salmon sperm DNA (ssDNA). In another embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, in some embodiments, stringent salt concentration for the wash steps will be less than about 30 mM NaCl and 3 mM trisodium citrate or less than about 15 mM NaCl and 1.5 mM trisodium citrate. Stringent temperature conditions for the wash steps will ordinarily include a temperature of at least about 25° C., at least about 42° C., or at least about 68° C. In an embodiment, wash steps will occur at 25° C. in 30 mM NaCl, 3 mM trisodium citrate, and 0.1% SDS. In another embodiment, wash steps will occur at 42 C in 15 mM NaCl, 1.5 mM trisodium citrate, and 0.1% SDS. In another embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). In some embodiments, such a sequence is at least 60%, 80%, 85%, 90%, 95%, or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, iso-leucine, leucine; aspartic acid, glutamic acid, asparagine, glutamine; serine, threonine; lysine, arginine; and phenyl-alanine, tyrosine. In an exemplary approach to determining the degree of identity, a BLAST program may be used, with a probability score between $e^{-3}$ and $e^{-100}$ indicating a closely related sequence.

By "subject" is a human or a non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a heat map depicting plasma protein expression that reflects relative minimum and maximum expression levels for each protein as quantified by SOMAscan®. Comparisons were made between all third trimester PAS cases and controls. FIG. 1B is a heat map depicting plasma protein expression in third trimester PAS cases and controls restricted to participants with placenta previa. SERPINE1 (or PAI-1), previously reported to be altered in PAS, is indicated by the arrow in FIGS. 1A and 1B.

FIG. 3A is a dot plot summarizing the Principal Component Analysis using all 1305 of the SOMAscan assay to identify potential markers that can be used to discriminate between PAS cases and controls (p<0.01) using the two first principal components. FIG. 3B is a dot plot summarizing the Principal Component Analysis using the top 21 proteins that can be used to discriminate between PAS cases and controls (p<0.01) using the two first principal components.

FIG. 5A comprises dot plots of anti-thrombin III and SERPINE1 expression levels as determined by SOMAscan® and ELISA in PAS controls and cases. FIG. 5B comprises dot plots of soluble VEGFR2 and soluble TEK expression levels as determined by SOMAscan® and ELISA in PAS cases and controls are depicted. The left panels for both figures show the relative fluorescence units from the SOMAscan®, and the right panels of both figures show the corresponding ELISA data for the same samples. Mean expression is depicted as "+", and median expression is indicated by a horizontal line.

DETAILED DESCRIPTION OF THE INVENTION

Figure 1A:
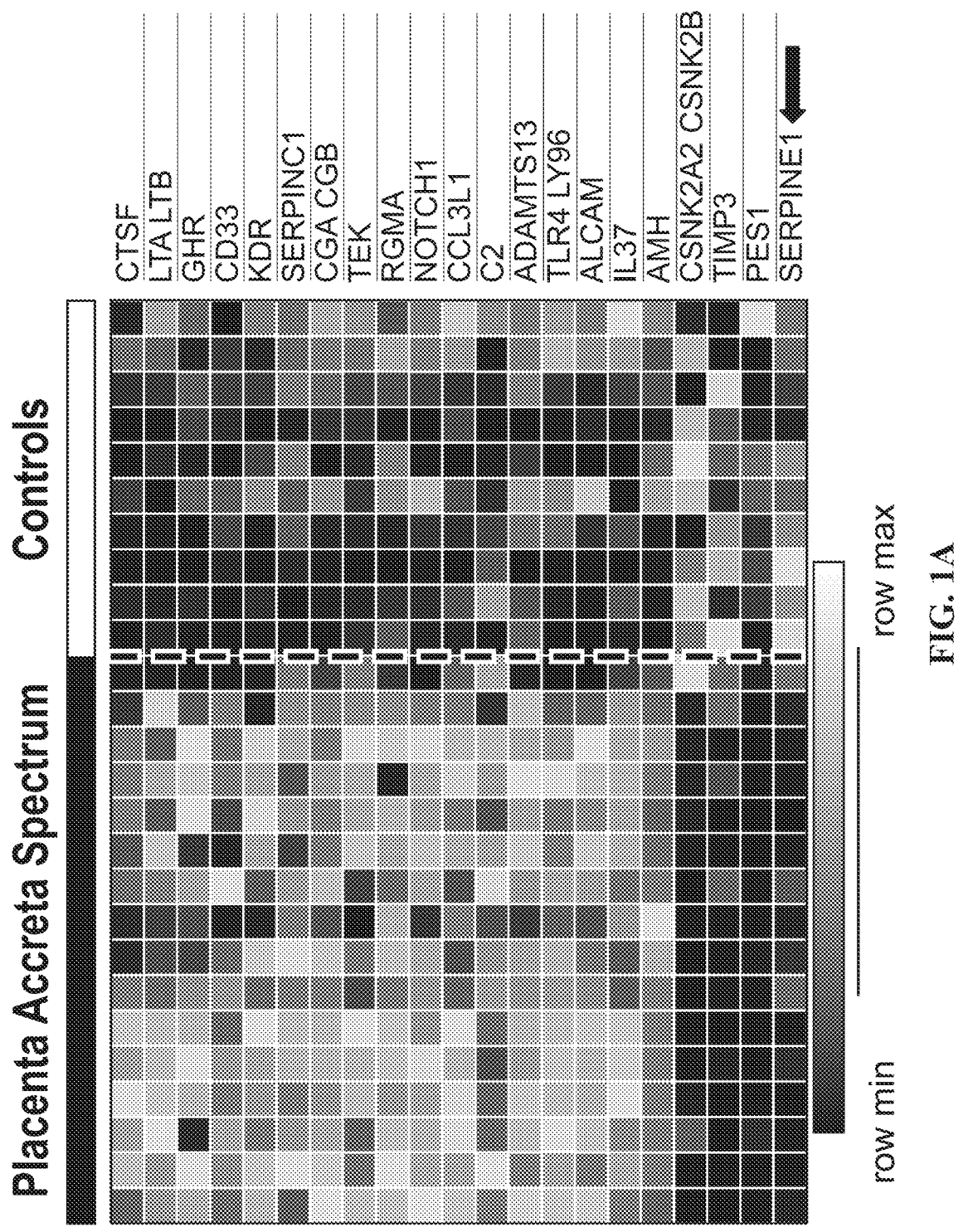
FIGS. 1A and 1B illustrate differential protein expression between subjects in their third trimesters with placenta accreta spectrum (PAS) and controls.

The invention features compositions and methods that are useful for detecting placenta accretion spectrum (PAS). More specifically, the invention features panels of biomarkers and the use of such panels for detecting and characterizing PAS.

The invention is based, at least in part, on the discovery of circulating proteins with altered expression in the plasma of women with placenta accreta spectrum. Four dysregulated proteins (antithrombin III, plasminogen activator inhibitor 1, soluble Tie2 and soluble VEGF receptor 2) were confirmed with enzyme linked immunosorbent assay. Despite the heterogeneity of PAS, a clear separation was surprisingly observed between cases and controls. Accordingly, such markers, as well as the others described herein, can be assayed to identify pregnant women having or at risk of developing PAS.

As reported in detail below, plasma samples were obtained prior to delivery from sixteen participants with PAS and ten controls with similar gestational ages. Plasma samples were analyzed by SOMAscan®, an aptamer-based proteomics platform, for alterations in 1,305 unique proteins. Heat maps of the most differentially-expressed proteins were generated with Morpheus (Broad Institute, Cambridge, MA). Principal component analysis was performed using the top 21 dysregulated proteins. Dysregulated proteins were confirmed using enzyme-linked immunosorbent assay (ELISA).

Many of the top 50 proteins significantly dysregulated in participants with PAS were inflammatory cytokines, factors regulating vascular remodeling, and extracellular matrix proteins regulating invasion. PCA using the top 21 proteins distinctly separated the PAS cases from controls (P<0.01). Using ELISA, 4 proteins were confirmed that were dysregulated in PAS cases compared with controls: antithrombin III (240.4 mg/ml vs 150.3 mg/ml, P=0.002), plasminogen activator inhibitor 1 (4.1 ng/ml vs 7.1 ng/ml, P<0.001), soluble Tie2 (13.5 ng/ml vs 10.4 ng/ml, P=0.02), soluble VEGF receptor 2 (9.0 ng/ml vs 5.9 ng/ml, P=0.003). Subjects with PAS had a unique and distinct plasma protein signature in the second and third trimesters.

Accordingly, the invention provides panels of biomarkers for PAS that can be used as novel diagnostic, detection, and prognostic tools. For example, PAS can be detected in the second or third trimesters by assaying all or a subset of the biomarkers in Tables 1B and 1A, respectively.

The invention provides panels of biomarkers for identifying women who have or are at risk of developing PAS during their third trimester comprising the following set of markers: Complement component C8 (C8A C8B C8G), Apolipoprotein M (APOM), WAP, kazal, immunoglobulin, kunitz and NTR domain-containing protein 1 (WFIKKN1), Growth hormone receptor (GHR), Human Chorionic Gonadotropin (CGA CGB), Myeloid cell surface antigen CD33 (CD33), Vascular endothelial growth factor receptor 2 (KDR), Interleukin-18 receptor 1 (IL18R1), Reticulon-4 receptor (RTN4R), Angiopoietin-1 receptor, soluble (TEK), Secreted frizzled-related protein 3 (FRZB), Toll-like receptor 4: Lymphocyte antigen 96 complex (TLR4 LY96), Cathepsin F (CTSF), Interleukin-37 (IL37), Muellerian-inhibiting factor (AMH), CD166 antigen (ALCAM), Mediator of RNA polymerase II transcription subunit 1 (MED1), Ubiquitin-conjugating enzyme E2 G2 (UBE2G2), Interleukin-13 receptor subunit alpha-1 (IL13RA1), Immunoglobulin superfamily containing leucine-rich repeat protein 2 (ISLR2), Cadherin-5 (CDH5), Neurogenic locus notch homolog protein 1 (NOTCH1), C-C motif chemokine 3-like 1 (CCL3L1), Tumor necrosis factor receptor superfamily member 21 (TNFRSF21), Lymphotoxin alpha2: beta1 (LTA LTB), Epidermal growth factor receptor (EGFR), A disintegrin and metalloproteinase with thrombospondin motifs 13 (ADAMTS13), Carbonic anhydrase-related protein 10 (CA10), Ectodysplasin-A, secreted form (EDA), Neural cell adhesion molecule L1-like protein (CHL1), Repulsive guidance molecule A (RGMA), Sphingosine kinase 2 (SPHK2), Endothelin-converting enzyme 1 (ECE1), Complement C2 (C2), Interleukin-1 Receptor accessory protein (IL1RAP), Alpha-2-antiplasmin (SERPINF2), Antithrombin-III (SERPINC1), Gremlin-1 (GREM1), A disintegrin and metalloproteinase with thrombospondin motifs 1 (ADAMTS1), Calcium/calmodulin-dependent protein kinase kinase 1 (CAMKK1), Plasminogen activator inhibitor 1 (SERPINE1), Cryptic protein (CFC1), Cadherin-12 (CDH12), DnaJ homolog subfamily B member 1 (DNAJB1), Pescadillo homolog (PES1), Metalloproteinase inhibitor 3 (TIMP3), L-lactate dehydrogenase B chain (LDHB), Casein kinase II 2-alpha': 2-beta heterotetramer (CSNK2A2 CSNK2B), Peroxiredoxin-6 (PRDX6), and Platelet factor 4 (PF4).

In some embodiments, a panel of third trimester PAS biomarkers comprises CTSF, LTA LTB, GHR, CD33, KDR, SERPINC1, CGA CGB, TEK, RGMA, NOTCH1, CCL3L1, C2, ADAMTS13, TLR4 LY96, ALCAM, IL37, AMH, CSNK2A2 CSNK2B, TIMP3, PES1, and SERPINE1. In some embodiments, the panel of third trimester PAS biomarkers comprise SERPINC1, SERPINE1, TEK, and KDR. In some embodiments, the panel of third trimester PAS biomarkers comprise LTA/LTB, SERPINC1, and SERPINE1. In some embodiments, the panel of third trimester PAS biomarkers comprise KDR, CD33, IL37, and TEK. In some embodiments, the panel of third trimester PAS biomarkers comprise ADAMTS13, TIMP3, CTSF, and AMH. In some embodiments, the panel of third trimester PAS biomarkers comprise LTA/LTB, SERPINC1, SERPINE1, KDR, CD33, IL37, TEK, ADAMTS13, TIMP3, CTSF, and AMH.

In some embodiments, a panel of second trimester PAS biomarkers comprises Anti-Mullerian Hormone (AMH), CD5 Molecule Like (CD5L), Interleukin 7 Receptor (IL7R), Matrix Metallopeptidase 17 (MMP17), Complement C9 (C9), Chitinase 3 Like 1 (CHI3L1), Endothelial Cell Specific Molecule 1 (ESM1), GDNF Family Receptor Alpha 3 (GFRA3), Plasminogen Activator, Tissue Type (PLAT), S100 Calcium Binding Protein A7 (S100A7), Colony Stimulating Factor 1 Receptor (CSF1R), Ephrin A2 (EFNA2), Dermatopontin (DPT), Delta Like Canonical Notch Ligand 1 (DLL1), Interleukin 5 Receptor Subunit Alpha (IL5RA), Lymphocyte Activating 3 (LAG3), Follistatin Like 3 (FSTL3), Fibroblast Growth Factor 5 (FGF5), SPARC (Osteonectin, Cwcv And Kazal Like Domains Proteoglycan 2 (SPOCK2), Laminin Subunit Alpha 1 (LAMAI Laminin Subunit Beta 1 (LAMB1 Laminin Subunit Gamma 1 (LAMC1), Kirre Like Nephrin Family Adhesion Molecule 3 (KIRREL3), Calcium/Calmodulin Dependent Protein Kinase I (CAMK1), SRC Proto-Oncogene, Non-Receptor Tyrosine Kinase (SRC), Glucose-6-Phosphate Isomerase (GPI), N-Acetylglucosamine Kinase (NAGK), Eukaryotic Translation Initiation Factor 5A (EIF5A), N-Myristoyltransferase 1 (NMT1), Vesicle Trafficking 1 (VTA1), Sphingosine Kinase 1 (SPHK1), Ribosomal Protein S6 Kinase A5 (RPS6KA5), Protein Kinase C Alpha (PRKCA), Aldolase, Fructose-Bisphosphate A (ALDOA), Mitogen-Activated Protein Kinase 3 (MAPK3), Protein Tyrosine Phosphatase Non-Receptor Type 1 (PTPN1), Fibronectin Leucine Rich Transmembrane Protein 1 (FLRT1), Growth Factor Receptor Bound Protein 2 (GRB2), Sorting Nexin 4 (SNX4), Enolase 2 (ENO2), Glycogen Synthase Kinase 3 Alpha (GSK3A Glycogen Synthase Kinase 3 Beta (GSK3B), 3-Phosphoinositide Dependent Protein Kinase 1 (PDPK1), C—X—C Motif Chemokine Ligand 6 (CXCL6), SMAD Family Member 2 (SMAD2), SBDS Ribosome Maturation Factor (SBDS), CAMP Regulated Phosphoprotein 19 (ARPP19), Inhibitor Of Growth Family Member 1 (ING1), Drebrin Like (DBNL), Ubiquitin-Fold Modifier Conjugating Enzyme 1 (UFC1), Cytochrome P450 Family 3 Subfamily A Member 4 (CYP3A4), Glutathione S-Transferase Pi 1 (GSTP1), N-6 Adenine-Specific DNA Methyltransferase 1 (N6AMT1), Histone Deacetylase 8 (HDAC8), DEAD-Box Helicase 19B (DDX19B), BCL2 Like 1 (BCL2L1), SMAD Family Member 3 (SMAD3), NME/NM23 Nucleoside Diphosphate Kinase 2 (NME2), Phosphoglycerate Kinase 1 (PGK1), AKT Serine/Threonine Kinase 2 (AKT2), Protein Kinase C Delta (PRKCD), Casein Kinase 2 Alpha 1 (CSNK2A1), Platelet Activating Factor Acetylhydrolase 1b Catalytic Subunit 2 (PAFAHIB2), Protein Tyrosine Phosphatase Non-Receptor Type 11 (PTPN11), Copine 1 (CPNE1), Interleukin 23 Receptor (IL23R), and Insulin Degrading Enzyme (IDE).

In some embodiments, a panel of second trimester PAS biomarkers comprises PGK1, N6AMT1, ESD, COMMD7, GSTP1, and IDE; PGK1, N6AMT1, ESD, COMMD7, GSTP1, IDE, DBNL, LY86, and DDX19b; or PGK1, N6AMT1, ESD, COMMD7, and GSTP1.

In some embodiments, a panel of second trimester PAS biomarkers comprises IDE, IL23R, CPNE1, XPNPEP1, and PAFAHIB2; IDE, IL23R, CPNE1, XPNPEP1, PAFAHIB2, PTPN11, and PRKCD; or IL23R, CPNE1, XPNPEP1, PAFAHIB2, PTPN11, PRKCD, and PGK1.

In some embodiments, a panel of second trimester PAS biomarkers comprises CD5L, FGF5, ESM1, and S100A7. In some embodiments, a panel of second trimester PAS biomarkers comprises IL23R, IDE, CSF1R, and FSTL3. In some embodiments, a panel of second trimester PAS biomarkers comprises CD5L, FGF5, ESM1, S100A7, IL23R, IDE, CSF1R, and FSTL3.

In some embodiments, single markers may also be used to distinguish between subjects in their second trimesters having PAS and controls. For example, in some embodiments, a panel of second trimester PAS biomarkers comprises CD5L, FGF5, ESM1, S100A7, XPNPEP1, and EIF4H. In some embodiments, a panel of second trimester PAS biomarkers comprises CD5L, IDE, MMP17, and SMAD3.

The invention also features uses of the panels for detecting PAS in a subject. The use of such panels allows for early identification of pregnant women having placenta accreta spectrum, for example during the second or third trimesters, or at risk for developing PAS and subsequent monitoring of such patients. Early identification of PAS allows clinicians and staff to prepare for complications during delivery (e.g., hemorrhaging and massive blood loss).

Placenta Accreta Spectrum (PAS)

Subjects with PAS are more likely to experience maternal morbidity and mortality, which can arise due to severe hemorrhage and may require massive blood transfusion. Increased maternal death rates are observed in women with placenta accreta spectrum as are increased rates of hysterectomy and longer hospitalizations. The American College of Obstetricians and Gynecologists (ACOG) and the Society for Maternal-Fetal Medicine have developed an idealized care system for facilities, based on region and expertise of the medical staff, to reduce overall maternal morbidity and mortality in the United States. This system considers PAS a high-risk condition that requires medical staff with appropriate training and experience in managing PAS to be continuously available. Patients with PAS should also have access to staff with expertise in critical care, for example, critical care subspecialists, hematologists, cardiologists, and neonatologists) and a blood bank in the event a transfusion is needed.

The methods and compositions of the present invention allow for early detection of PAS in expecting mothers and ample time to allocate the necessary staff and resources to mitigate risk of a delivery with potentially life-threatening complications.

Biomarkers

In particular embodiments, a biomarker is an organic biomolecule that is differentially present in a sample taken from a subject of one phenotypic status (e.g., having or at risk of developing PAS) as compared with another phenotypic status (e.g., not having PAS). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney, and odds ratio. Biomarkers, alone or in combination, provide measures of relative risk that a subject belongs to one phenotypic status or another. Therefore, they are useful as markers for detecting and/or characterizing a disease (i.e., PAS).

Biomarkers for Placenta Accreta Spectrum

The invention provides a panel of polypeptide biomarkers that are differentially present in subjects having PAS, such as placenta accreta, placenta increta, or placenta percreta.

In some embodiments, the biomarker panel of the present invention comprises one or more of the third trimester biomarkers presented in the following Table 1A.

TABLE 1A

| Third Trimester PAS Biomarkers | | |
| --- | --- | --- |
| Biomarker | Entrez Symbol | Differential Expression in PAS |
| Complement component C8 | C8A C8B C8G | Increased |
| Apolipoprotein M | APOM | Increased |
| WAP, kazal, immunoglobulin, kunitz and NTR domain-containing protein 1 | WFIKKN1 | Increased |
| Growth hormone receptor | GHR | Increased |
| Human Chorionic Gonadotropin | CGA CGB | Increased |
| Myeloid cell surface antigen CD33 | CD33 | Increased |
| Vascular endothelial growth factor receptor 2 | KDR | Increased |
| Interleukin-18 receptor 1 | IL18R1 | Increased |
| Reticulon-4 receptor | RTN4R | Increased |
| Angiopoietin-1 receptor, soluble | TEK | Increased |
| Secreted frizzled-related protein 3 | FRZB | Increased |
| Toll-like receptor 4:Lymphocyte antigen 96 complex | TLR4 LY96 | Increased |
| Cathepsin F | CTSF | Increased |
| Interleukin-37 | IL37 | Increased |
| Muellerian-inhibiting factor | AMH | Increased |
| CD166 antigen | ALCAM | Increased |
| Mediator of RNA polymerase II transcription subunit 1 | MED1 | Increased |
| Ubiquitin-conjugating enzyme E2 G2 | UBE2G2 | Increased |
| Interleukin-13 receptor subunit alpha-1 | IL13RA1 | Increased |
| Immunoglobulin superfamily containing leucine-rich repeat protein 2 | ISLR2 | Increased |
| Cadherin-5 | CDH5 | Increased |
| Neurogenic locus notch homolog protein 1 | NOTCH1 | Increased |
| C-C motif chemokine 3-like 1 | CCL3L1 | Increased |
| Tumor necrosis factor receptor superfamily member 21 | TNFRSF21 | Increased |
| Lymphotoxin alpha2:beta1 | LTA LTB | Increased |
| Epidermal growth factor receptor | EGFR | Increased |
| A disintegrin and metalloproteinase with thrombospondin motifs 13 | ADAMTS13 | Increased |
| Carbonic anhydrase-related protein 10 | CA10 | Increased |
| Ectodysplasin-A, secreted form | EDA | Increased |
| Neural cell adhesion molecule L1-like protein | CHL1 | Increased |
| Repulsive guidance molecule A | RGMA | Increased |
| Sphingosine kinase 2 | SPHK2 | Increased |
| Endothelin-converting enzyme 1 | ECE1 | Increased |
| Complement C2 | C2 | Increased |
| Interleukin-1 Receptor accessory protein | IL1RAP | Increased |
| Alpha-2-antiplasmin | SERPINF2 | Increased |
| Antithrombin-III | SERPINC1 | Increased |
| Gremlin-1 | GREM1 | Decreased |
| A disintegrin and metalloproteinase with thrombospondin motifs 1 | ADAMTS1 | Decreased |
| Calcium/calmodulin-dependent protein kinase kinase 1 | CAMKK1 | Decreased |
| Plasminogen activator inhibitor 1 | SERPINE1 | Decreased |
| Cryptic protein | CFC1 | Decreased |
| Cadherin-12 | CDH12 | Decreased |
| DnaJ homolog subfamily B member 1 | DNAJB1 | Decreased |
| Pescadillo homolog | PES1 | Decreased |
| Metalloproteinase inhibitor 3 | TIMP3 | Decreased |
| L-lactate dehydrogenase B chain | LDHB | Decreased |
| Casein kinase II 2-alpha':2-beta heterotetramer | CSNK2A2 CSNK2B | Decreased |
| Peroxiredoxin-6 | PRDX6 | Decreased |
| Platelet factor 4 | PF4 | Decreased |

In some embodiments, the biomarker panel of the present invention comprises one or more of the second trimester biomarkers presented in the following Table 1B.

TABLE 1B

| Second Trimester PAS Biomarkers | | |
| --- | --- | --- |
| Biomarker | Entrez Symbol | Differential Expression in PAS |
| Anti-Mullerian Hormone | AMH | Increased |
| CD5 Molecule Like | CD5L | Increased |
| Interleukin 7 Receptor | IL7R | Increased |
| Matrix Metallopeptidase 17 | MMP17 | Increased |
| Complement C9 | C9 | Increased |
| Chitinase 3 Like 1 | CHI3L1 | Increased |
| Endothelial Cell Specific Molecule 1 | ESM1 | Increased |
| GDNF Family Receptor Alpha 3 | GFRA3 | Increased |
| Plasminogen Activator Tissue Type | PLAT | Increased |
| S100 Calcium Binding Protein A7 | S100A7 | Increased |
| Colony Stimulating Factor 1 Receptor | CSF1R | Increased |
| Ephrin A2 | EFNA2 | Increased |
| Dermatopontin | DPT | Increased |
| Delta Like Canonical Notch Ligand 1 | DLL1 | Increased |
| Interleukin 5 Receptor Subunit Alpha | IL5RA | Increased |
| Lymphocyte Activating 3 | LAG3 | Increased |
| Follistatin Like 3 | FSTL3 | Increased |
| Fibroblast Growth Factor 5 | FGF5 | Increased |
| SPARC Osteonectin Cwcv And Kazal Like Domains Proteoglycan 2 | SPOCK2 | Increased |
| Laminin Subunit Alpha 1 | LAMA1 | Decreased |
| Laminin Subunit Beta 1 | LAMB1 | Decreased |
| Laminin Subunit Gamma 1 | LAMC1 | Decreased |
| Kirre Like Nephrin Family Adhesion Molecule 3 | KIRREL3 | Decreased |
| Calcium/Calmodulin Dependent Protein Kinase I | CAMK1 | Decreased |
| SRC Proto-Oncogene Non-Receptor Tyrosine Kinase | SRC | Decreased |
| Glucose-6-Phosphate Isomerase | GPI | Decreased |
| N-Acetylglucosamine Kinase | NAGK | Decreased |
| Eukaryotic Translation Initiation Factor 5A | EIF5A | Decreased |
| N-Myristoyltransferase 1 | NMT1 | Decreased |
| Vesicle Trafficking 1 | VTA1 | Decreased |
| Sphingosine Kinase 1 | SPHK1 | Decreased |
| Ribosomal Protein S6 Kinase A5 | RPS6KA5 | Decreased |
| Protein Kinase C Alpha | PRKCA | Decreased |
| Aldolase Fructose-Bisphosphate A | ALDOA | Decreased |
| Mitogen-Activated Protein Kinase 3 | MAPK3 | Decreased |
| Protein Tyrosine Phosphatase Non-Receptor Type 1 | PTPN1 | Decreased |
| Fibronectin Leucine Rich Transmembrane Protein 1 | FLRT1 | Decreased |
| Growth Factor Receptor Bound Protein 2 | GRB2 | Decreased |
| Sorting Nexin 4 | SNX4 | Decreased |
| Enolase 2 | ENO2 | Decreased |
| Glycogen Synthase Kinase 3 Alpha | GSK3A | Decreased |
| Glycogen Synthase Kinase 3 Beta | GSK3B | Decreased |
| 3-Phosphoinositide Dependent Protein Kinase 1 | PDPK1 | Decreased |
| C-X-C Motif Chemokine Ligand 6 | CXCL6 | Decreased |
| SMAD Family Member 2 | SMAD2 | Decreased |
| SBDS Ribosome Maturation Factor | SBDS | Decreased |
| CAMP Regulated Phosphoprotein 19 | ARPP19 | Decreased |
| Inhibitor Of Growth Family Member 1 | ING1 | Decreased |
| Drebrin Like | DBNL | Decreased |
| Ubiquitin-Fold Modifier Conjugating Enzyme 1 | UFC1 | Decreased |
| Cytochrome P450 Family 3 Subfamily A Member 4 | CYP3A4 | Decreased |
| Glutathione S-Transferase Pi 1 | GSTP1 | Decreased |
| N-6 Adenine-Specific DNA Methyltransferase 1 | N6AMT1 | Decreased |
| Histone Deacetylase 8 | HDAC8 | Decreased |
| DEAD-Box Helicase 19B | DDX19B | Decreased |
| BCL2 Like 1 | BCL2L1 | Decreased |
| SMAD Family Member 3 | SMAD3 | Decreased |
| NME/NM23 Nucleoside Diphosphate Kinase 2 | NME2 | Decreased |
| Phosphoglycerate Kinase 1 | PGK1 | Decreased |
| AKT Serine/Threonine Kinase 2 | AKT2 | Decreased |
| Protein Kinase C Delta | PRKCD | Decreased |
| Casein Kinase 2 Alpha 1 | CSNK2A1 | Decreased |

TABLE 1B-continued

Second Trimester PAS Biomarkers

| Biomarker | Entrez Symbol | Differential Expression in PAS |
|---|---|---|
| Platelet Activating Factor Acetylhydrolase 1b Catalytic Subunit 2 | PAFAH1B2 | Decreased |
| Protein Tyrosine Phosphatase Non-Receptor Type 11 | PTPN11 | Decreased |
| Copine 1 | CPNE1 | Decreased |
| Interleukin 23 Receptor | IL23R | Decreased |
| and Insulin Degrading Enzyme | IDE | Decreased |

References herein to a biomarker of Tables 1A or 1B, a panel of biomarkers, or other similar phrase indicates one or more of the biomarkers set forth in Table 1A or Table 1B or otherwise described herein.

A biomarker of the invention may be detected in a biological sample from the subject (e.g., tissue, fluid), including, but not limited to, placental, uterine, blood, and urine and the like.

The invention provides panels comprising isolated biomarkers. The biomarkers can be isolated from biological fluids, such as blood and urine or from tissues such as placental and uterine samples. They can be isolated by any method known in the art. In certain embodiments, this isolation is accomplished using the mass and/or binding characteristics of the markers. For example, a sample comprising the biomolecules can be subjected to chromatographic fractionation and subjected to further separation by, e.g., acrylamide gel electrophoresis. Knowledge of the identity of the biomarker also allows their isolation by immunoaffinity chromatography. By "isolated biomarker" is meant at least 60%, by weight, free from proteins and naturally-occurring organic molecules with which the marker is naturally associated. In some embodiments, the preparation is at least 75%, 80%, 85%, 90%, 95%, or at least 99%, by weight, a purified marker.

Exemplary Biomarkers

One exemplary biomarker present in the panel of the invention is complement component C8. C8A, C8B, and C8G are 584, 591, and 202-amino acid proteins, respectively (NCBI Accession number AAI32914.1 (C8A), AAI30576.1 (C8B), and AAI13627.1 (C8G)). Antibodies to complement component C8 can be made using any method well known in the art, or purchased from a commercial supplier. In aspects of the invention, complement component C8 is upregulated in subjects with PAS as compared to subjects that do not have PAS.

One exemplary biomarker present in the panel of the invention is apolipoprotein M. Apolipoprotein M (APOM) is a 116-amino acid protein (NCBI Accession number AQY76658.1). Antibodies to APOM can be made using any method well known in the art, or purchased from a commercial supplier. In aspects of the invention, APOM is upregulated in subjects with PAS as compared to subjects that do not have PAS.

One exemplary biomarker present in the panel of the invention is WAP, kazal, immunoglobulin, kunitz and NTR domain-containing protein 1 (WFIKKN1), a 548-amino acid protein (NCBI Accession number AAI01607.1). Antibodies to WFIKKN1 can be made using any method well known in the art, or purchased from a commercial supplier. In aspects of the invention, WFIKKN1 is upregulated in subjects with PAS as compared to subjects that do not have PAS.

One exemplary biomarker present in the panel of the invention is growth hormone receptor (GHR), a 638-amino acid protein (NCBI Accession number AAA52555.1). Antibodies to GHR can be made using any method well known in the art, or purchased from a commercial supplier. In aspects of the invention, GHR is upregulated in subjects with PAS as compared to subjects that do not have PAS.

One exemplary biomarker present in the panel of the invention is human chorionic gonadotropin (CGA and CGB), a complex comprising 116 and 155-amino acid proteins (NCBI Accession numbers CAG33708.1 (CGA) or EAW52436.1 (CGB1). Antibodies to CGA and CGB can be made using any method well known in the art, or can be purchased from a commercial supplier. In aspects of the invention, CGA and CGB are upregulated in subjects with PAS as compared to subjects that do not have PAS.

One exemplary biomarker present in the panel of the invention is myeloid cell surface antigen CD33 (CD33), a 364-amino acid protein (NCBI Accession number AAH28152.1). Antibodies to CD33 can be made using any method well known in the art, or can be purchased from a commercial supplier. In aspects of the invention, CD33 is upregulated in subjects with PAS as compared to subjects that do not have PAS.

One exemplary biomarker present in the panel of the invention is vascular endothelial growth factor receptor 2 (VEGFR2 or KDR), a 1356-amino acid protein (NCBI Accession number AAC16450.1). Antibodies to KDR can be made using any method well known in the art, or can be purchased from a commercial supplier. In aspects of the invention, KDR is upregulated in subjects with PAS as compared to subjects that do not have PAS.

One exemplary biomarker present in the panel of the invention is interleukin-18 receptor 1 (IL18R1), a 541-amino acid protein (NCBI Accession number AAH93977.1). Antibodies to IL18R1 can be made using any method well known in the art, or can be purchased from a commercial supplier. In aspects of the invention, IL18R1 is upregulated in subjects with PAS as compared to subjects that do not have PAS.

One exemplary biomarker present in the panel of the invention is reticulon-4 receptor (RTN4R), a 473-amino acid protein (NCBI Accession number AAH11787.1). Antibodies to RTN4R can be made using any method well known in the art, or can be purchased from a commercial supplier. In aspects of the invention, RTN4R is upregulated in subjects with PAS as compared to subjects that do not have PAS.

One exemplary biomarker present in the panel of the invention is angiopoietin-1 receptor, soluble (TEK), a 1124-amino acid protein (NCBI Accession number AAA61139.1). Antibodies to TEK can be made using any method well known in the art, or can be purchased from a commercial supplier. In aspects of the invention, TEK is upregulated in subjects with PAS as compared to subjects that do not have PAS.

One exemplary biomarker present in the panel of the invention is secreted frizzled-related protein 3 (FRZB), a 325-amino acid protein (NCBI Accession number EAX10958.1).

Antibodies to FRZB can be made using any method well known in the art, or can be purchased from a commercial supplier. In aspects of the invention, FRZB is upregulated in subjects with PAS as compared to subjects that do not have PAS.

One exemplary biomarker present in the panel of the invention is toll-like receptor 4: Lymphocyte antigen 96 complex (TLR4 LY96), a complex comprising 839 and 160-amino acid proteins (NCBI Accession numbers AAI17423.1 (TLR4) and AAH20690.1 (LY96). Antibodies to the TLR4 LY96 complex can be made using any method well known in the art, or can be purchased from a commercial supplier. In aspects of the invention, the TLR4 LY96 complex is upregulated in subjects with PAS as compared to subjects that do not have PAS.

One exemplary biomarker present in the panel of the invention is cathepsin F (CTSF), a 484-amino acid protein (NCBI Accession number AAH36451.1). Antibodies to CTSF can be made using any method well known in the art, or can be purchased from a commercial supplier. In aspects of the invention, CTSF is upregulated in subjects with PAS as compared to subjects that do not have PAS.

One exemplary biomarker present in the panel of the invention is interleukin-37 (IL37), a 218-amino acid protein (NCBI Accession number XP_011509265.1). Antibodies to IL37 can be made using any method well known in the art, or can be purchased from, a commercial supplier. In aspects of the invention, IL37 is upregulated in subjects with PAS as compared to subjects that do not have PAS.

One exemplary biomarker present in the panel of the invention is muellerian-inhibiting factor (AMH), a 560-amino acid protein (NCBI Accession number AAH49194.1). Antibodies to AMH can be made using any method well known in the art, or can be purchased from a commercial supplier. In aspects of the invention, AMH is upregulated in subjects with PAS as compared to subjects that do not have PAS.

One exemplary biomarker present in the panel of the invention is CD166 antigen (ALCAM), a 583-amino acid protein (NCBI Accession number AAI37097.1). Antibodies to ALCAM can be made using any method well known in the art, or can be purchased from a commercial supplier. In aspects of the invention, ALCAM is upregulated in subjects with PAS as compared to subjects that do not have PAS.

One exemplary biomarker present in the panel of the invention is mediator of RNA polymerase II transcription subunit 1 (MED1), a 1581 amino acid protein (NCBI Accession number AAI31784.1). Antibodies to MED1 can be made using any method well known in the art, or can be purchased from a commercial supplier. In aspects of the invention, MED1 is upregulated in subjects with PAS as compared to subjects that do not have PAS.

One exemplary biomarker present in the panel of the invention is ubiquitin-conjugating enzyme E2 G2 (UBE2G2), a 165-amino acid protein (NCBI Accession number AAP35560.1). Antibodies to UBE2G2 can be made using any method well known in the art, or can be purchased from a commercial supplier. In aspects of the invention, UBE2G2 is upregulated in subjects with PAS as compared to subjects that do not have PAS.

One exemplary biomarker present in the panel of the invention is interleukin-13 receptor subunit alpha-1 (IL13RA1), a 427-amino acid protein (NCBI Accession number AAH15768.1). Antibodies to IL13RA1 can be made using any method well known in the art, or can be purchased from a commercial supplier. In aspects of the invention, IL13RA1 is upregulated in subjects with PAS as compared to subjects that do not have PAS.

One exemplary biomarker present in the panel of the invention is immunoglobulin superfamily containing leucine-rich repeat protein 2 (ISLR2), a 745-amino acid protein (NCBI Accession number AAI52430.1). Antibodies to ISLR2 can be made using any method well known in the art, or can be purchased from a commercial supplier. In aspects of the invention, ISLR2 is upregulated in subjects with PAS as compared to subjects that do not have PAS.

One exemplary biomarker present in the panel of the invention is cadherin-5 (CDH5), a 669-amino acid protein (NCBI Accession number AAH96364.3). Antibodies to CDH5 can be made using any method well known in the art, or can be purchased from a commercial supplier. In aspects of the invention, CDH5 is upregulated in subjects with PAS as compared to subjects that do not have PAS.

One exemplary biomarker present in the panel of the invention is neurogenic locus notch homolog protein 1 (NOTCH1), a 2556-amino acid protein (NCBI Accession number AAG33848.1). Antibodies to NOTCH1 can be made using any method well known in the art, or can be purchased from a commercial supplier. In aspects of the invention, NOTCH1 is upregulated in subjects with PAS as compared to subjects that do not have PAS.

One exemplary biomarker present in the panel of the invention is C-C motif chemokine 3-like 1 (CCL3L1), a 93-amino acid protein (NCBI Accession number AAI46915.1). Antibodies to CCL3L1 can be made using any method well known in the art, or can be purchased from a commercial supplier. In aspects of the invention, CCL3L1 is upregulated in subjects with PAS as compared to subjects that do not have PAS.

One exemplary biomarker present in the panel of the invention is tumor necrosis factor receptor superfamily member 21 (TNFRSF21), a 655-amino acid protein (NCBI Accession number AAP36088.1). Antibodies to TNFRSF21 can be made using any method well known in the art, or can be purchased from a commercial supplier. In aspects of the invention, TNFRSF21 is upregulated in subjects with PAS as compared to subjects that do not have PAS.

One exemplary biomarker present in the panel of the invention is lymphotoxin alpha2: beta1 (LTA LTB), which comprises 205 and 244-amino acid proteins (NCBI Accession numbers AQY76900.1 (LTA) and AQY76901.1 (LTB)). Antibodies to LTA and LTB can be made using any method well known in the art, or can be purchased from a commercial supplier. In aspects of the invention, LTA and LTB are upregulated in subjects with PAS as compared to subjects that do not have PAS.

One exemplary biomarker present in the panel of the invention is epidermal growth factor receptor (EGFR), a 1210-amino acid protein (NCBI Accession number CAA25240.1). Antibodies to EGFR can be made using any method well known in the art, or can be purchased from a commercial supplier. In aspects of the invention, EGFR is upregulated in subjects with PAS as compared to subjects that do not have PAS.

One exemplary biomarker present in the panel of the invention is a disintegrin and metalloproteinase with thrombospondin motifs 13 (ADAMTS13), a 1427-amino acid protein (NCBI Accession number ABD72606.1). Antibodies to ADAMTS13 can be made using any method well known in the art, or can be purchased from a commercial supplier. In aspects of the invention, ADAMTS13 is upregulated in subjects with PAS as compared to subjects that do not have PAS.

One exemplary biomarker present in the panel of the invention is carbonic anhydrase-related protein 10 (CA10), a 328-amino acid protein (NCBI Accession number AAQ88873.1). Antibodies to CA10 can be made using any method well known in the art, or can be purchased from a commercial supplier. In aspects of the invention, CA10 is upregulated in subjects with PAS as compared to subjects that do not have PAS.

One exemplary biomarker present in the panel of the invention is ectodysplasin-A, secreted form (EDA), a 389-amino acid protein (NCBI Accession number AAI44052.1). Antibodies to EDA can be made using any method well known in the art, or can be purchased from a commercial supplier. In aspects of the invention, EDA is upregulated in subjects with PAS as compared to subjects that do not have PAS.

One exemplary biomarker present in the panel of the invention is neural cell adhesion molecule L1-like protein (CHL1), a 1208-amino acid protein (NCBI Accession number AAI43497.1). Antibodies to CHL1 can be made using any method well known in the art, or can be purchased from a commercial supplier. In aspects of the invention, CHL1 is upregulated in subjects with PAS as compared to subjects that do not have PAS.

One exemplary biomarker present in the panel of the invention is repulsive guidance molecule A (RGMA), a 450-amino acid protein (GENBANK Accession number AAI51133.1).

Antibodies to RGMA can be made using any method well known in the art, or can be purchased from a commercial supplier. In aspects of the invention, RGMA is upregulated in subjects with PAS as compared to subjects that do not have PAS.

One exemplary biomarker present in the panel of the invention is sphingosine kinase 2 (SPHK2), a 654-amino acid protein (GENBANK Accession No. AAH06161.1). Antibodies to SPHK2 can be made using any method well known in the art, or can be purchased from a commercial supplier. In aspects of the invention, SPHK2 is upregulated in subjects with PAS as compared to subjects that do not have PAS.

One exemplary biomarker present in the panel of the invention is endothelin-converting enzyme 1 (ECE1), a 770-amino acid protein (GENBANK Accession No. AAI17257.1). Antibodies to ECE1 can be made using any method well known in the art, or can be purchased from a commercial supplier. In aspects of the invention, ECE1 is upregulated in subjects with PAS as compared to subjects that do not have PAS.

One exemplary biomarker present in the panel of the invention is complement C2 (C2), a 752-amino acid protein (GENBANK Accession No. AQY77246.1). Antibodies to C2 can be made using any method well known in the art, or can be purchased from a commercial supplier. In aspects of the invention, C2 is upregulated in subjects with PAS as compared to subjects that do not have PAS.

One exemplary biomarker present in the panel of the invention is interleukin-1 receptor accessory protein (IL1RAP), a 356-amino acid protein (GENBANK Accession No.

AAQ01759.1). Antibodies to IL1RAP can be made using any method well known in the art, or can be purchased from a commercial supplier. In aspects of the invention, IL1RAP is upregulated in subjects with PAS as compared to subjects that do not have PAS.

One exemplary biomarker present in the panel of the invention is alpha-2-antiplasmin (SERPINF2), a 491-amino acid protein (GENBANK Accession No. AAH31592.1). Antibodies to SERPINF2 can be made using any method well known in the art, or can be purchased from a commercial supplier. In aspects of the invention, SERPINF2 is upregulated in subjects with PAS as compared to subjects that do not have PAS.

One exemplary biomarker present in the panel of the invention is antithrombin-III (SERPINC1), a 464-amino acid protein (GENBANK Accession No. AAA51796.1). Antibodies to SERPINC1 can be made using any method well known in the art, or can be purchased from a commercial supplier. In aspects of the invention, SERPINC1 is upregulated in subjects with PAS as compared to subjects that do not have PAS.

One exemplary biomarker present in the panel of the invention is gremlin-1 (GREM1), a 184-amino acid protein (GENBANK Accession No. AAH69525.1). Antibodies to GREM1 can be made using any method well known in the art, or can be purchased from a commercial supplier. In aspects of the invention, GREM1 is decreased in subjects with PAS as compared to subjects that do not have PAS.

One exemplary biomarker present in the panel of the invention is a disintegrin and metalloproteinase with thrombospondin motifs 1 (ADAMTS1), a 967-amino acid protein (GENBANK Accession No. AAH36515.1). Antibodies to ADAMTS1 can be made using any method well known in the art, or can be purchased from a commercial supplier. In aspects of the invention, ADAMTS1 is decreased in subjects with PAS as compared to subjects that do not have PAS.

One exemplary biomarker present in the panel of the invention is calcium/calmodulin-dependent protein kinase kinase 1 (CAMKK1), a 505-amino acid protein (GENBANK Accession No. AAN37387.1). Antibodies to CAMKK1 can be made using any method well known in the art, or can be purchased from a commercial supplier. In aspects of the invention, CAMKK1 is decreased in subjects with PAS as compared to subjects that do not have PAS.

One exemplary biomarker present in the panel of the invention is plasminogen activator inhibitor 1 (SERPINE1), a 402-amino acid protein (GENBANK Accession No. AAK60338.1). Antibodies to SERPINE1 can be made using any method well known in the art, or can be purchased from a commercial supplier. In aspects of the invention, SERPINE1 is decreased in subjects with PAS as compared to subjects that do not have PAS.

One exemplary biomarker present in the panel of the invention is cryptic protein (CFC1), a 223-amino acid protein (GENBANK Accession No. AAH69508.1). Antibodies to CFC1 can be made using any method well known in the art, or can be purchased from a commercial supplier. In aspects of the invention, CFC1 is decreased in subjects with PAS as compared to subjects that do not have PAS.

One exemplary biomarker present in the panel of the invention is cadherin-12 (CDH12), a 794-amino acid protein (GENBANK Accession No. AAA35623.1). Antibodies to CDH12 can be made using any method well known in the art, or can be purchased from a commercial supplier. In aspects of the invention, CDH12 is decreased in subjects with PAS as compared to subjects that do not have PAS.

One exemplary biomarker present in the panel of the invention is DnaJ homolog subfamily B member 1 (DNAJB1), a 340-amino acid protein (GENBANK Accession No. AAH19827.1). Antibodies to DNAJB1 can be made using any method well known in the art, or can be purchased from a commercial supplier. In aspects of the invention, DNAJB1 is decreased in subjects with PAS as compared to subjects that do not have PAS.

One exemplary biomarker present in the panel of the invention is pescadillo homolog (PES1), a 588-amino acid protein (GENBANK Accession No. AAH32489.1). Antibodies to PES1 can be made using any method well known in the art, or can be purchased from a commercial supplier. In aspects of the invention, PES1 is decreased in subjects with PAS as compared to subjects that do not have PAS.

One exemplary biomarker present in the panel of the invention is metalloproteinase inhibitor 3 (TIMP3), a 211-amino acid protein (GENBANK Accession No. AAH14277.1). Antibodies to TIMP3 can be made using any method well known in the art, or can be purchased from a commercial supplier. In aspects of the invention, TIMP3 is decreased in subjects with PAS as compared to subjects that do not have PAS.

One exemplary biomarker present in the panel of the invention is L-lactate dehydrogenase B chain (LDHB), a 334-amino acid protein (GENBANK Accession No. AAV38570.1). Antibodies to LDHB can be made using any method well known in the art, or can be purchased from a commercial supplier. In aspects of the invention, LDHB is decreased in subjects with PAS as compared to subjects that do not have PAS.

One exemplary biomarker present in the panel of the invention is casein kinase II 2-alpha: 2-beta heterotetramer (CSNK2A2 CSNK2B) that comprises 350 and 212-amino acid proteins (GENBANK Accession No. AAH08812.1 (CSNK2A2) and NCBI Accession No. NP_001269314.1 (CSNK2B)). Antibodies to CSNK2A2 and CSNK2B can be made using any method well known in the art, or can be purchased from a commercial supplier. In aspects of the invention, CSNK2A2 and CSNK2B are decreased in subjects with PAS as compared to subjects that do not have PAS.

One exemplary biomarker present in the panel of the invention is peroxiredoxin-6 (PRDX6), a 224-amino acid protein (GENBANK Accession No. AAH53550.1). Antibodies to PRDX6 can be made using any method well known in the art, or can be purchased from a commercial supplier. In aspects of the invention, PRDX6 is decreased in subjects with PAS as compared to subjects that do not have PAS.

One exemplary biomarker present in the panel of the invention is platelet factor 4 (PF4), a 101-amino acid protein (GENBANK Accession No. AAH93965.1). Antibodies to PF4 can be made using any method well known in the art, or can be purchased from a commercial supplier. In aspects of the invention, PF4 is decreased in subjects with PAS as compared to subjects that do not have PAS.

Biomarkers and Different Forms of a Protein

Proteins frequently exist in a sample in a plurality of different forms. These forms can result from pre- and/or post-translational modification. Pre-translational modified forms include allelic variants, splice variants, and RNA editing forms. Post-translationally modified forms include forms resulting from proteolytic cleavage (e.g., cleavage of a signal sequence or fragments of a parent protein), glyco-sylation, phosphorylation, lipidation, oxidation, methyl-ation, cysteinylation, sulphonation, and acetylation. When detecting or measuring a protein in a sample, any or all of the forms may be measured to determine the level of biomarker or a form of interest is measured. The ability to differentiate between different forms of a protein depends upon the nature of the difference and the method used to detect or measure the protein. For example, an immunoassay using a monoclonal antibody will detect all forms of a protein containing the epitope and will not distinguish between them. However, a sandwich immunoassay that uses two antibodies directed against different epitopes on a protein will detect all forms of the protein that contain both epitopes and will not detect those forms that contain only one of the epitopes. Distinguishing different forms of an analyte or specifically detecting a particular form of an analyte is referred to as "resolving" the analyte.

Mass spectrometry is a particularly powerful methodol-ogy to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where tra-ditional immunoassay fails to distinguish the forms and fails to specifically detect to useful biomarker.

One useful methodology combines mass spectrometry with immunoassay. For example, a biospecific capture reagent (e.g., an antibody, aptamer, Affibody, and the like that recognizes the biomarker and other forms of it) is used to capture the biomarker of interest. In some embodiments, the biospecific capture reagent is bound to a solid phase, such as a bead, a plate, a membrane or an array. After unbound materials are washed away, the captured analytes are detected and/or measured by mass spectrometry. This method will also result in the capture of protein interactors that are bound to the proteins or that are otherwise recog-nized by antibodies and that, themselves, can be biomarkers. Various forms of mass spectrometry are useful for detecting the protein forms, including laser desorption approaches, such as traditional matrix-assisted laser desorption/ioniza-tion (MALDI) or surface-enhanced laser desorption/ioniza-tion (SELDI), electrospray ionization, and the like.

Thus, when reference is made herein to detecting a particular protein or to measuring the amount of a particular protein, it means detecting and measuring the protein with or without resolving various forms of protein. For example, the step of "detecting two or more biomarkers in Table 1A or 1B" includes measuring the two or more biomarkers by means that do not differentiate between various forms of the protein (e.g., certain immunoassays) as well as by means that differentiate some forms from other forms or that measure a specific form of the protein.

Detection of Biomarkers for Placenta Accreta Spectrum

The biomarkers of this invention can be detected by any suitable method. The methods described herein can be used individually or in combination for a more accurate detection of the biomarkers (e.g., biochip in combination with mass spectrometry, immunoassay in combination with mass spec-trometry, and the like).

Detection paradigms that can be employed in the inven-tion include, but are not limited to, optical methods, elec-trochemical methods (voltammetry and amperometry tech-niques), atomic force microscopy, and radio frequency methods, e.g., multipolar resonance spectroscopy.

Illustrative of optical methods, in addition to microscopy, both confocal and non-confocal, are detection of fluores-cence, luminescence, chemiluminescence, absorbance, reflectance, transmittance, and birefringence or refractive index (e.g., surface plasmon resonance, ellipsometry, a reso-nant mirror method, a grating coupler waveguide method, or interferometry). These and additional methods are described infra.

Detection by Immunoassay

In particular embodiments, the biomarkers of the inven-tion are measured by immunoassay. Immunoassay typically utilizes an antibody (or other agent that specifically binds the marker) to detect the presence or level of a biomarker in a sample. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, Western blot, sandwich immunoassays including ELISA and other enzyme immunoassays, fluorescence-based immunoassays, and chemiluminescence. Nephelometry is an assay done in liquid phase, in which antibodies are in solution. Binding of the antigen to the antibody results in changes in absorbance, which is measured. Other forms of immunoassay include magnetic immunoassay, radioimmunoassay, and real-time immuno-quantitative PCR (iqPCR).

Immunoassays can be carried out on solid substrates (e.g., chips, beads, microfluidic platforms, membranes) or on any other form that supports binding of the antibody to the marker and subsequent detection. In some embodiments, the capture molecule (i.e., antibody) is bound to the solid substrate. A single marker may be detected at a time or a multiplex format may be used. Multiplex immune-analysis may involve planar microarrays (protein chips) and bead-based microarrays (suspension arrays).

In a SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

Detection by Biochip

In aspects of the invention, a sample is analyzed by means of a biochip (also known as a microarray). The polypeptides and nucleic acid molecules of the invention are useful as hybridizable array elements in a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28: e3. i-e3. vii, 2000), MacBeath et al., (Science 289:1760-1763, 2000), Zhu et al. (Nature Genet. 26:283-289), and in U.S. Pat. No. 6,436,665, the contents of each are hereby incorporated by reference.

Detection by Protein Biochip

In aspects of the invention, a sample is analyzed by means of a protein biochip (also known as a protein microarray). Such biochips are useful in high-throughput low-cost screens to identify alterations in the expression or post-translation modification of a polypeptide of the invention, or a fragment thereof. In embodiments, a protein biochip of the invention binds a biomarker present in a subject sample and detects an alteration in the level of the biomarker. Typically, a protein biochip features a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins (e.g., antibodies that bind a marker of the invention) are spotted on a substrate using any convenient method known to the skilled artisan (e.g., by hand or by inkjet printer).

In embodiments, the protein biochip is hybridized with a detectable probe. Such probes can be polypeptides, nucleic acid molecules, antibodies, or small molecules. For some applications, polypeptide and nucleic acid molecule probes are derived from a biological sample taken from a patient, such as a bodily fluid or tissue (e.g., placenta, uterus, blood, and urine, and the like). Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual, 1998, New York: Cold Spring Harbor Laboratories. After removal of non-specific probes, specifically bound probes are detected, for example, by fluorescence, enzyme activity (e.g., an enzyme-linked calorimetric assay), direct immuno-assay, radiometric assay, or any other suitable detectable method known to the skilled artisan.

Many protein biochips are described in the art. These include, for example, protein biochips produced by Ciphergen Biosystems, Inc. (Fremont, CA), Zyomyx (Hayward, CA), Packard BioScience Company (Meriden, CT), Phylos (Lexington, MA), Invitrogen (Carlsbad, CA), Biacore (Uppsala, Sweden) and Procognia (Berkshire, UK). Examples of such protein biochips are described in the following patents or published patent applications: U.S. Pat. Nos. 6,225,047; 6,537,749; 6,329,209; and 5,242,828; PCT International Publication Nos. WO 00/56934; WO 03/048768; and WO 99/51773.

Detection by Nucleic Acid Biochip

In aspects of the invention, a sample is analyzed by means of a nucleic acid biochip (also known as a nucleic acid microarray). To produce a nucleic acid biochip, oligonucleotides may be synthesized or bound to the surface of a substrate using a chemical coupling procedure and an ink jet application apparatus, as described in PCT application WO95/251116 (Baldeschweiler et al.). Alternatively, a gridded array may be used to arrange and link cDNA fragments or oligonucleotides to the surface of a substrate using a vacuum system, thermal, UV, mechanical or chemical bonding procedure.

A nucleic acid molecule (e.g., RNA or DNA) derived from a biological sample may be used to produce a hybridization probe as described herein. The biological samples are generally derived from a patient, e.g., as a bodily fluid or from tissue (placental, uterine, blood, and urine, and the like). For some applications, cultured cells or other tissue preparations may be used. The mRNA is isolated according to standard methods, and cDNA is produced and used as a template to make complementary RNA suitable for hybridization. Such methods are well known in the art. The RNA is amplified in the presence of fluorescent nucleotides, and the labeled probes are then incubated with the microarray to allow the probe sequence to hybridize to complementary oligonucleotides bound to the biochip.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide. Stringent temperature conditions will ordinarily include temperatures of at least about 30° C., of at least about 37° C., or of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In embodiments, hybridization will occur at 37° C. in 500 mM NaCl, 50 mM trisodium citrate, 1% SDS, 35% formamide, and 100 µg/ml denatured salmon sperm DNA (ssDNA). In other embodiments, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. In some embodiments, stringent salt concentration for the wash steps will be less than about 30 mM NaCl and 3 mM trisodium citrate or less than about 15 mM NaCl and 1.5 mM trisodium citrate. Stringent temperature conditions for the wash steps will ordinarily include a temperature of at least about 25° C., of at least about 42° C., or of at least about 68° C. In embodiments, wash steps will occur at 25° C. in 30 mM NaCl, 3 mM trisodium citrate, and 0.1% SDS. In another embodiment, wash steps will occur at 42° C. in 15 mM NaCl, 1.5 mM trisodium citrate, and 0.1% SDS. In other embodiments, wash steps will occur at 68° C. in 15 mM NaCl, 1.5 mM trisodium citrate, and 0.1% SDS. Additional variations on these conditions will be readily apparent to those skilled in the art.

Detection system for measuring the absence, presence, and amount of hybridization for all of the distinct nucleic acid sequences are well known in the art. For example, simultaneous detection is described in Heller et al., Proc. Natl. Acad. Sci. 94:2150-2155, 1997. In embodiments, a scanner is used to determine the levels and patterns of fluorescence.

Detection by Mass Spectrometry

In aspects of the invention, the biomarkers of this invention are detected by mass spectrometry (MS). Mass spectrometry is a well-known tool for analyzing chemical compounds that employs a mass spectrometer to detect gas phase ions. Mass spectrometers are well known in the art and include, but are not limited to, time-of-flight, magnetic sector, quadrupole filter, ion trap, ion cyclotron resonance, electrostatic sector analyzer, and hybrids of these. The method may be performed in an automated (Villanueva, et al., Nature Protocols (2006) 1 (2): 880-891) or semi-automated format. This can be accomplished, for example with the mass spectrometer operably linked to a liquid chromatography device (LC-MS/MS or LC-MS) or gas chromatography device (GC-MS or GC-MS/MS). Methods for performing mass spectrometry are well known and have been disclosed, for example, in US Patent Application Publication Nos: 20050023454; 20050035286; U.S. Pat. No. 5,800,979 and the references disclosed therein.

Laser Desorption/Ionization (LDI)

In embodiments, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of proteins by LDI can take the form of MALDI or of SELDI.

Laser desorption/ionization in a single time of flight instrument typically is performed in linear extraction mode. Tandem mass spectrometers can employ orthogonal extraction modes.

Matrix-assisted Laser Desorption/Ionization (MALDI) and Electrospray Ionization (ESI)

In embodiments, the mass spectrometric technique for use in the invention is matrix-assisted laser desorption/ionization (MALDI) or electrospray ionization (ESI). In related embodiments, the procedure is MALDI with time of flight (TOF) analysis, known as MALDI-TOF MS. This involves forming a matrix on a membrane with an agent that absorbs the incident light strongly at the particular wavelength employed. The sample is excited by UV or IR laser light into the vapor phase in the MALDI mass spectrometer. Ions are generated by the vaporization and form an ion plume. The ions are accelerated in an electric field and separated according to their time of travel along a given distance, giving a mass/charge (m/z) reading which is very accurate and sensitive. MALDI spectrometers are well known in the art and are commercially available from, for example, PerSeptive Biosystems, Inc. (Framingham, Mass., USA).

Magnetic-based serum processing can be combined with traditional MALDI-TOF. Through this approach, improved peptide capture is achieved prior to matrix mixture and deposition of the sample on MALDI target plates. Accordingly, in embodiments, methods of peptide capture are enhanced through the use of derivatized magnetic bead based sample processing.

MALDI-TOF MS allows scanning of the fragments of many proteins at once. Thus, many proteins can be run simultaneously on a polyacrylamide gel, subjected to a method of the invention to produce an array of spots on a collecting membrane, and the array may be analyzed. Subsequently, automated output of the results is provided by using a server (e.g., ExPASy) to generate the data in a form suitable for computers.

Other techniques for improving the mass accuracy and sensitivity of the MALDI-TOF MS can be used to analyze the fragments of protein obtained on a collection membrane. These include, but are not limited to, the use of delayed ion extraction, energy reflectors, ion-trap modules, and the like. In addition, post source decay and tandem mass spectrometry (MS-MS) analysis are useful to provide further structural analysis. With ESI, the sample is in the liquid phase, and the analysis can be by ion-trap, TOF, single quadrupole, multi-quadrupole mass spectrometers, and the like. The use of such devices (other than a single quadrupole) allows MS-MS or multistage mass spectrometry (MSn) analysis to be performed. Tandem mass spectrometry allows multiple reactions to be monitored at the same time.

Capillary infusion may be employed to introduce the marker to a desired mass spectrometer implementation, for instance, because it can efficiently introduce small quantities of a sample into a mass spectrometer without destroying the vacuum. Capillary columns are routinely used to interface the ionization source of a mass spectrometer with other separation techniques including, but not limited to, gas chromatography (GC) and liquid chromatography (LC). GC and LC can serve to separate a solution into its different components prior to mass analysis. Such techniques are readily combined with mass spectrometry. One variation of the technique is the coupling of high-performance liquid chromatography (HPLC) to a mass spectrometer for integrated sample separation/and mass spectrometer analysis.

Quadrupole mass analyzers may also be employed as needed to practice the invention. Fourier-transform ion cyclotron resonance (FTMS) can also be used for some invention embodiments. It offers high resolution and the ability of tandem mass spectrometry experiments. FTMS is based on the principle of a charged particle orbiting in the presence of a magnetic field. Coupled to ESI and MALDI, FTMS offers high accuracy with errors as low as 0.001%.

Surface-Enhanced Laser Desorption/Ionization (SELDI)

In embodiments, the mass spectrometric technique for use in the invention is "Surface Enhanced Laser Desorption and Ionization" or "SELDI," as described, for example, in U.S. Pat. Nos. 5,719,060 and 6,225,047. This refers to a method of desorption/ionization gas phase ion spectrometry (e.g., mass spectrometry) in which an analyte (here, one or more of the biomarkers) is captured on the surface of a SELDI mass spectrometry probe.

SELDI has also been called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent," or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars, and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid, or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins, and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen comprise surfaces having chromatographic or biospecific adsorbents attached thereto at addressable locations. Ciphergen's ProteinChip® arrays include NP20 (hydrophilic); H4 and H50 (hydrophobic); SAX-2, Q-10 and (anion exchange); WCX-2 and CM-10 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol) methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC 3 and IMAC 30) or O-methacryloyl-N,N-bis-carboxymethyl tyrosine functionalities (IMAC 50) that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); U.S. Pat. No. 6,897,072 (Rich et al., "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003-0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Application Publication No. US 2003/-0218130 A1 (Boschetti et al., "Biochips With Surfaces Coated With Polysaccharide-Based Hydrogels," Apr. 14, 2003) and U.S. Pat. No. 7,045,366 (Huang et al., "Photocrosslinked Hydrogel Blend Surface Coatings" May 16, 2006), the contents of each are incorporated herein by reference in their entirety.

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immuno-adsorbent that has anti-bodies that bind the biomarkers. After washing the adsorbent to remove unbound material, the biomarkers are eluted from the solid phase and detected by applying to a SELDI biochip that binds the biomarkers and analyzing by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

METHODS OF THE INVENTION

Panels comprising biomarkers of the invention are used to identify pregnant women who have PAS. In other embodi-ments, a panel of the invention is used characterize a subject's PAS by determining the molecular profile of the PAS. In certain embodiments, panels of the invention are used to select a course of treatment for a subject. The phrase "placenta accreta spectrum (PAS)" includes placenta accreta, placenta increta, and placenta percreta. Based on the particular disorder a subject has, further procedures may be indicated, including additional diagnostic tests or therapeu-tic procedures or regimens.

In aspects of the invention, the biomarkers of the inven-tion can be used in diagnostic tests to identify early stage PAS (i.e., during the second trimester) in a subject.

In some embodiments, the correlation of test results with PAS involves applying a classification algorithm of some kind to the results to generate the status. In some embodi-ments, the biomarkers described herein can be used in conjunction with clinical tools and ultrasound imaging data to develop a robust algorithm to predict PAS. In some embodiments, the markers used to detect or predict PAS are useful in detecting the condition in the second trimester of pregnancy. In other embodiments, the markers of the present invention are used to detect or predict PAS in the third trimester of pregnancy. The classification algorithm may be as simple as determining if the amounts of the markers listed in Table 1A or 1B are above or below a particular cut-off number. When multiple biomarkers are used, the classifica-tion algorithm may be a linear regression formula. Alterna-tively, the classification algorithm may be the product of any of a number of learning algorithms described herein.

In the case of complex classification algorithms, it may be necessary to perform the algorithm on the data, thereby determining the classification, using a computer, e.g., a programmable digital computer. In either case, one can then record the status on tangible medium, for example, in computer-readable format such as a memory drive or disk or simply printed on paper. The result also could be reported on a computer screen.

Biomarkers of the Invention

Individual biomarkers are useful diagnostic biomarkers. In addition, as described in the examples, it has been found that specific combinations of biomarkers provide greater predictive value of a particular status than any single biomarker alone, or any other combination of previously iden-tified biomarkers. Specifically, the detection of a plurality of biomarkers in a sample can increase the sensitivity, accu-racy, and specificity of the test.

Each biomarker described herein can be differentially present in PAS, and, therefore, each is individually useful in aiding in the detection of PAS. The method involves, first, measuring the selected biomarker in a subject sample using any method well known in the art including, but not limited to, the methods described herein, e.g. capture on a SELDI biochip followed by detection by mass spectrometry and, second, comparing the measurement with an amount or cut-off that distinguishes a positive PAS status from a negative PAS status. The diagnostic amount represents a measured amount of a biomarker above which or below which a subject is classified as having a particular PAS status. For example, if the biomarker is up-regulated in a subject having PAS compared to normal, then a measured amount above the diagnostic cutoff provides a diagnosis of PAS. Alternatively, if the biomarker is down-regulated dur-ing PAS, then a measured amount below the diagnostic cutoff provides a diagnosis of PAS. As is well understood in the art, by adjusting the particular diagnostic cut-off used in an assay, one can increase sensitivity or specificity of the diagnostic assay depending on the preference of the diag-nostician. The particular diagnostic cut-off can be deter-mined, for example, by measuring the amount of the bio-marker in a statistically significant number of samples from subjects with the PAS and drawing the cut-off to suit the diagnostician's desired levels of specificity and sensitivity.

The biomarkers of this invention (used alone or in com-bination) show a statistical difference in different PAS statuses of at least $p \leq 0.05$, $p \leq 10^{-2}$, $p \leq 10^{-3}$, $p \leq 10^{-4}$, or $p \leq 10^{-5}$. Diagnostic tests that use these biomarkers alone or in combination show a sensitivity and specificity of at least 75%, at least 80%, at least 85%, at least 90%, at least 95%, at least 98%, or about 100%.

Determining Course (Progression/Improvement) of PAS

In one embodiment, this invention provides methods for determining the course of disease in a subject. Disease course refers to changes in disease status over time, includ-ing disease progression (worsening) and disease regression (improvement). Over time, the amounts or relative amounts (e.g., the pattern) of the biomarkers change. Accordingly, this method involves measuring the panel of biomarkers in a subject at least two different time points, e.g., a first time and a second time, and comparing the change in amounts, if any. The course of disease (e.g., during treatment) is deter-mined based on these comparisons.

Reporting the Status

Additional embodiments of the invention relate to the communication of assay results or diagnoses or both to technicians, physicians, or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are commu-nicated.

In an embodiment of the invention, detecting PAS based on the differential presence or absence in a test subject of the biomarkers of Table 1A or Table 1B is communicated to the subject as soon as possible after detecting PAS. The detec-tion of PAS may be communicated to the subject by the subject's treating physician. Alternatively, the detection of PAS may be sent to a test subject by email or communicated to the subject by phone. A computer may be used to communicate the diagnosis by email or phone. In certain embodiments, the message containing results of a test to detect PAS may be generated and delivered automatically to the subject using a combination of computer hardware and software which will be familiar to artisans skilled in telecommunications. One example of a healthcare-oriented communications system is described in U.S. Pat. No. 6,283, 761; however, the present invention is not limited to methods that utilize this particular communications system. In certain embodiments of the methods of the invention, all or some of the method steps, including the assaying of samples, detecting the presence or absence of PAS of diseases, and communicating of assay results, may be carried out in diverse (e.g., foreign) jurisdictions.

Subject Management

In certain embodiments, the methods of the invention involve managing subject treatment based on the status. Such management includes referral, for example, to an obstetrician or gynecologist, or other actions of the physician or clinician subsequent to determining PAS status. For example, if PAS is detected in a subject, then a certain regime of treatment, such as prescription or administration of therapeutic agent might follow. A patient can be transferred to the care of a Center of Excellence or other facility with the experienced, trained staff and resources to handle PAS deliveries and complications therefrom (i.e., hemorrhages). Alternatively, if PAS is not detected, further testing may be performed to detect a specific disease that might the patient might be suffering from. Also, if the diagnostic test gives an inconclusive result on PAS status, further tests may be called for.

Hardware and Software

In any of the methods described herein, the step of correlating the measurement of the biomarker(s) with PAS can be performed on general-purpose or specially-programmed hardware or software.

In aspects, the analysis is performed by a software classification algorithm. The analysis of analytes by any detection method well known in the art, including, but not limited to the methods described herein, will generate results that are subject to data processing. Data processing can be performed by the software classification algorithm. Such software classification algorithms are well known in the art and one of ordinary skill can readily select and use the appropriate software to analyze the results obtained from a specific detection method.

In aspects, the analysis is performed by a computer-readable medium. The computer-readable medium can be non-transitory and/or tangible. For example, the computer readable medium can be volatile memory (e.g., random access memory and the like) or non-volatile memory (e.g., read-only memory, hard disks, floppy discs, magnetic tape, optical discs, paper table, punch cards, and the like).

For example, analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. Exemplary software includes, but is not limited to, Ciphergen's ProteinChip® software, in which data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set at zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, for example, as part of Ciphergen's ProteinChip® software package, that can automate the detection of peaks. This software functions by identifying signals having a signal-to-noise ratio above a selected threshold and labeling the mass of the peak at the centroid of the peak signal. In embodiments, many spectra are compared to identify identical peaks present in some selected percentage of the mass spectra. One version of this software clusters all peaks appearing in the various spectra within a defined mass range, and assigns a mass (N/Z) to all the peaks that are near the mid-point of the mass (M/Z) cluster.

In aspects, software used to analyze the data can include code that applies an algorithm to the analysis of the results (e.g., signal to determine whether the signal represents a peak in a signal that corresponds to a biomarker according to the present invention). The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

Classification Algorithms for Qualifying PAS Status

In some embodiments, data derived from the assays (e.g., ELISA assays) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting if a particular biological sample is associated with a certain biological condition (e.g., PAS-positive versus PAS-negative).

The training data set that is used to form the classification model may comprise raw data or pre-processed data. In some embodiments, raw data can be obtained directly from time-of-flight spectra or mass spectra, and then may be optionally "pre-processed" as described above. Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART-classification and regression trees), artificial neural networks such as back propagation networks, discriminant analyses (e.g., Bayesian classifier or Fischer analysis), logistic classifiers, and support vector classifiers (support vector machines).

In embodiments, a supervised classification method is a recursive partitioning process. Recursive partitioning processes use recursive partitioning trees to classify spectra derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm. Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application No. 2002 0193950 A1 (Gavin et al., "Method or analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for ovarian cancer. The classification algorithms, in turn, form the base for diagnostic tests by providing diagnostic values (e.g., cut-off points) for biomarkers used singly or in combination.

Kits for Detection of Biomarkers for Placenta Accreta Spectrum

In another aspect, the invention provides kits for aiding in the detection of placenta accreta spectrum (e.g., detecting placenta accreta spectrum, selecting a treatment method for a subject at risk of having delivery complications due to placenta accreta spectrum, and the like), which kits are used to detect biomarkers according to the invention. In one embodiment, the kit comprises agents that specifically recognize the biomarkers identified in Table 1A or Table 1B. In related embodiments, the agents are antibodies. The kit may contain 1, 2, 3, 4, 5, or more different antibodies that each specifically recognize one of the biomarkers set forth in Table 1A or Table 1B.

In another embodiment, the kit comprises a solid support, such as a chip, a microtiter plate, or a bead or resin having capture reagents attached thereon, wherein the capture reagents bind the biomarkers of the invention. Thus, for example, the kits of the present invention can comprise mass spectrometry probes for SELDI, such as ProteinChip® arrays. In the case of biospecific capture reagents, the kit can comprise a solid support with a reactive surface, and a container comprising the biospecific capture reagents.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for use in any of the methods described herein. In embodiments, the instructions provide suitable operational parameters in the form of a label or separate insert. For example, the instructions may inform a consumer about how to collect the sample, how to wash the probe or the particular biomarkers to be detected.

In yet another embodiment, the kit can comprise one or more containers with controls (e.g., biomarker samples) to be used as standard(s) for calibration.

The following examples are put forth so as to provide those of ordinary skill in the art with a complete disclosure and description of how to make and use the assay, screening, and therapeutic methods of the invention, and are not intended to limit the scope of what the inventors regard as their invention.

Examples

Example 1: PAS biomarkers in Third Trimester Pregnancies

The primary aim of this exploratory study was to determine if women with PAS have a unique protein signature in the maternal plasma at time of third-trimester delivery compared to women without PAS. An aptamer-based platform for biomarker discovery was used to conduct the analysis. This platform had been previously used in biomarker discovery studies in cardiovascular diseases and Alzheimer's disease. In pregnancy, there have been limited studies using aptamer-based proteomic studies for discovery of biomarkers and pathogenic pathways in preeclampsia. Plasma samples were obtained prior to delivery from 16 participants with PAS and controls with similar gestational ages (35.1 weeks versus 35.5 weeks respectively). Characteristics of the 16 PAS cases and 10 controls are summarized in Table 2.

TABLE 2

Baseline and delivery characteristics of placenta
accreta spectrum cases and controls

| | Invasive placenta (n = 16) | Non-invasive placenta (n = 10) |
|---|---|---|
| Site | | |
| BIDMC | 10 (62.5) | 5 (50.0) |
| Utah | 6 (37.5) | 5 (50.0) |
| Maternal age | 34.1 (32.4-37.2) | 30.8 (30.0-36.7) |
| BMI at delivery | 33.7 (26.5-43.0) | 28.5 (27.6-31.1) |
| Race | | |
| White | 10 (62.5) | 6 (60.0) |
| Black | 3 (18.8) | 1 (10.0) |
| Hispanic | 0 (0.0) | 1 (10.0) |
| Other/Unknown | 3 (18.8) | 2 (20.0) |
| Number of prior cesarean deliveries | | |
| 0 | 1 (6.3) | 4 (40.0) |
| 1 | 7 (43.8) | 5 (50.0) |
| 2 | 2 (12.5) | 0 (0.0) |
| 3 | 2 (12.5) | 1 (10.0) |
| 4 | 4 (25.0) | 0 (0.0) |
| History of other uterine surgery | | |
| Myomectomy | 1 (6.3) | 0 (0.0) |
| D&E | 3 (18.8) | 2 (20.0) |
| Endometrial ablation | 0 (0.0) | 0 (0.0) |
| Other | 6 (37.5) | 1 (10.0) |

TABLE 2-continued

Baseline and delivery characteristics of placenta
accreta spectrum cases and controls

| | Invasive placenta (n = 16) | Non-invasive placenta (n = 10) |
|---|---|---|
| Previa in current pregnancy | | |
| Yes | 13 (81.3) | 4 (40.0) |
| No | 2 (12.5) | 5 (50.0) |
| Unknown | 1 (6.3) | 1 (10.0) |
| Current smoker | 1 (6.3) | 1 (10.0) |
| Hypothyroidism | 0 (0.0) | 0 (0.0) |
| Hyperthyroidism | 1 (6.3) | 0 (0.0) |
| Diabetes | 1 (6.3) | 1 (10.0) |
| Chronic hypertension | 2 (12.5) | 0 (0.0) |
| Gestational hypertension or preeclampsia | 1 (6.3) | 1 (10.0) |
| Cholestasis | 0 (0.0) | 0 (0.0) |
| Intrauterine growth restriction | 1 (6.3) | 0 (0.0) |
| Gestational age at delivery | 35.1 (34.6-35.4) | 35.5 (35.2-35.7) |
| Fetal anomaly | 1 (6.3) | 1 (10.0) |
| Labor | 1 (6.3) | 3 (30.0) |
| Intrauterine fetal demise | 1 (6.3) | 0 (0.0) |

Data are presented as median (interquartile range) or n (%)

Cases and controls were similar with regard to maternal age, race, smoking, and gestational age at the blood draw. The prevalence of prior cesarean delivery and other uterine surgery was higher among cases. In addition, over 81% of the PAS group had placenta previa compared to 40% of controls.

Figure 1B:
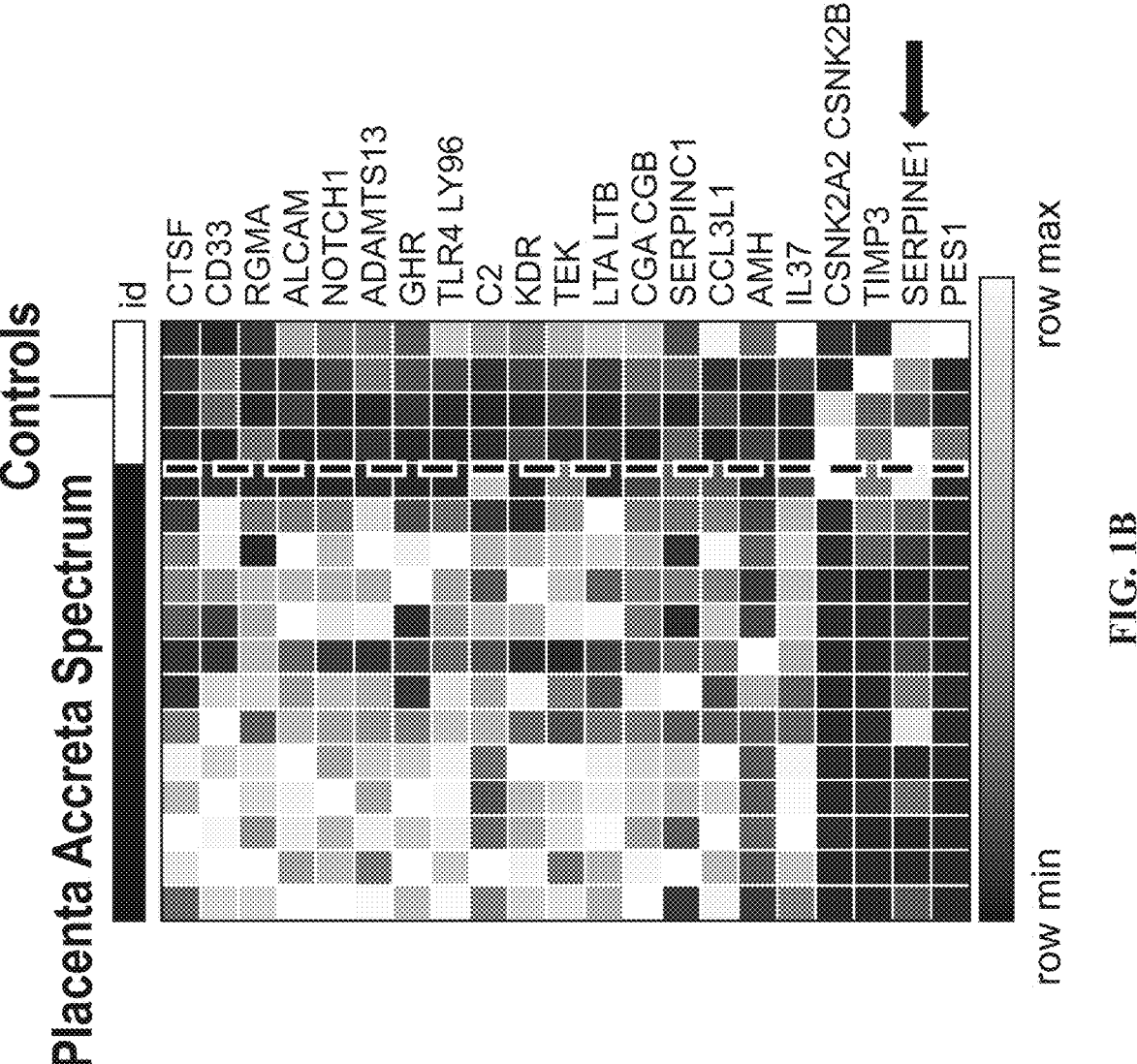

SOMAscan® analysis identified 50 out of 1,305 plasma proteins with expression levels that were significantly different (p<0.01) between third trimester PAS cases and controls. 37 proteins were increased and 13 were decreased in cases compared with controls. FIG. 1A shows a heatmap of the 21 proteins with the most significant differential expression between cases and controls and highlights the relative minimum and maximum concentrations for each protein. Interestingly, of the top dysregulated proteins, SERPINE1 (or PAI-1) has been previously reported in PAS to be altered, confirming that SOMAscan® is an efficient method to reproduce previously published findings. FIG. 1B depicts the results of an analysis restricted to participants who had concomitant placenta previa (13 cases and 4 controls). The patterns of differential protein expression between cases and controls in this subgroup remained similar.

The 50 up-regulated and down-regulated proteins that were statistically significant (p value <0.01) between third trimester cases and controls are listed in Tables 3 and 4, respectively.

TABLE 3

Up-regulated proteins between third trimester placenta accreta spectrum cases and controls
Increased in Placenta Accreta Spectrum

| Target Full Name | Target | Entrez Symbol | p | Fold Change in Protein Expression Median | Fold Change in Protein Expression Mean |
|---|---|---|---|---|---|
| Complement component C8 | C8 | C8A C8B C8G | 0.0096 | 2.03 | 1.54 |
| Apolipoprotein M | ApoM | APOM | 0.0098 | 1.85 | 1.57 |
| WAP, kazal, immunoglobulin, kunitz and NTR domain-containing protein 1 | WFKN1 | WFIKKN1 | 0.0087 | 1.84 | 1.46 |

TABLE 3-continued

Up-regulated proteins between third trimester placenta accreta spectrum cases and controls
Increased in Placenta Accreta Spectrum

| Target Full Name | Target | Entrez Symbol | p | Fold Change in Protein Expression | |
|---|---|---|---|---|---|
| | | | | Median | Mean |
| Growth hormone receptor | Growth hormone receptor | GHR | 0.0014 | 1.81 | 1.69 |
| Human Chorionic Gonadotropin | HCG | CGA CGB | 0.0008 | 1.74 | 1.56 |
| Myeloid cell surface antigen CD33 | Siglec-3 | CD33 | 0.0015 | 1.68 | 1.81 |
| Vascular endothelial growth factor receptor 2 | VEGF sR2 | KDR | 0.0014 | 1.67 | 1.57 |
| Interleukin-18 receptor 1 | IL-18 Ra | IL18R1 | 0.0054 | 1.66 | 1.50 |
| Reticulon-4 receptor | Nogo Receptor | RTN4R | 0.0077 | 1.63 | 1.50 |
| Angiopoietin-1 receptor, soluble | sTie-2 | TEK | 0.0026 | 1.58 | 1.48 |
| Secreted frizzled-related protein 3 | sFRP-3 | FRZB | 0.0094 | 1.56 | 1.44 |
| Toll-like receptor 4:Lymphocyte antigen 96 complex | TLR4:MD-2 complex | TLR4 LY96 | 0.0026 | 1.52 | 1.38 |
| Cathepsin F | CATF | CTSF | 0.0006 | 1.52 | 1.56 |
| Interleukin-37 | IL-1F7 | IL37 | 0.0031 | 1.51 | 1.39 |
| Muellerian-inhibiting factor | MIS | AMH | 0.0033 | 1.50 | 1.52 |
| CD166 antigen | ALCAM | ALCAM | 0.0032 | 1.47 | 1.33 |
| Mediator of RNA polymerase II transcription subunit 1 | MED-1 | MED1 | 0.0091 | 1.46 | 1.41 |
| Ubiquitin-conjugating enzyme E2 G2 | UB2G2 | UBE2G2 | 0.0099 | 1.44 | 1.32 |
| Interleukin-13 receptor subunit alpha-1 | IL-13 Ra1 | IL13RA1 | 0.0040 | 1.44 | 1.50 |
| Immunoglobulin superfamily containing leucine-rich repeat protein 2 | ISLR2 | ISLR2 | 0.0060 | 1.43 | 1.37 |
| Cadherin-5 | Cadherin-5 | CDH5 | 0.0097 | 1.41 | 1.31 |
| Neurogenic locus notch homolog protein 1 | Notch 1 | NOTCH1 | 0.0020 | 1.41 | 1.32 |
| C-C motif chemokine 3-like 1 | LD78-beta | CCL3L1 | 0.002 | 1.35 | 1.30 |
| Tumor necrosis factor receptor superfamily member 21 | DR6 | TNFRSF21 | 0.0074 | 1.34 | 1.32 |
| Lymphotoxin alpha2:beta1 | Lymphotoxin a2/b1 | LTA LTB | 0.0004 | 1.33 | 1.32 |
| Epidermal growth factor receptor | ERBB1 | EGFR | 0.0082 | 1.29 | 1.29 |
| A disintegrin and metalloproteinase with thrombospondin motifs 13 | ATS13 | ADAMTS13 | 0.0026 | 1.29 | 1.41 |
| Carbonic anhydrase-related protein 10 | Carbonic Anhydrase X | CA10 | 0.0069 | 1.28 | 1.22 |
| Ectodysplasin-A, secreted form | EDA | EDA | 0.0042 | 1.27 | 1.28 |
| Neural cell adhesion molecule L1-like protein | CHL1 | CHL1 | 0.0046 | 1.27 | 1.35 |
| Repulsive guidance molecule A | RGMA | RGMA | 0.00150 | 1.26 | 1.24 |
| Sphingosine kinase 2 | SPHK2 | SPHK2 | 0.0061 | 1.24 | 1.22 |
| Endothelin-converting enzyme 1 | Endothelin-converting enzyme 1 | ECE1 | 0.0081 | 1.19 | 1.24 |
| Complement C2 | C2 | C2 | 0.0025 | 1.19 | 1.17 |
| Interleukin-1 Receptor accessory protein | IL-1 R AcP | IL1RAP | 0.0072 | 1.19 | 1.33 |
| Alpha-2-antiplasmin | a2-Antiplasmin | SERPINF2 | 0.0099 | 1.10 | 1.10 |
| Antithrombin-III | Antithrombin III | SERPINC1 | 0.0011 | 1.08 | 1.13 |

TABLE 4

Down-regulated proteins between third trimester
placenta accreta spectrum cases and controls
Decreased in Placenta Accreta Spectrum

| Target Full Name | Target | Entrez Symbol | p | Fold Change in Protein Expression Median | Mean |
|---|---|---|---|---|---|
| Gremlin-1 | GREM1 | GREM1 | 0.0099 | −1.34 | −1.41 |
| A disintegrin and metalloproteinase with thrombospondin motifs 1 | ATS1 | ADAMTS1 | 0.0095 | −1.46 | −1.38 |
| Calcium/calmodulin-dependent protein kinase kinase 1 | CaMKK alpha | CAMKK1 | 0.0098 | −1.70 | −1.82 |
| Plasminogen activator inhibitor 1 | PAI-1 | SERPINE1 | 0.0001 | −1.70 | −1.70 |
| Cryptic protein | CFC1 | CFC1 | 0.0068 | −1.74 | −1.59 |
| Cadherin-12 | Cadherin-12 | CDH12 | 0.0066 | −1.77 | −1.55 |
| DnaJ homolog subfamily B member 1 | HSP 40 | DNAJB1 | 0.0097 | −1.77 | −1.77 |
| Pescadillo homolog | PESC | PES1 | 0.0018 | −1.89 | −1.96 |
| Metalloproteinase inhibitor 3 | TIMP-3 | TIMP3 | 0.0026 | −2.04 | −2.04 |
| L-lactate dehydrogenase B chain | LDH-H 1 | LDHB | 0.0089 | −2.14 | −1.76 |
| Casein kinase II 2-alpha':2-beta heterotetramer | CK2-A2:B | CSNK2A2 CSNK2B | 0.0027 | −2.26 | −1.83 |
| Peroxiredoxin-6 | Peroxiredoxin-6 | PRDX6 | 0.0037 | −2.64 | −2.59 |
| Platelet factor 4 | PF-4 | PF4 | 0.0048 | −2.66 | −1.88 |

Figure 2:
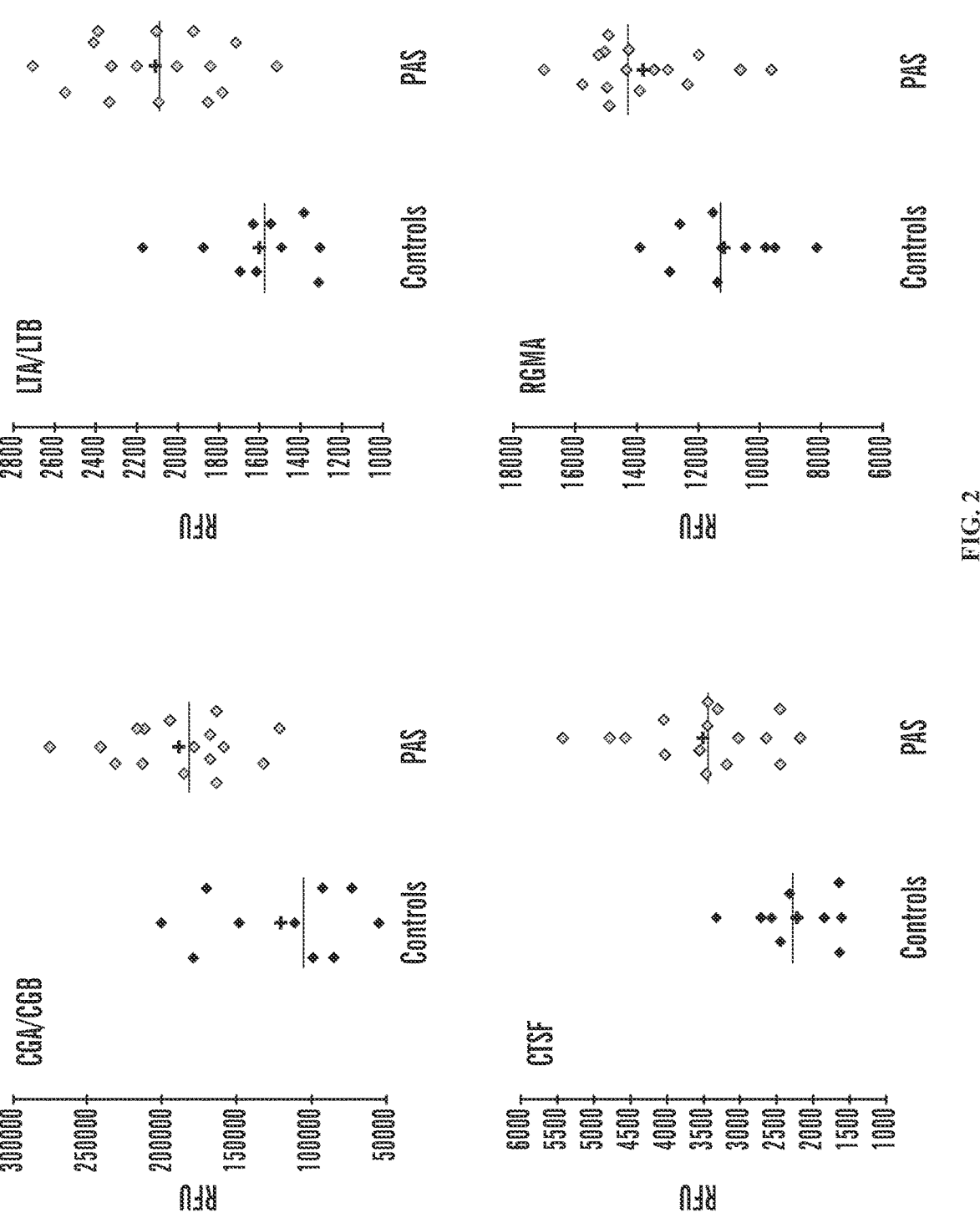
FIG. 2 comprises dot plots for differentially expressed proteins in PAS cases and controls. The expression patterns are presented of four representative proteins in placenta accreta spectrum cases and controls among the top 50 dysregulated proteins, using relative fluorescence units derived from SOMAscan®. Mean expression is depicted as "+" and median expression is indicated by a horizontal line.

In FIG. 2, dot plots of the cases and controls illustrate the difference in SOMAscan® expression levels for four representative targets: Chromogranins A and B (CGA and CGB), cathepsin F (CTSF), lymphotoxin alpha and lymphotoxin B (LTA/LTB), and repulsive guidance molecule bmp co-receptor A (RGMA) are included.

Figure 3A:
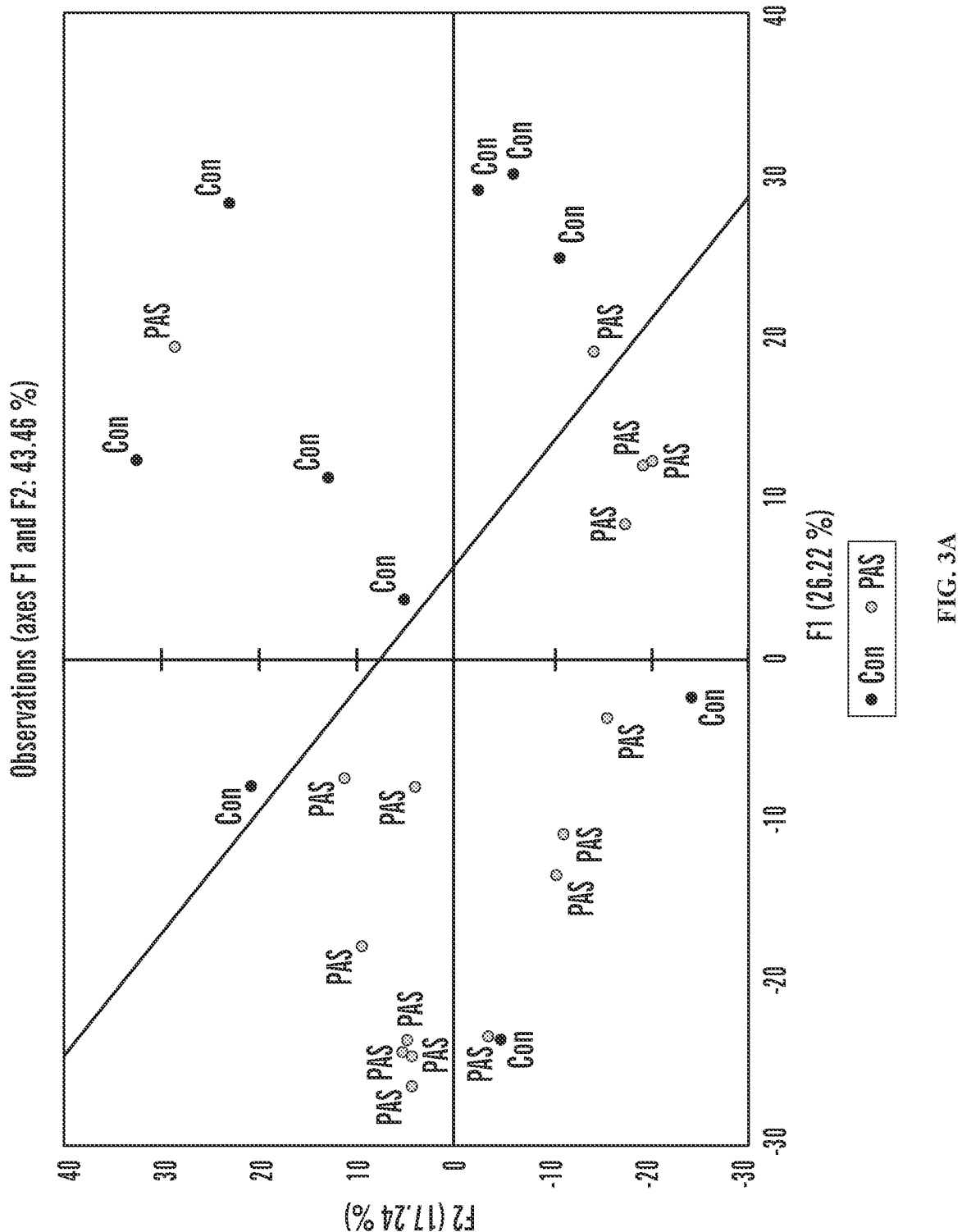
FIGS. 3A and 3B summarize Principal Component Analyses using all 1305 of the SOMAscan assay or the top 21 proteins that can be used to discriminate between PAS cases and controls.
Figure 3B:
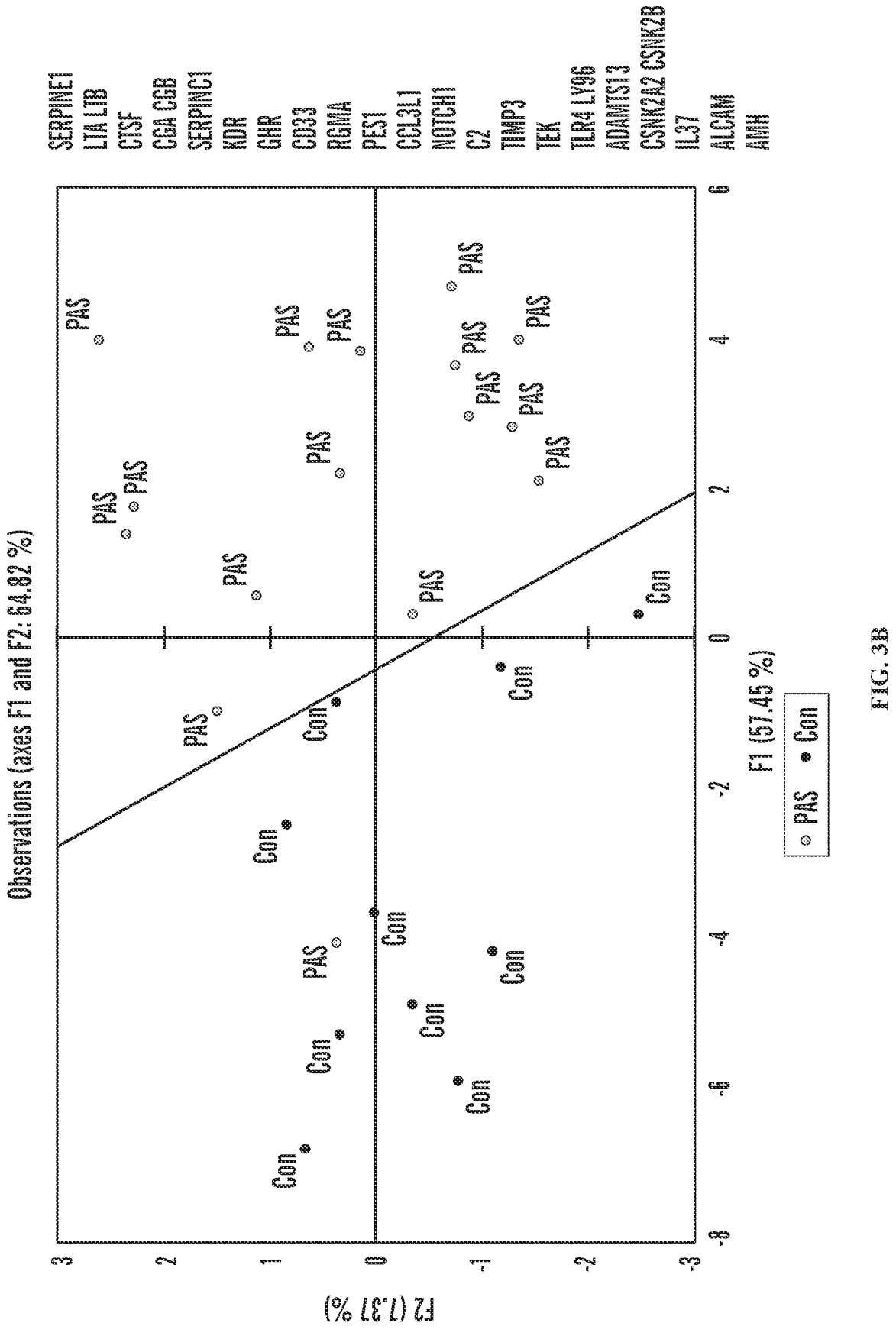
Figure 4:
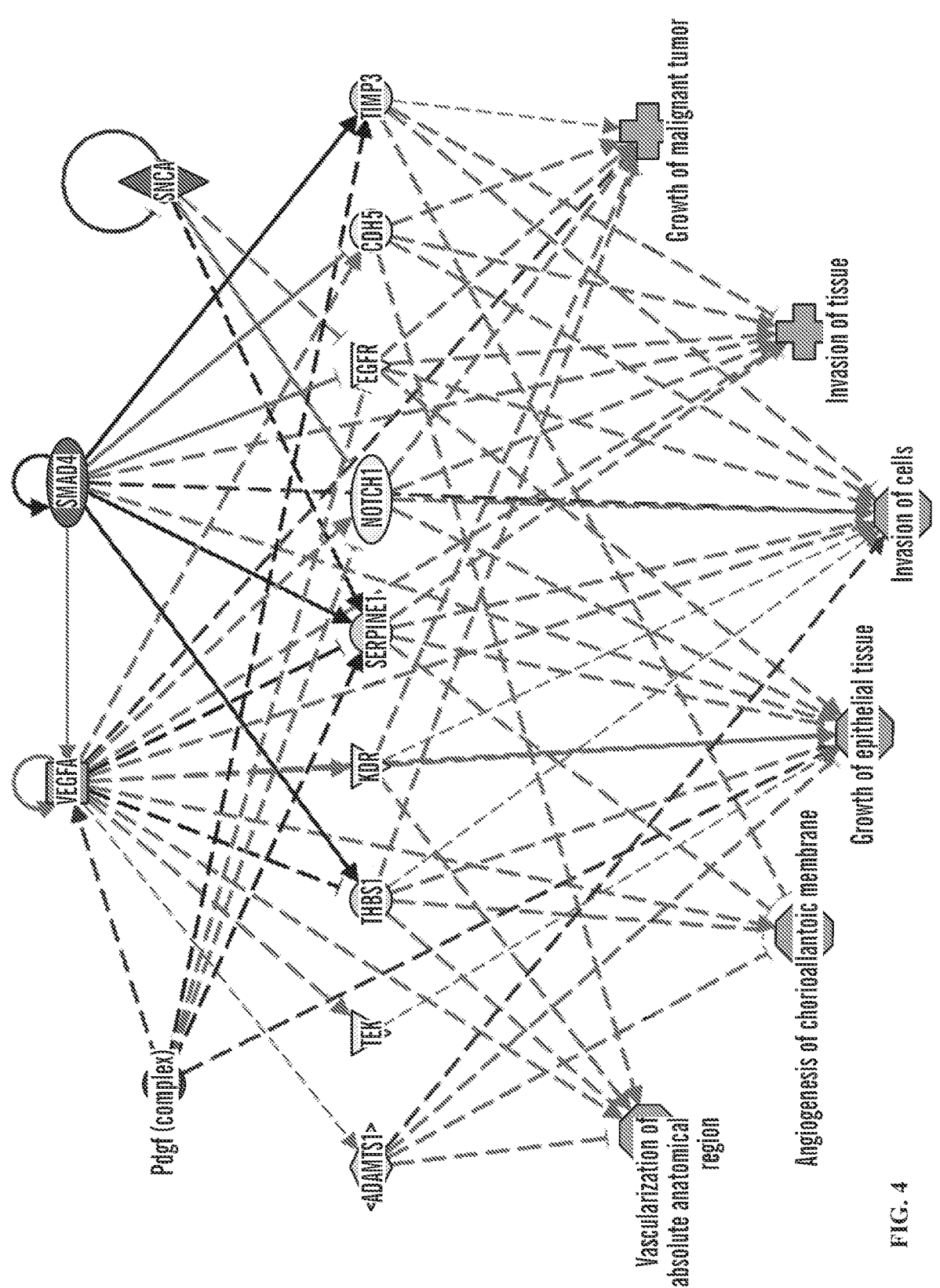
FIG. 4 is a diagram of a pathway analysis for PAS. Ingenuity Pathway Analyses demonstrate that gene products involved in regulating vascularization, angiogenesis, and invasion are abnormally represented in the plasma of PAS cases. Regulator effect analysis was performed to build the most statistically significant model of upstream regulators and their downstream targets combined with a prediction of potential biological effects. For each network, the central upstream regulator node (top row of proteins) is connected to PAS-associated proteins found by SOMAscan® analysis (middle row of proteins) and this combined interaction is predicted to regulate the biological functions indicated below the proteins. Orange lines represent activated states and blue lines represent inhibited states. Yellow represents indeterminate or if the experimental findings do not agree with the predicted effect. Green indicates decreased expression in PAS and red depicts increased expression. Red for the biological effects indicates enhanced activity.

Applying unsupervised principal component analysis to all samples using all 1,305 proteins resulted in excellent separation of PAS cases from the controls (FIG. 3A), with only 2 samples in each group clustering together with the wrong phenotype. This analysis demonstrates that the SOMAscan-derived proteomics data contain a significant component that differentiates between PAS cases and controls. Indeed, principal component analysis using the same 21 most dysregulated proteins as in FIG. 1A further highlights that the PAS cases can be accurately separated from controls based on this panel of proteins using the first two principal components (FIG. 3B). The first principal component accounts for 57% of the variance, and the second principal component for 7% of the variance. Ingenuity Pathway Analysis was performed using the 50 discovered proteins to obtain insights into the signaling pathways and biological mechanisms enriched significantly by the PAS-associated proteins. Modeling the links between proteins with differential expression based on their established associations with shared upstream regulatory proteins and downstream biological effects using the Regulator Effect analysis was particularly informative. The most significant Regulator Effect model that emerged from this analysis converged on SMAD4, PDGF, VEGF, and SNCA as upstream regulators of ADAMTS1, TIMP3, and several other proteins that were found to be associated with PAS, and predicted consequent effects on invasion, angiogenesis, and vascularization. These are the precise molecules and pathways involved in epithelial-mesenchymal transition, angiogenesis, and invasion noted in PAS (FIG. 4).

Figure 5A:
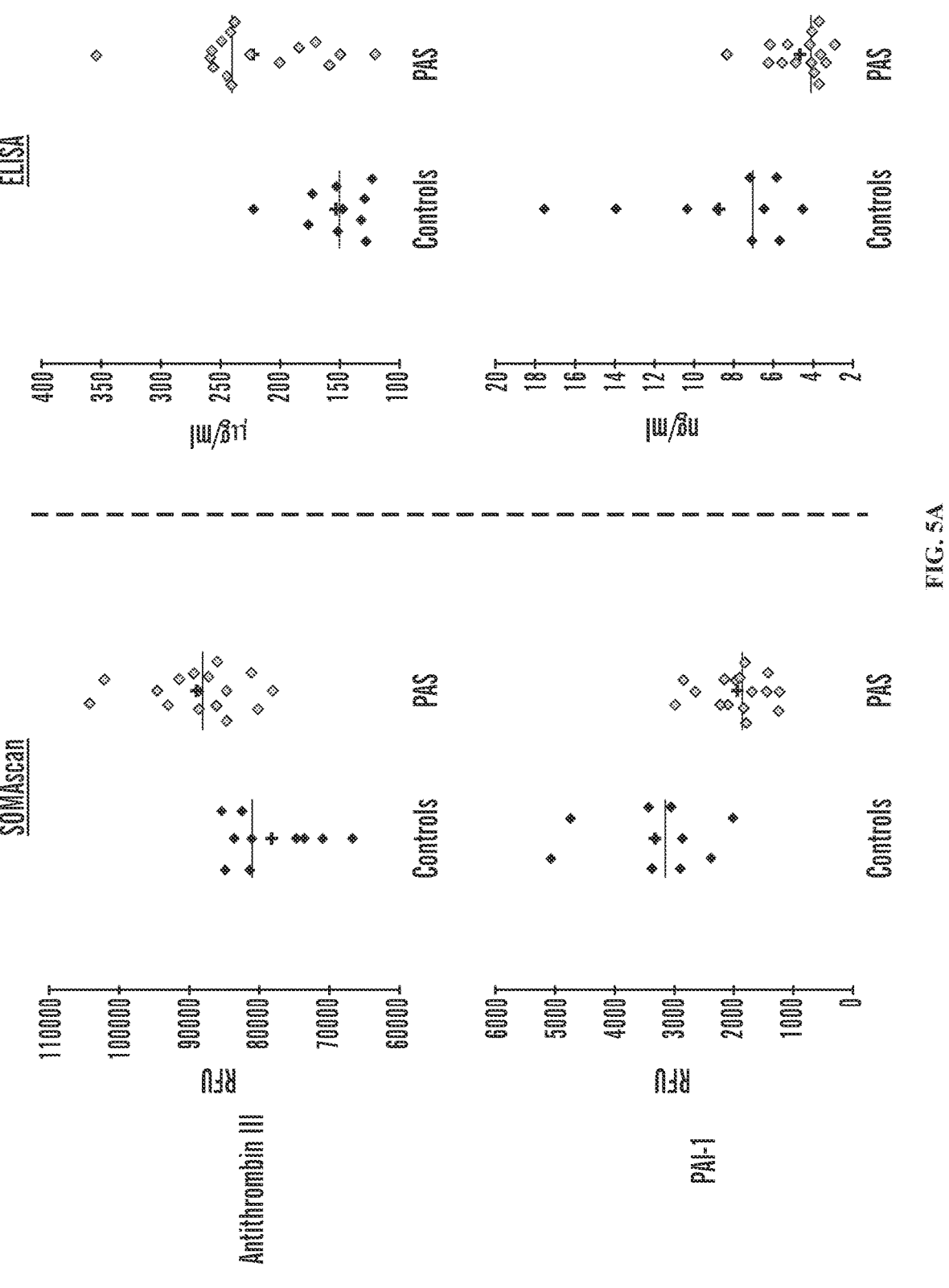
FIGS. 5A and 5B depict results obtained from SOMAs-can® and ELISA analyses for dysregulated proteins in PAS cases and controls.
Figure 5B:
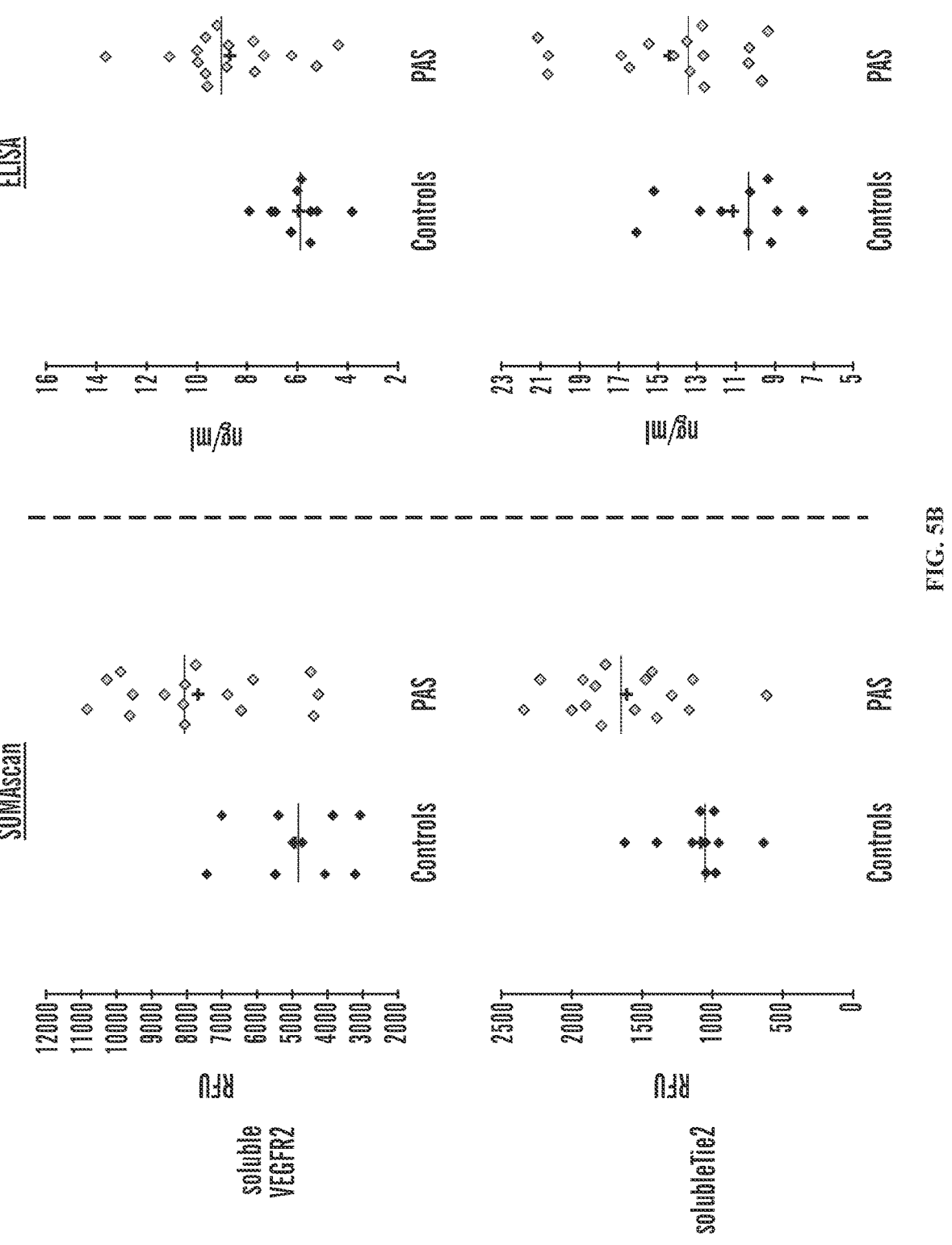

Using quantitative ELISA, the differential expression for four of the SOMAscan® targets for which commercially assays were available were validated (Table 5). The diagnostic accuracy as measured by the area under curve (AUC) was >0.75 for all four markers. The magnitude of the difference between cases and controls for the dysregulated molecules in PAS remained the same when restricting the analysis to cases and controls with previa (Table 6). ELISA data and SOMAscan® data for Antithrombin III (Serpin Family C Member 1 (SERPINC1)), PAI1 (SERPINE1), soluble VEGFR (KDR), and soluble Tie2 (TEK) show robust correlation between the two methods (FIGS. 5A and 5B).

TABLE 5

Plasma biomarker concentration among placenta
accreta spectrum cases compared with controls

| Biomarkers | Cases n = 16 Median IQR | Controls n = 10 Median IQR | P | Sensitivity 95% CI* | Specificity 95% CI* | Area under the curve 95% CI |
|---|---|---|---|---|---|---|
| Antithrombin III (SERPINC1), ug/ml | 240.4 177.9-253.8 | 150.3 130.2-174.5 | 0.002 | 0.75 0.48-0.93 | 0.90 0.55-1.0 | 0.86 0.71-1.0 |

TABLE 5-continued

| | Cases n = 16 Median IQR | Controls n = 10 Median IQR | P | Sensitivity 95% CI* | Specificity 95% CI* | Area under the curve 95% CI |
|---|---|---|---|---|---|---|
| Biomarkers | | | | | | |
| PAI-I (SERPINE1), ng/ml | 4.1 3.7-5.4 | 7.1 5.8-10.3 | <0.001 | 0.81 0.54-0.96 | 0.90 0.55-1.0 | 0.91 0.79-1.0 |
| Soluble VEGF R2 (KDR), ng/ml | 9.0 7.5-9.8 | 5.9 5.5-6.8 | 0.003 | 0.81 0.54-0.96 | 0.90 0.55-1.0 | 0.84 0.68-1.0 |
| Soluble Tie2, ng/ml | 13.5 11.6-16.8 | 10.4 9.3-12.9 | 0.02 | 0.75 0.48-0.93 | 0.70 0.35-0.93 | 0.77 0.57-0.96 |

Plasma biomarker concentration among placenta accreta spectrum cases compared with controls P values were obtained using Wilcoxon rank sum test.

*Sensitivity and specificity are reported for the biomarker value that maximized both sensitivity and specificity.

IQR: interquartile range;

CI: confidence interval

TABLE 6

Plasma biomarker concentration among placenta accreta spectrum cases with placenta previa compared with controls with placenta previa

| Biomarkers | Cases n = 13 | Controls n = 4 | P |
|---|---|---|---|
| Antithrombin III (SERPINC1), ug/ml | 239.4 184.7-249.5 | 150.3 135.8-164.5 | 0.03 |
| PAI-I (SERPINE1), ng/ml | 4.1 3.7-5.2 | 6.1 5.2-6.8 | 0.04 |
| Soluble VEGF R2 (KDR), ng/ml | 9.1 7.3-9.7 | 6.5 5.0-6.9 | 0.06 |
| Soluble Tie2, ng/ml | 13.6 12.7-16.6 | 9.9 9.2-11.1 | 0.02 |

Data are presented as median and interquartile range. P values were obtained using Wilcoxon rank sum test.

Using a novel proteomics platform, evidence is presented that shows subjects with PAS disorder have a unique plasma protein signature. Pathway analyses suggest that gene products regulating coagulation, angiogenesis, invasion, and inflammation are particularly over-represented in the circulation of subjects with PAS. Several of the dysregulated proteins were confirmed using an independent validated ELISA, indicating that many of these are potential biomarkers for this condition. Interestingly, all four of the analytes that were confirmed showed promise for potential use as a diagnostic test as evidenced by AUC >0.75. However, it has become more apparent that no single biomarker is likely to demonstrate the diagnostic accuracy and AUC needed for a diagnostic test. A multi-marker test is anticipated the diagnostic with the highest accuracy and AUC for PAS. One third trimester PAS case had a plasma proteome similar to controls. Whether this was related to misclassification of the disease or different phenotypes of the disease spectrum remains unknown. Since most PAS cases had accompanying placenta previa, a sub-group analysis restricted to those with placenta previa was performed. The protein signature in plasma remained specific for PAS. Proteins with known roles in invasion, inflammation, and angiogenesis were well-represented among the proteins with the highest degree of dysregulation between pregnancies with and without PAS.

The proteomics studies described herein reveal dysregulation of a new cadre of proteins, some of which have been implicated in a number of overlapping pathways that may be relevant to the pathogenesis of abnormal placentation. During normal placentation, extravillous trophoblast cells do not invade beyond the inner third of the myometrium.

This highly regulated process depends on complex crosstalk between decidua and endothelial and smooth muscle cells of maternal blood vessels, and the invading placental trophoblast. Development of PAS occurs upon dysregulation of this process, allowing inappropriate invasion of trophoblasts beyond the decidua to (or beyond) the myometrium, but little is known about the underlying molecular pathways Of particular interest is upregulation of TEK (also known as soluble Tie2), a receptor tyrosine kinase highly expressed by endothelial cells and known to be critical for normal development of blood vessels and endothelial cell homeostasis. Excessive TEK signaling causes abnormal blood vessel formation, and a particular gain-of-function mutation in TEK has been implicated in the development of inherited venous malformations. Although VEGF signaling has been at the center of the majority of studies of angiogenesis in the context of development and tumor biology, the appearance of TEK among the dysregulated proteins in this study of participants with PAS reminds us that it too has an important role in endothelial cell signaling worth further exploration.

Other proteins that appeared among the most differentially expressed in the presently disclosed study include Notch1, which was upregulated in PAS. Notch1 is a receptor found on the endothelial cell surface and known to have a critical signaling role in embryonic angiogenesis. Tissue inhibitor of metalloproteinase 3 (TIMP3) was significantly downregulated in PAS cases. TIMP3 interferes with the ability of VEGF to interact with VEGF-R, and silencing of TIMP3 has been observed to promote angiogenesis in mice. Thus, the observation of decreased TIMP3 is also consistent with a pro-angiogenic environment in PAS cases. TIMP3 is also downregulated in advanced stage cancers, thereby promoting cellular invasion and inflammation. PAS has similar phenotypic features of advanced cancer, such as the dysregulation of angiogenesis and invasion. Similarly, ADAMTS1, another matrix metalloproteinase capable of disrupting angiogenesis, was down-regulated.

Third trimester PAS cases were found to have decreased levels of SERPINE1, also known as plasminogen activator inhibitor 1 or PAI-1. By blocking the activation of plasminogen to plasmin, SERPINE1 promotes the survival of fibrin, which recruits and activates signaling pathways that promote angiogenesis including VEGF and TGF-B. Higher expression of SERPINE1 by tumors tends to correlate with more metastases and worse survival. Downregulation of SERPINE1 in third trimester PAS cases may actually attenuate angiogenesis, perhaps reflecting a compensatory change rather than a pathogenic one.

It is notable that the combined fingerprint of decreased expression of PAI-1 and TIMP-3 with increased expression of VEGF sR2 and Tie-2 in PAS represents the mirror image of results reported in a study in which the SOMAscan proteomics platform was applied to plasma from women who presented with early signs of preeclampsia. Conceptually, it is not surprising to see that a set of proteins that can modulate angiogenesis regulated in opposite directions across the two clinical conditions, given that preeclampsia is thought to stem from inadequate placental invasion and hypoperfusion while PAS is a state of excessive invasion and unchecked angiogenesis. Prior expression studies with soluble fms-like tyrosine kinase 1 in PAS is consistent with this hypothesis.

Proteins that are key players in inflammatory signaling and the coagulation cascade also appeared prominently among the top SOMAscan® hits, which reflect other critical functions of endothelial cells. Third trimester PAS cases were observed to have upregulated anti-inflammatory proteins including SERPINC1 (also known as antithrombin III), a serine protease inhibitor with an important anti-coagulant role. SERPINC1 also has prominent anti-inflammatory activity in ischemia-reperfusion injury, where it attenuates inflammation via upregulation of PGI2. Upregulation of RGMA, a membrane glycoprotein that has a role in the resolution of inflammation, was observed, potentially contributing to an anti-inflammatory environment. Downregulation of von Willebrand factor, a marker of endothelial activation and circulating coagulation factor that promotes vascular inflammation, is also a potential contributor to an anti-inflammatory environment.

Platelet factor 4 (PF4) is another protein found to be downregulated in PAS. PF4 is a protein released by activated platelets that has a pro-coagulant role via inhibition of the interaction between thrombin and antithrombin III. PF4 has also been noted to have anti-angiogenic effects, possibly by interfering with VEGF receptor-ligand interactions. Downregulation of PF4 in PAS indicates that suppression of its pro-coagulant role could be pathogenically important in PAS.

Immunological molecules also were detected in this initial screen. In particular, upregulation of IL37, complement component 8 (C8), and Lymphotoxin A2/B1 indicates that both innate and adaptive immunity may be involved in the pathogenesis of PAS.

The incidence of PAS is rising. Even with the very best prenatal care and imaging modalities, a substantial proportion of cases are missed or diagnosed late, resulting in significant maternal morbidity. The novel diagnostic paradigm that utilizes biomarkers in conjunction with imaging and other clinical tools presented herein is a significant improvement in detecting PAS. As reported herein, several soluble proteins in the maternal plasma are differentially expressed and could be used for early diagnosis of PAS. Even with a limited sample size, diagnostic performances of the 4 biomakers that were confirmed by ELISA were robust and suggested that they could be used as a part of a diagnostic panel. Furthermore, many of these protein markers may contribute to disease pathogenesis. For example, it is possible that some of the endothelial cell proteins that were upregulated in PAS were enriched simply because of the enlarged vascular bed that is present in the setting of placental invasion. With a significantly greater volume of endothelial cells a higher detectable level of their secreted proteins and turnover byproducts is expected. However, some of the proteins, such as sTie2, could contribute to abnormal placental vascular lakes observed in PAS, as the vascular phenotype is similar to what is described in patients with genetic mutations in the Tie2 pathway. Strengths of this study include the use of prospectively collected and well-phenotyped specimens and an innovative platform that tested a large number of proteins in an unbiased fashion. Another strength is the validation of four dysregulated proteins using an independent and validated ELISA method. It may be useful to combine ultrasound findings with biomarker data to provide a more accurate estimation of risk and prognosis.

In summary, this analysis identified several novel plasma proteins using an aptamer-based proteomic platform that may prove useful for the prediction and early diagnosis of the disorder. Anti-thrombin III, PAI-1, soluble Tie2 and soluble VEGFR receptor 2 were identified as novel biomarkers for PAS.

Example 2: Second Trimester PAS Biomarkers

Figure 6:
FIG. 6 is a heatmap depicting plasma protein expression that shows relative minimum and maximum expression levels for each protein as quantified by SOMAscan® (p<0.01). Comparisons were made between all second trimester PAS cases and controls.
Figure 6:
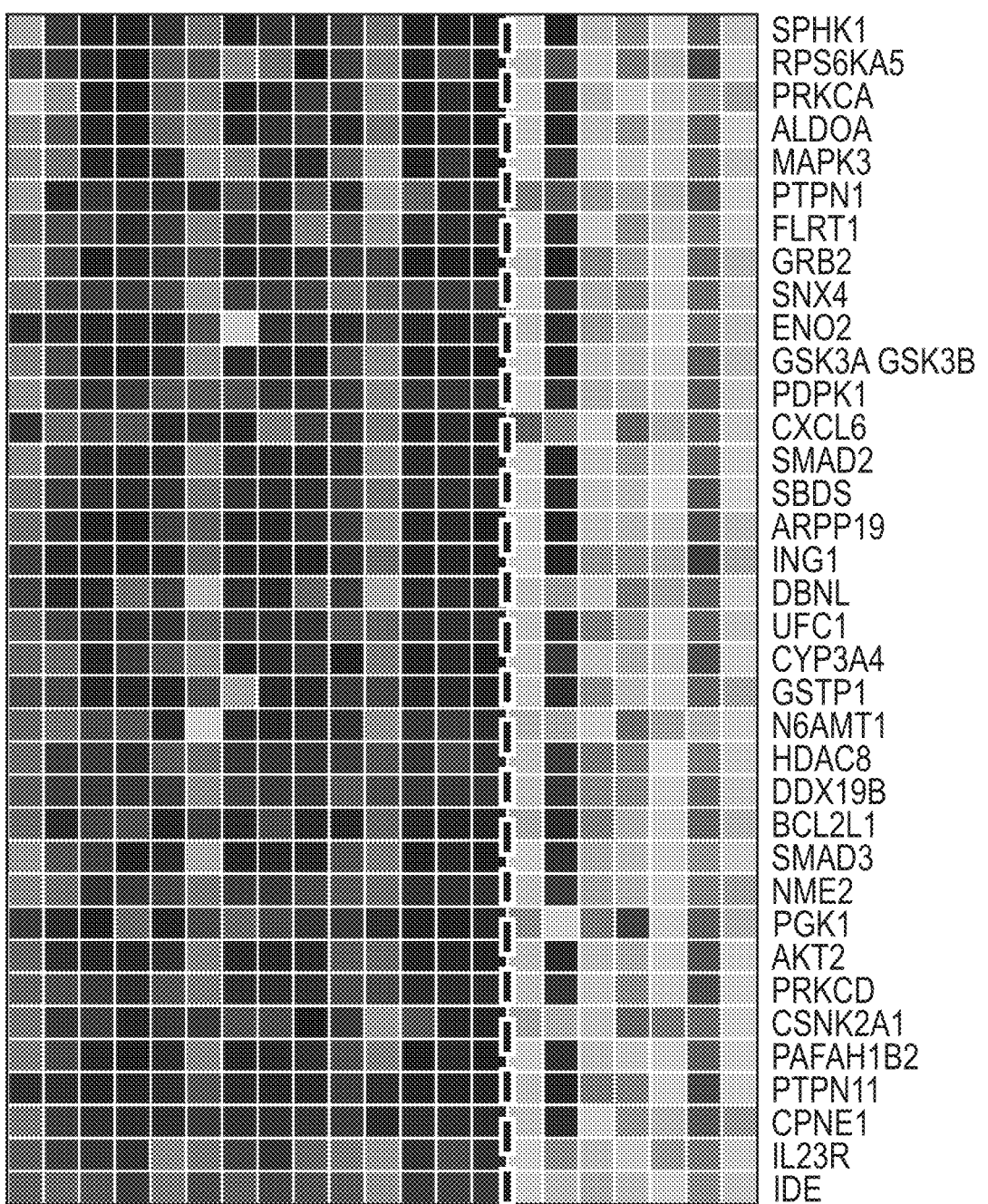
Figure 7:
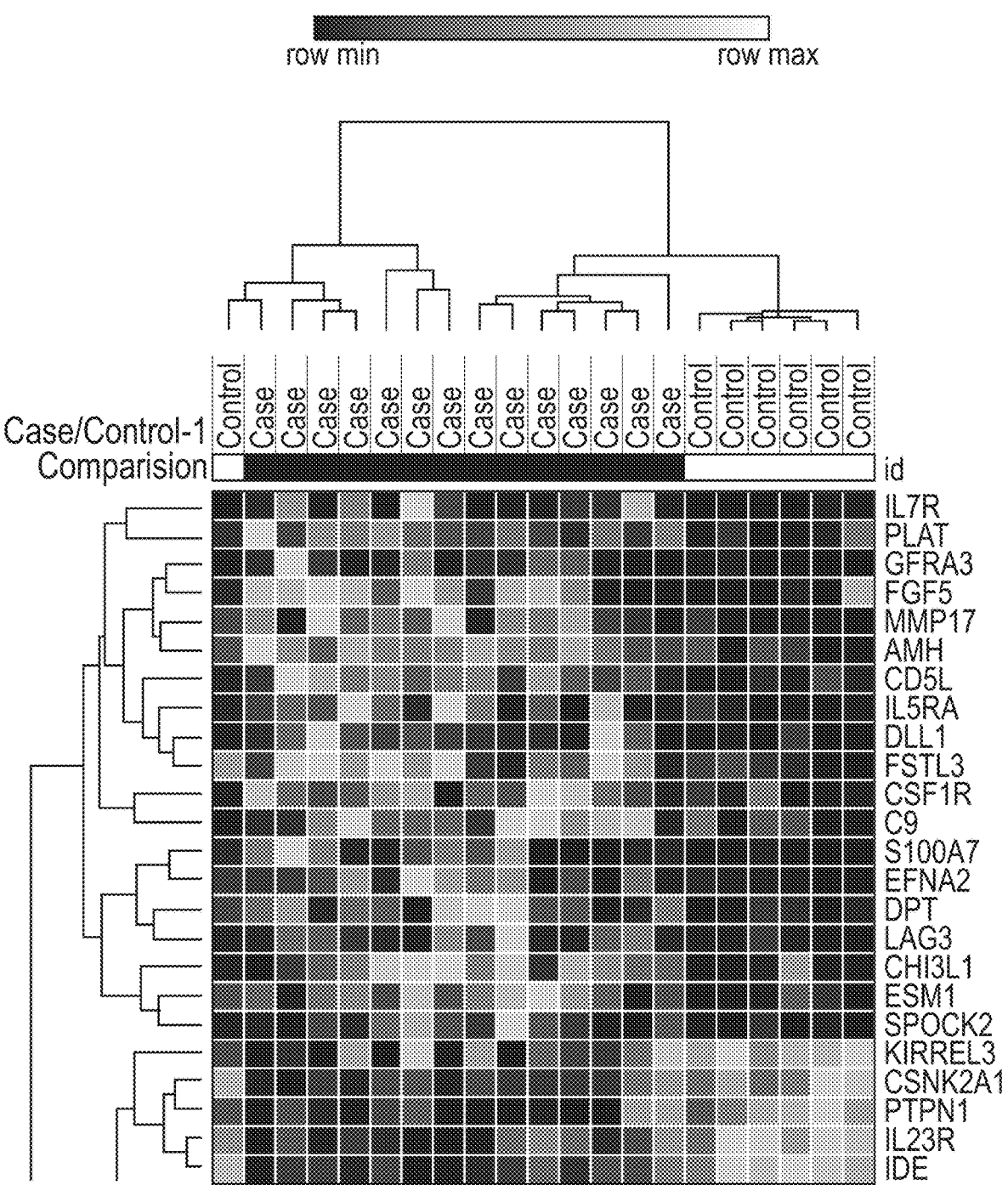
FIG. 7 is a heatmap with hierarchical clustering depicting plasma protein expression in second trimester PAS cases with placenta previa and controls. The relative minimum and maximum expression levels for each protein as quantified by SOMAscan® (p<0.01) are shown.
Figure 7:
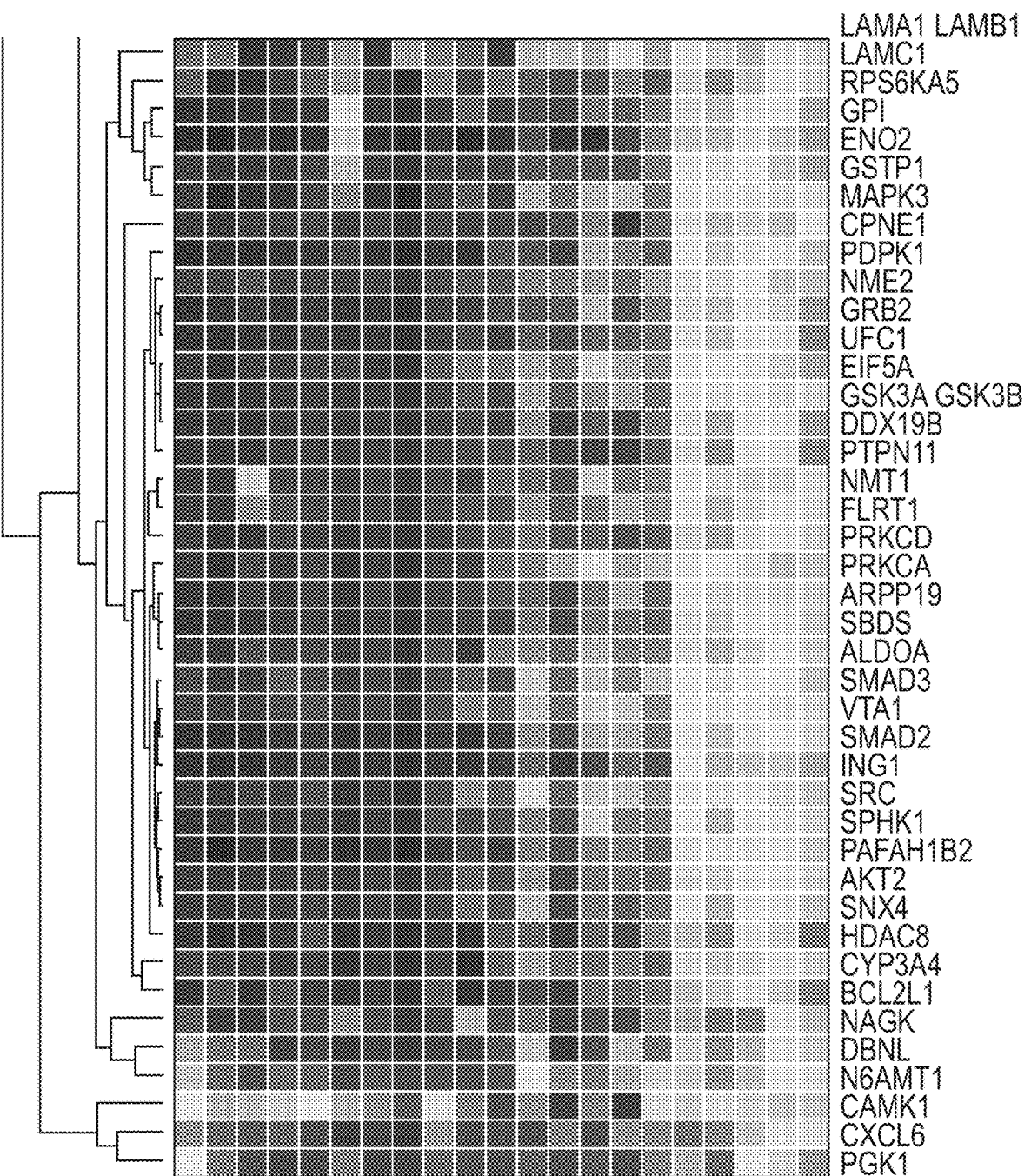
Figure 8:
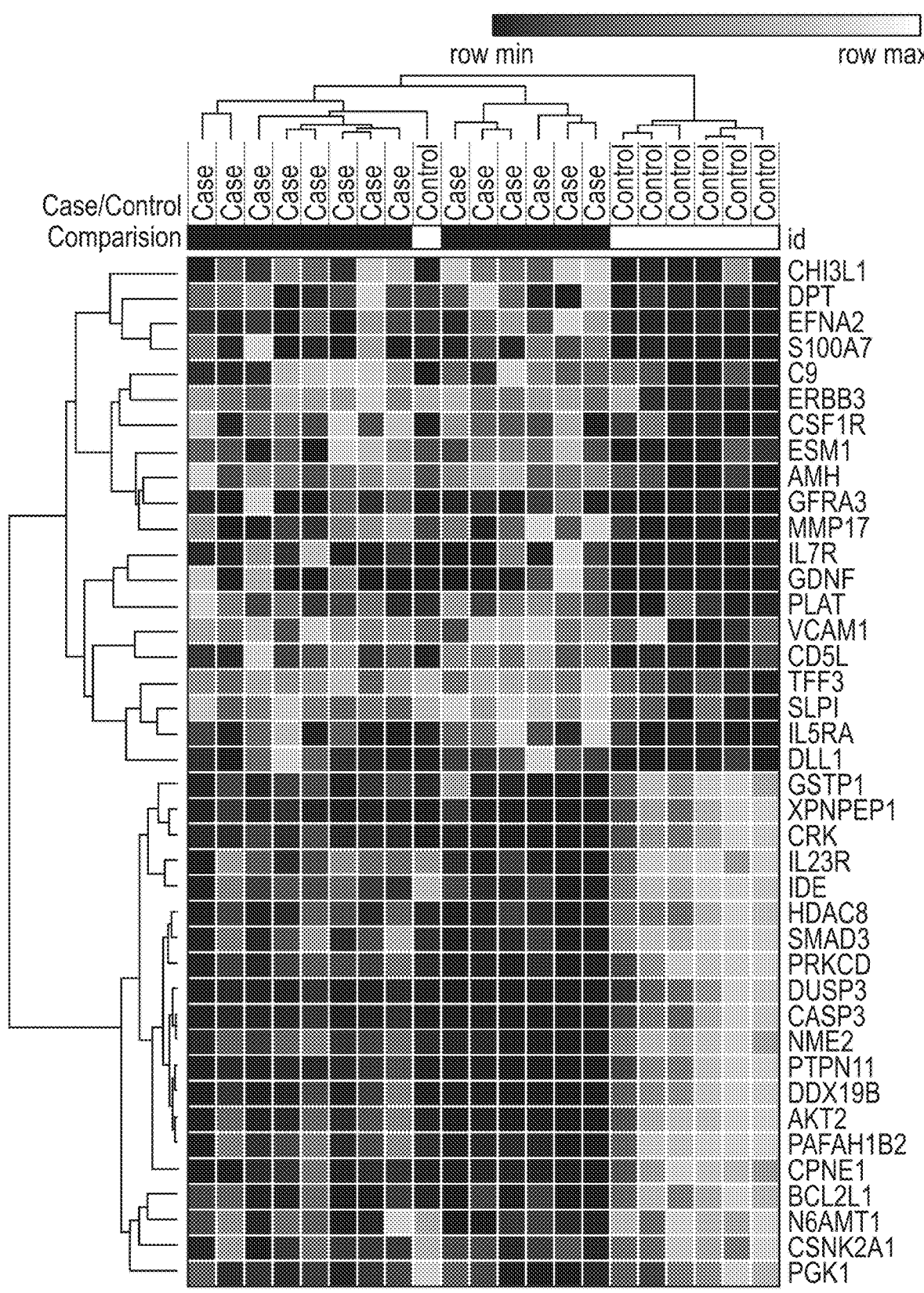
FIG. 8 is a heatmap of the top 40 proteins with hierar-chical clustering depicting plasma protein expression in second trimester PAS cases with placenta previa and con-trols.

SOMAscan® analysis identified plasma proteins with expression levels that were significantly different (all $p<0.01$) between second trimester PAS cases (n=14) and controls with placenta previa (n=7). (FIG. 6). This analysis was restricted to participants who had concomitant placenta previa. This data was used in hierarchical analysis, which shows clustering of subgroups of the identified biomarkers (FIG. 7), and the top 40 proteins identified in this analysis are shown in FIG. 8.

The proteins identified as differentially expressed were as follows: Anti-Mullerian Hormone (AMH), CD5 Molecule Like (CD5L), Interleukin 7 Receptor (IL7R), Matrix Metallopeptidase 17 (MMP17), Complement C9 (C9), Chitinase 3 Like 1 (CHI3L1), Endothelial Cell Specific Molecule 1 (ESM1), GDNF Family Receptor Alpha 3 (GFRA3), Plasminogen Activator, Tissue Type (PLAT), S100 Calcium Binding Protein A7 (S100A7), Colony Stimulating Factor 1 Receptor (CSF1R), Ephrin A2 (EFNA2), Dermatopontin (DPT), Delta Like Canonical Notch Ligand 1 (DLL1), Interleukin 5 Receptor Subunit Alpha (IL5RA), Lymphocyte Activating 3 (LAG3), Follistatin Like 3 (FSTL3), Fibroblast Growth Factor 5 (FGF5), SPARC (Osteonectin, Cwcv And Kazal Like Domains Proteoglycan 2 (SPOCK2), Laminin Subunit Alpha 1 (LAMAI Laminin Subunit Beta 1 (LAMB1 Laminin Subunit Gamma 1 (LAMC1), Kirre Like Nephrin Family Adhesion Molecule 3 (KIRREL3), Calcium/Calmodulin Dependent Protein Kinase I (CAMK1), SRC Proto-Oncogene, Non-Receptor Tyrosine Kinase (SRC), Glucose-6-Phosphate Isomerase (GPI), N-Acetylglucosamine Kinase (NAGK), Eukaryotic Translation Initiation Factor 5A (EIF5A), N-Myristoyltransferase 1 (NMT1), Vesicle Trafficking 1 (VTA1), Sphingosine Kinase 1 (SPHK1), Ribosomal Protein S6 Kinase A5 (RPS6KA5), Protein Kinase C Alpha (PRKCA), Aldolase, Fructose-Bisphosphate A (ALDOA), Mitogen-Activated Protein Kinase 3 (MAPK3), Protein Tyrosine Phosphatase Non-Receptor Type 1 (PTPN1), Fibronectin Leucine Rich Transmembrane Protein 1 (FLRT1), Growth Factor Receptor Bound Protein 2 (GRB2), Sorting Nexin 4 (SNX4), Enolase 2 (ENO2), Glycogen Synthase Kinase 3 Alpha (GSK3A Glycogen Synthase Kinase 3 Beta (GSK3B), 3-Phosphoinositide Dependent Protein Kinase 1 (PDPK1), C—X—C Motif Chemokine Ligand 6 (CXCL6), SMAD Family Member 2 (SMAD2), SBDS Ribosome Maturation Factor (SBDS), CAMP Regulated Phosphoprotein 19 (ARPP19), Inhibitor Of Growth Family Member 1 (ING1), Drebrin Like (DBNL), Ubiquitin-Fold Modifier Conjugating Enzyme 1 (UFC1), Cytochrome P450 Family 3 Subfamily A Member 4 (CYP3A4), Glutathione S-Transferase Pi 1 (GSTP1), N-6 Adenine-Specific DNA Methyltransferase 1 (N6AMT1), Histone Deacetylase 8 (HDAC8), DEAD-Box Helicase 19B (DDX19B), BCL2 Like 1 (BCL2L1), SMAD Family Member 3 (SMAD3), NME/NM23 Nucleoside Diphosphate Kinase 2 (NME2), Phosphoglycerate Kinase 1 (PGK1), AKT Serine/Threonine Kinase 2 (AKT2), Protein Kinase C Delta (PRKCD), Casein Kinase 2 Alpha 1 (CSNK2A1), Platelet Activating Factor Acetylhydrolase 1b Catalytic Subunit 2 (PAFAHIB2), Protein Tyrosine Phosphatase Non-Receptor Type 11 (PTPN11), Copine 1 (CPNE1), Interleukin 23 Receptor (IL23R), and Insulin Degrading Enzyme (IDE).

Figure 9:
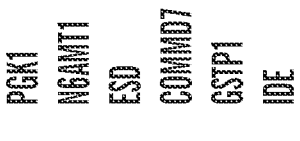
FIG. 9 is a scatter plot summarizing the principal com-ponent analysis of PGK1, N6AMT1, ESD, COMMD7, GSTP1, and IDE for second trimester PAS cases and con-trols.
Figure 10:
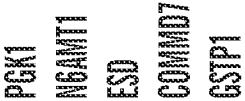
FIG. 10 is a scatter plot summarizing the principal com-ponent analysis of PGK1, N6AMT1, ESD, COMMD7, and GSTP1 for second trimester PAS cases and controls.
Figure 11:
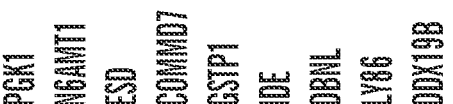
FIG. 11 is a scatter plot summarizing the principal com-ponent analysis of PGK1, N6AMT1, ESD, COMMD7, GSTP1, IDE, DBNL, LY86, and DDX19B for second tri-mester PAS cases and controls.
Figure 12:
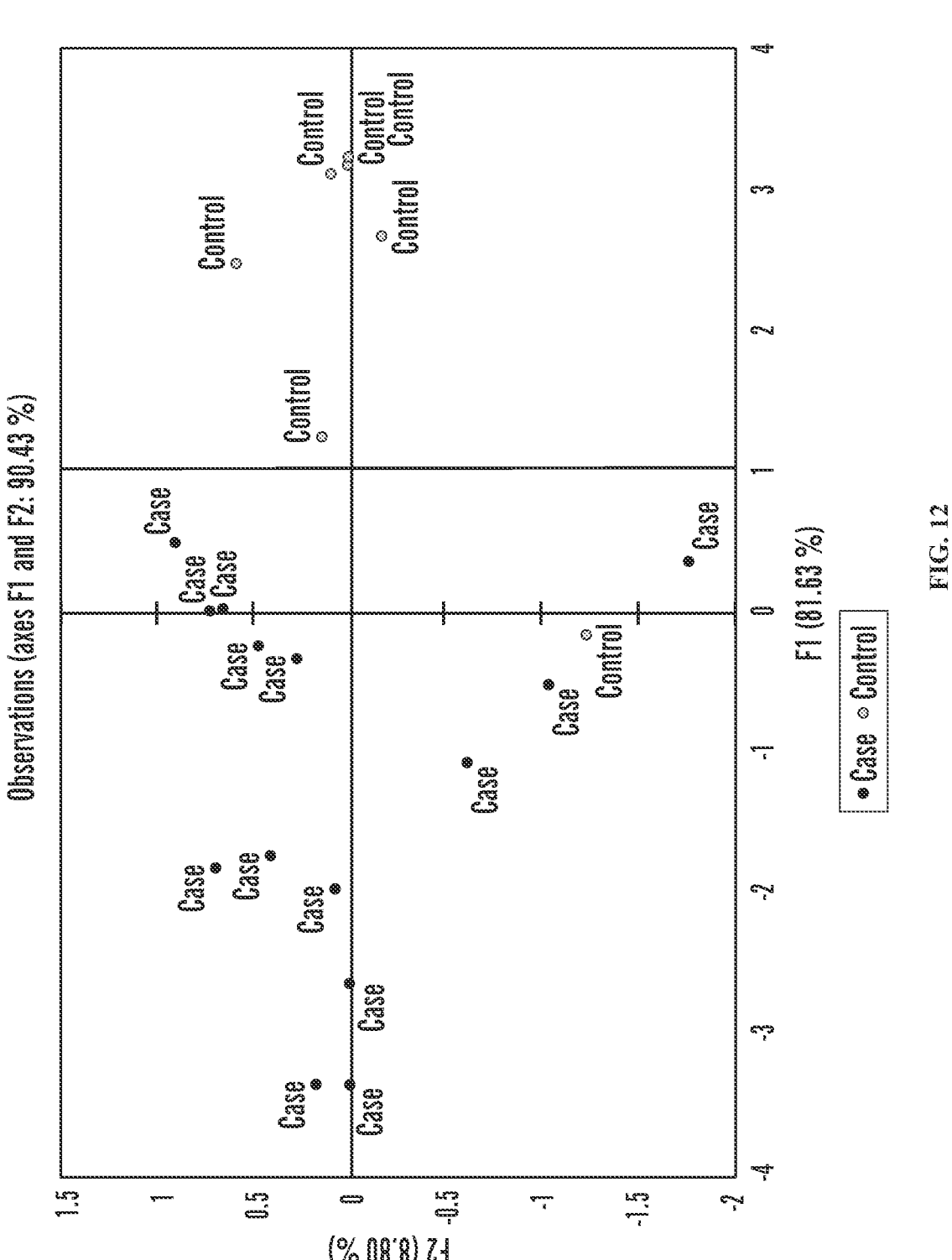
FIG. 12 is a scatter plot summarizing the principal component analysis of IDE, IL23R, CPNE1, XPNPEP1, and PAFAHIB2 for second trimester PAS cases with placenta previa and controls.
Figure 13:
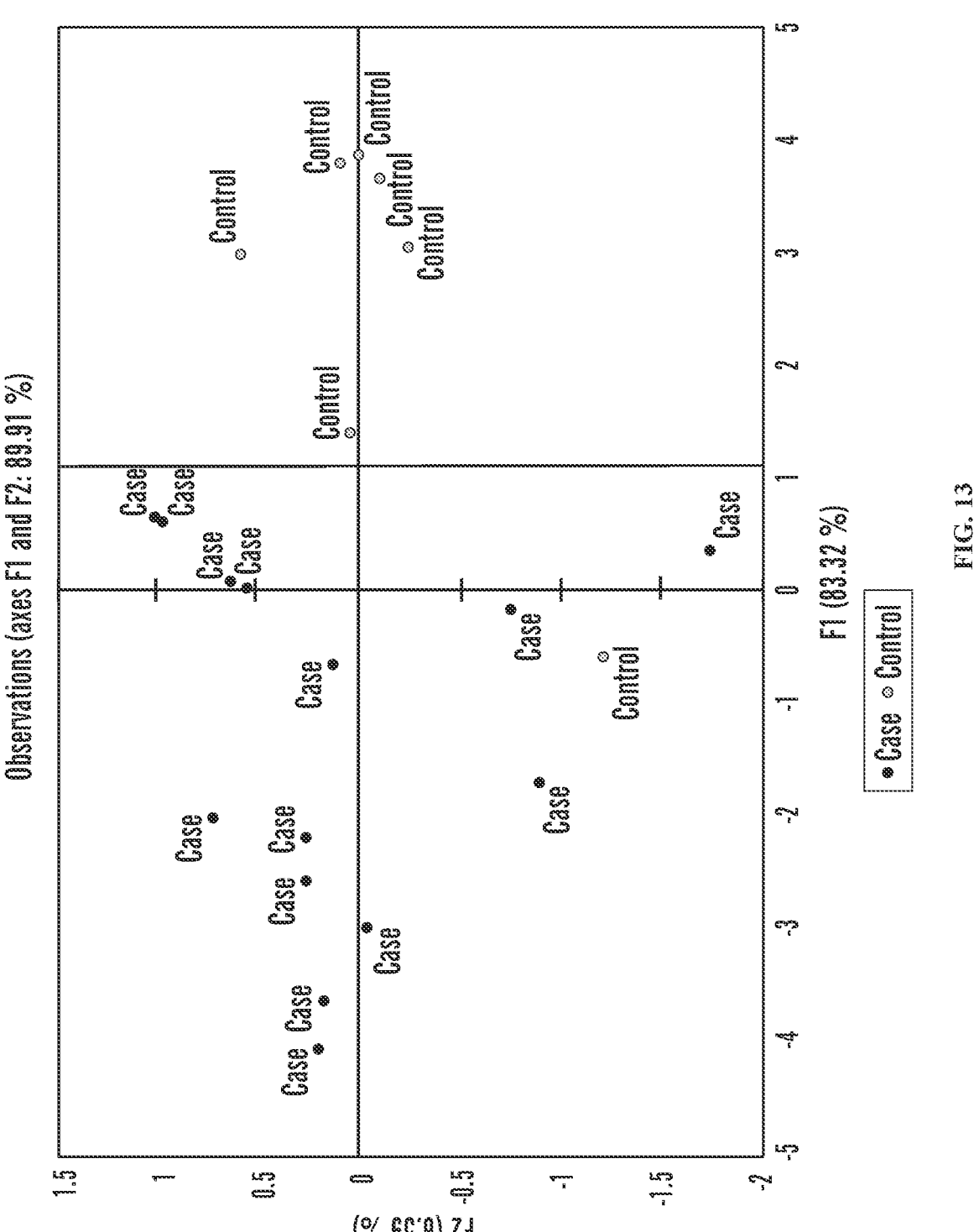
FIG. 13 is a scatter plot summarizing the principal component analysis of IDE, IL23R, CPNE1, XPNPEP1, PAFAHIB2, PTPN11, and PRKCD for second trimester PAS cases with placenta previa and controls.
Figure 14:
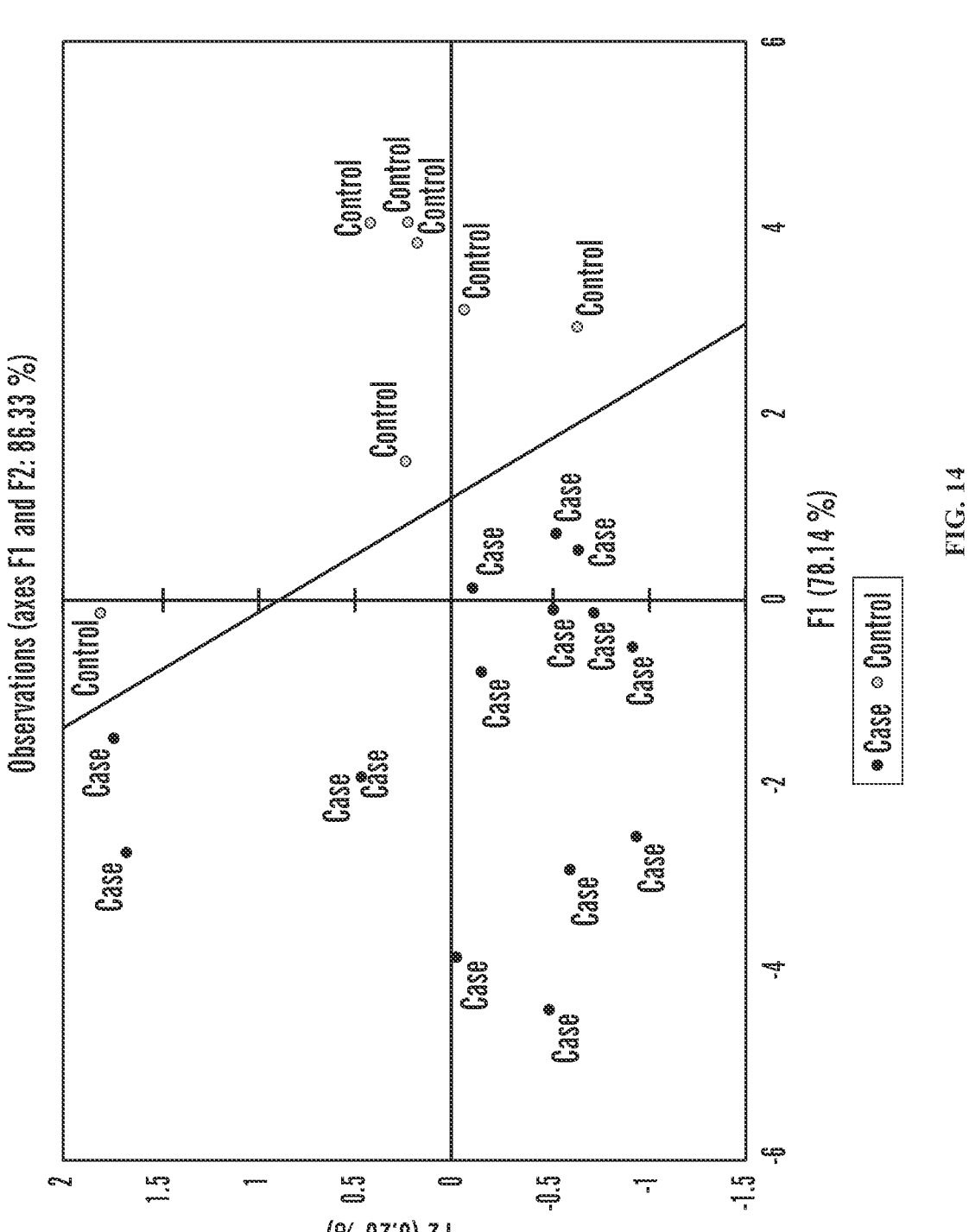
FIG. 14 is a scatter plot summarizing the principal component analysis of IDE, IL23R, CPNE1, XPNPEP1, PAFAHIB2, PTPN11, PRKCD, and PGK1 for second trimester PAS cases and controls.

Principal component analysis was used to identify subsets of proteins whose expression can be used to distinguish second trimester PAS cases from control. Referring to FIGS. 9-11, primary component analyses showed that the differential expression of the following sets of markers could be used to distinguish patients having or likely to develop PAS: PGK1, N6AMT1, ESD, COMMD7, GSTP1, and IDE; PGK1, N6AMT1, ESD, COMMD7, and GSTP1; and PGK1, N6AMT1, ESD, COMMD7, GSTP1, IDE, DBNL, LY86, and DDX19b;

Referring to FIGS. 12-14, principal component analyses showed that the expression of sets of proteins could be used to distinguish subjects in their second trimester having or likely to develop PAS. For example, expression of IDE, IL23R, CPNE1, XPNPEP1, and PAFAHIB2; IDE, IL23R, CPNE1, XPNPEP1, PAFAHIB2, PTPN11, and PRKCD; and IDE, IL23R, CPNE1, XPNPEP1, PAFAHIB2, PTPN11, PRKCD, and PGK1 distinguished second trimester cases of PAS with placenta previa from controls.

Figure 15:
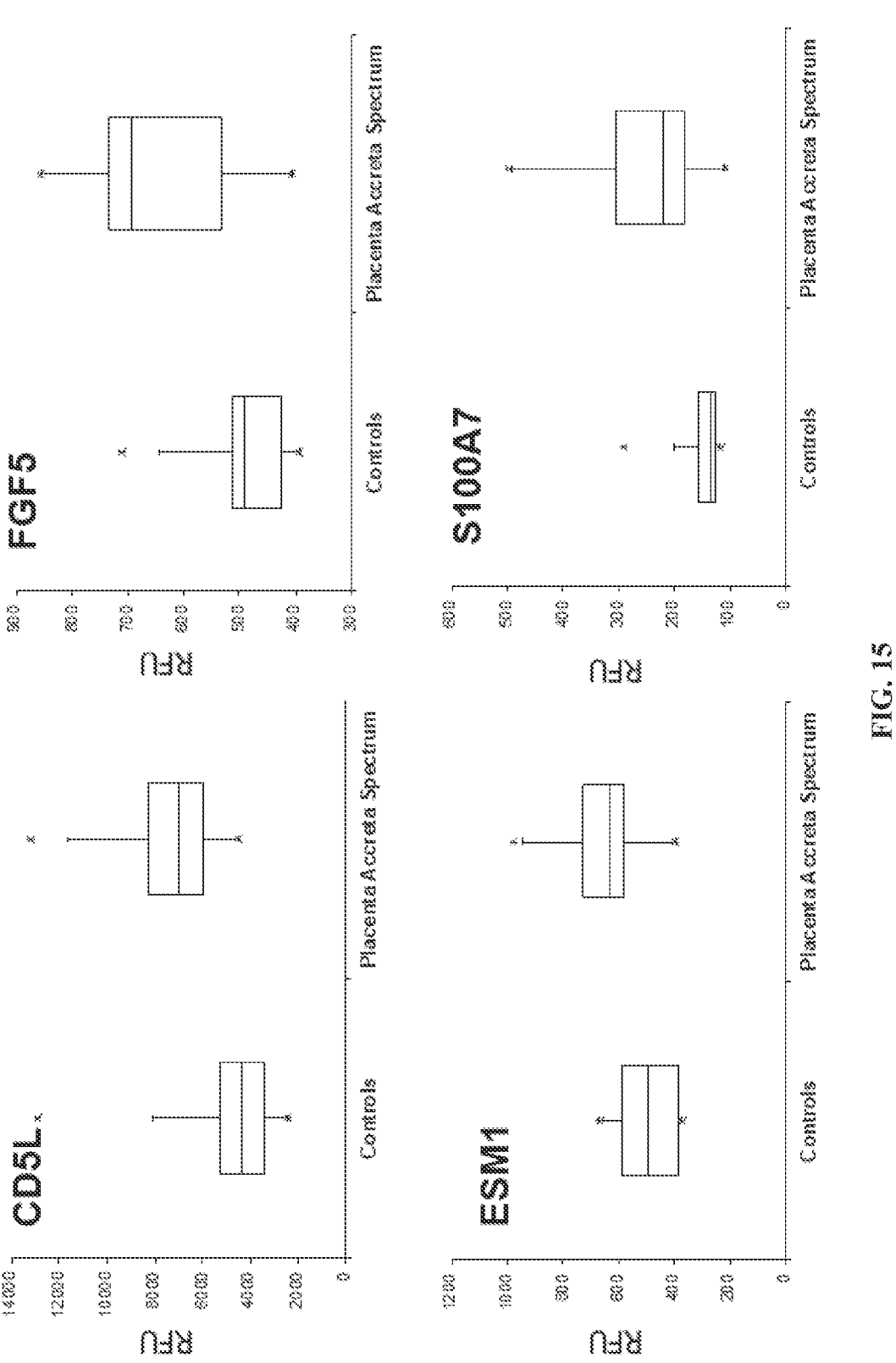
FIG. 15 comprises box whisker plots comparing the relative protein expression of CD5L, FGF5, ESM1, and S100A7 detected in plasma samples obtained from second trimester PAS cases and controls.
Figure 16:
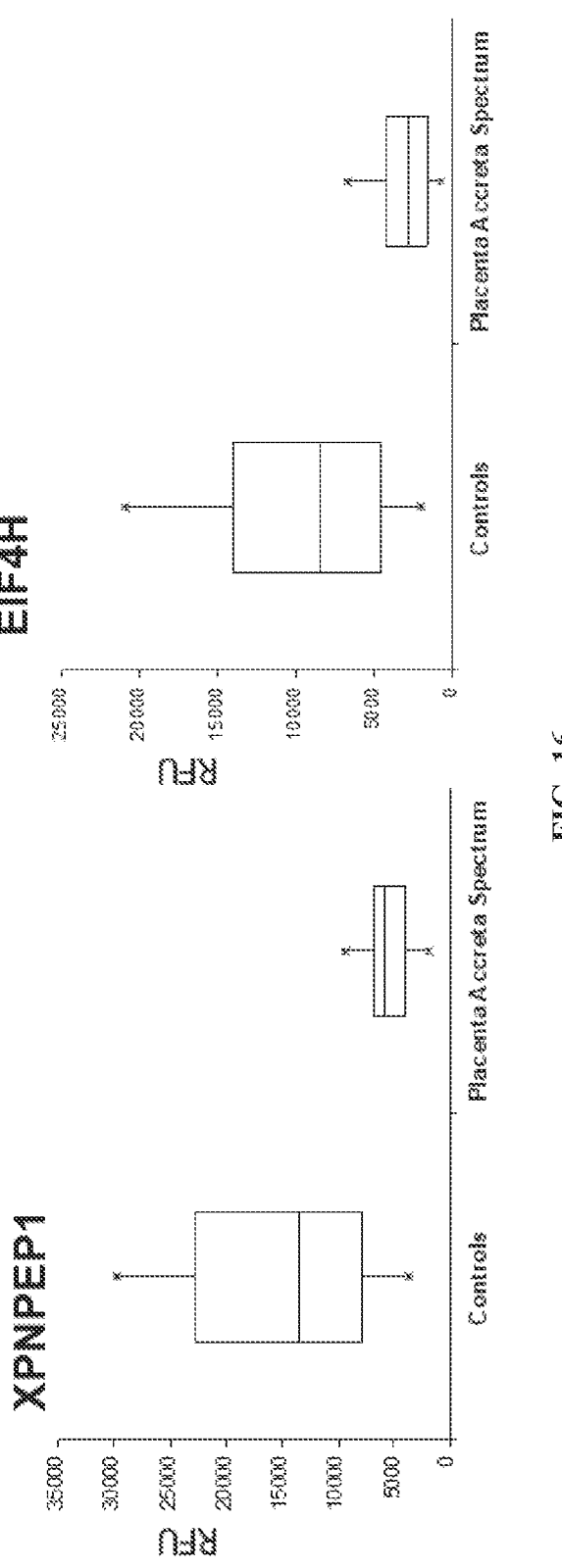
FIG. 16 comprises box whisker plots comparing the relative protein expression of XPNPEP1 and EIF4H detected in plasma samples obtained from second trimester PAS cases and controls.
Figure 17:
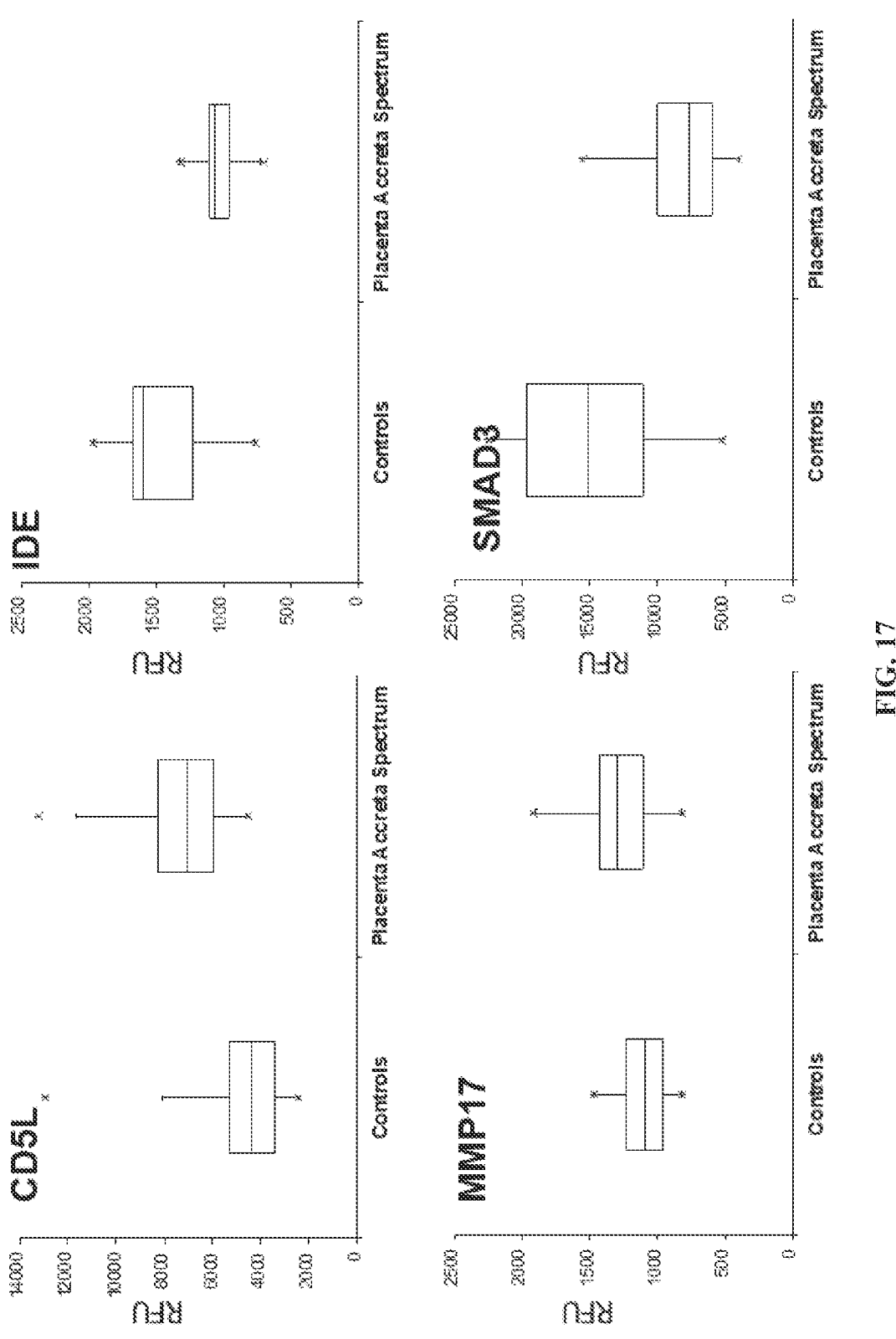
FIG. 17 comprises box whisker plots comparing the relative protein expression of CD5L, IDE, MMP17, and SMAD3 detected in plasma samples obtained from second trimester PAS cases with placenta previa and controls.

In the second trimester, subjects with PAS had higher expression levels of CD5L, FGF5, ESM1, and S100A7 and lower expression levels of XPNPEP1 and EIF4H than did healthy control subjects (FIGS. 15 and 16, respectively). Protein expression levels of CD5L, IDE, MMP17, and SMAD3 were examined in subjects in their second trimester having PAS and placenta previa and controls. Average expression levels were different between the two groups (FIG. 17).

The results reported herein above were obtained using the following materials and methods.

Participants were enrolled in ongoing, prospective cohort studies at two tertiary care medical centers from February 2017 through April 2019 and selected as PAS cases or controls. The eligibility criteria for cases were age ≥18 years, availability of a third-trimester plasma sample, and antenatal suspicion of PAS that was confirmed at delivery. The diagnosis of PAS was based on histologic confirmation and/or clinical criteria (i.e., placenta adherent to the uterine wall without easy separation from the placental bed). Of the 16 cases, 15 had histological confirmation of PAS. Controls were eligible if they were ≥18 years, had a third-trimester plasma sample, and did not have a diagnosis of PAS, preeclampsia, diabetes, or hypertension. Controls were chosen such that the gestational age at the blood draw was within the gestational age range at time of blood draw for the cases. Gestational age was based on the best obstetric estimate using the last menstrual period and ultrasound. Plasma samples were collected in the third trimester in EDTA tubes, and aliquots were stored at −70° C. until assayed.

SOMAscan® analysis (SomaLogic, Inc., Boulder, CO) using plasma samples was performed according to standard protocols for biological fluids from SomaLogic that have been described elsewhere (Gold et al., PLOS One, 5: e15004 (2010); Mehan et al., Adv. Exp. Med. Biol.735:283-300 (2013), U.S. Pat. No. 10,359,435, the contents of each are incorporated herein by reference in their entirety). Using the recommended protocol from the manufacturer, 50 µL plasma samples were run on the SOMAscan® Assay 1.3k for human plasma, which measures the expression of 1,305 human proteins using highly selective single-stranded modified Slow Off-rate Modified DNA Aptamers (SOMAmer). Five pooled human plasma controls and one no-protein buffer control were run in parallel with the plasma test samples. Sample to sample variability was further controlled by several hybridization spike-in controls. Data quality control, calibration, and normalization were done according to the manufacturer's protocol, as previously described (Ciampa et al., Hypertension, 72:219-26 (2018) and Tarca et al., PLOS One, 14: e0217273 (2019), the contents of each are incorporated herein by reference in their entirety.

Mean and median fold-changes (FC) of protein expression were calculated for proteins with statistically significant different expression between cases and controls. Statistical significance was determined by using a t-test to compare log-transformed SOMAscan® relative fluorescence units (SomaSuite V1.0, SomaLogic, Inc., Boulder, CO). A protein was considered to be significantly dysregulated if the p-value for expression between cases and controls was <0.01, as described in Ciampa et al. Differential expression analysis was also performed using the approach described in the Linear Models for Microarray data (LIMMA) package in Bioconductor to generate moderated t-test analysis for differentially expressed proteins 25 and both ordinary and moderated t-test p-values are reported. Heat maps of the most significantly dysregulated proteins (T test p<0.01) were generated with Morpheus (Broad Institute, Cambridge, MA). Principal component analysis was performed for the top 21 dysregulated proteins as well as all 1,305 proteins to evaluate their ability to discriminate cases from controls using XLSTAT (Addinsoft, Long Island City, NY).

To assess potential molecular pathways underlying the PAS-specific plasma protein signatures and to more precisely understand the complex interactions between differentially expressed proteins, functional category, canonical pathway, interactive network, upstream regulator, and regulator effect analyses were performed of all dysregulated proteins with a P value <0.01. Using the Ingenuity Pathway Analysis software tool (QIAGEN, Redwood City, CA), a repository of biological interactions and functions created from millions of individually modeled relationships ranging from the molecular (proteins, genes) to organism (diseases) level. Antithrombin III (also referred to as SERPINC1), plasminogen activator inhibitor (PAI-1 or SERPINE1), soluble TEK (Tie2), and soluble VEGF receptor 2 (also referred to as KDR, SKDR, or VEGFR2) were measured using commercial immunoassay kits (R & D systems, Minneapolis, MN), see Table 7. Inter-assay coefficients of variation for the 4 analytes were 4.3%-7.4% for Antithrombin III, 6.1%-8.7% for SERPINE1, 5.2%-8.5% for soluble TEK and 5.7%-7.0% for soluble VEGF receptor 2. Immunoassays were performed following the manufacturers' protocols, and assay personnel were blinded to case and control status.

TABLE 7

Plasma biomarker concentration among cases
of placenta accreta spectrum (PAS) cases compared
with controls in validation cohort.

| Biomarkers | PAS Cases n = 73 | Control n = 146 | P |
|---|---|---|---|
| Serpin C1/antithrombin-III, ug/ml | 163.46 ± 53.50 | 136.17 ± 44.68 | 0.003 |
| Tie-2, ng/ml | 14.37 ± 5.65 | 13.53 ± 3.39 | 0.02 |
| VEGF R2/KDR, ng/ml | 8.92 ± 2.15 | 8.10 ± 2.61 | 0.01 |

Data are presented as mean ± standard deviation

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for characterizing placenta accreta spectrum biomarkers in a biological sample, the method comprising contacting a biological sample of the subject with a panel comprising four distinct capture molecules bound to a substrate, each of which specifically binds one of the following polypeptide or polynucleotide biomarkers: anti-thrombin III, plasminogen activator inhibitor 1, soluble Tie2, and soluble VEGF receptor 2, wherein the biological sample is a maternal plasma sample.

2. A method for characterizing placenta accreta spectrum in a pregnant subject, the method comprising characterizing placenta accreta spectrum biomarkers in a biological sample of a pregnant subject using a panel comprising three distinct capture molecules bound to a substrate, each of which specifically binds one of the following biomarkers: anti-thrombin III, soluble Tie2, and soluble VEGF receptor 2;
   wherein the biological sample is a maternal plasma sample; and
   wherein the method comprises contacting the biological sample with the panel.

3. The method of claim 2, wherein the subject is in the third trimester of pregnancy.

4. The method of claim 2, further comprising determining the body mass index (BMI), obtaining imaging of the uterus of the subject, and or acquiring a clinical history of the subject.

\* \* \* \* \*

SEQUENCE LISTING

```
<160> NUMBER OF SEQ ID NOS: 34

<210> SEQ ID NO 1
<211> LENGTH: 417
<212> TYPE: PRT
<213> ORGANISM: Homo sapiens

<400> SEQUENCE: 1

Met Ser Leu Ser Asn Lys Leu Thr Leu Asp Lys Leu Asp Val Lys Gly
1               5                   10                  15

Lys Arg Val Val Met Arg Val Asp Phe Asn Val Pro Met Lys Asn Asn
            20                  25                  30

Gln Ile Thr Asn Asn Gln Arg Ile Lys Ala Ala Val Pro Ser Ile Lys
        35                  40                  45

Phe Cys Leu Asp Asn Gly Ala Lys Ser Val Val Leu Met Ser His Leu
    50                  55                  60

Gly Arg Pro Asp Gly Val Pro Met Pro Asp Lys Tyr Ser Leu Glu Pro
65                  70                  75                  80

Val Ala Val Glu Leu Lys Ser Leu Leu Gly Lys Asp Val Leu Phe Leu
                85                  90                  95

Lys Asp Cys Val Gly Pro Glu Val Glu Lys Ala Cys Ala Asn Pro Ala
            100                 105                 110

Ala Gly Ser Val Ile Leu Leu Glu Asn Leu Arg Phe His Val Glu Glu
        115                 120                 125

Glu Gly Lys Gly Lys Asp Ala Ser Gly Asn Lys Val Lys Ala Glu Pro
    130                 135                 140

Ala Lys Ile Glu Ala Phe Arg Ala Ser Leu Ser Lys Leu Gly Asp Val
145                 150                 155                 160

Tyr Val Asn Asp Ala Phe Gly Thr Ala His Arg Ala His Ser Ser Met
                165                 170                 175

Val Gly Val Asn Leu Pro Gln Lys Ala Gly Gly Phe Leu Met Lys Lys
                180                 185                 190

Glu Leu Asn Tyr Phe Ala Lys Ala Leu Glu Ser Pro Glu Arg Pro Phe
            195                 200                 205

Leu Ala Ile Leu Gly Gly Ala Lys Val Ala Asp Lys Ile Gln Leu Ile
        210                 215                 220

Asn Asn Met Leu Asp Lys Val Asn Glu Met Ile Ile Gly Gly Gly Met
225                 230                 235                 240

Ala Phe Thr Phe Leu Lys Val Leu Asn Asn Met Glu Ile Gly Thr Ser
                245                 250                 255
```

```
Leu Phe Asp Glu Glu Gly Ala Lys Ile Val Lys Asp Leu Met Ser Lys
        260                 265                 270

Ala Glu Lys Asn Gly Val Lys Ile Thr Leu Pro Val Asp Phe Val Thr
        275                 280                 285

Ala Asp Lys Phe Asp Glu Asn Ala Lys Thr Gly Gln Ala Thr Val Ala
    290                 295                 300

Ser Gly Ile Pro Ala Gly Trp Met Gly Leu Asp Cys Gly Pro Glu Ser
305                 310                 315                 320

Ser Lys Lys Tyr Ala Glu Ala Val Thr Arg Ala Lys Gln Ile Val Trp
                325                 330                 335

Asn Gly Pro Val Gly Val Phe Glu Trp Glu Ala Phe Ala Arg Gly Thr
                340                 345                 350

Lys Ala Leu Met Asp Glu Val Val Lys Ala Thr Ser Arg Gly Cys Ile
        355                 360                 365

Thr Ile Ile Gly Gly Gly Asp Thr Ala Thr Cys Cys Ala Lys Trp Asn
    370                 375                 380

Thr Glu Asp Lys Val Ser His Val Ser Thr Gly Gly Gly Ala Ser Leu
385                 390                 395                 400

Glu Leu Leu Glu Gly Lys Val Leu Pro Gly Val Asp Ala Leu Ser Asn
                405                 410                 415

Ile

<210> SEQ ID NO 2
<211> LENGTH: 214
<212> TYPE: PRT
<213> ORGANISM: Homo sapiens

<400> SEQUENCE: 2

Met Ala Gly Glu Asn Phe Ala Thr Pro Phe His Gly His Val Gly Arg
1               5                   10                  15

Gly Ala Phe Ser Asp Val Tyr Glu Pro Ala Glu Asp Thr Phe Leu Leu
            20                  25                  30

Leu Asp Ala Leu Glu Ala Ala Ala Ala Glu Leu Ala Gly Val Glu Ile
        35                  40                  45

Cys Leu Glu Val Gly Ser Gly Ser Gly Val Val Ser Ala Phe Leu Ala
    50                  55                  60

Ser Met Ile Gly Pro Gln Ala Leu Tyr Met Cys Thr Asp Ile Asn Pro
65                  70                  75                  80

Glu Ala Ala Ala Cys Thr Leu Glu Thr Ala Arg Cys Asn Lys Val His
                85                  90                  95

Ile Gln Pro Val Ile Thr Asp Leu Val Lys Gly Leu Leu Pro Arg Leu
                100                 105                 110

Thr Glu Lys Val Asp Leu Leu Val Phe Asn Pro Pro Tyr Val Val Thr
            115                 120                 125

Pro Pro Gln Glu Val Gly Ser His Gly Ile Glu Ala Ala Trp Ala Gly
        130                 135                 140

Gly Arg Asn Gly Arg Glu Val Met Asp Arg Phe Phe Pro Leu Val Pro
145                 150                 155                 160

Asp Leu Leu Ser Pro Arg Gly Leu Phe Tyr Leu Val Thr Ile Lys Glu
                165                 170                 175

Asn Asn Pro Glu Glu Ile Leu Lys Ile Met Lys Thr Lys Gly Leu Gln
                180                 185                 190

Gly Thr Thr Ala Leu Ser Arg Gln Ala Gly Gln Glu Thr Leu Ser Val
            195                 200                 205
```

```
Leu Lys Phe Thr Lys Ser
    210

<210> SEQ ID NO 3
<211> LENGTH: 282
<212> TYPE: PRT
<213> ORGANISM: Homo sapiens

<400> SEQUENCE: 3

Met Ala Leu Lys Gln Ile Ser Ser Asn Lys Cys Phe Gly Gly Leu Gln
1               5                   10                  15

Lys Val Phe Glu His Asp Ser Val Glu Leu Asn Cys Lys Met Lys Phe
                20                  25                  30

Ala Val Tyr Leu Pro Pro Lys Ala Glu Thr Gly Lys Cys Pro Ala Leu
            35                  40                  45

Tyr Trp Leu Ser Gly Leu Thr Cys Thr Glu Gln Asn Phe Ile Ser Lys
        50                  55                  60

Ser Gly Tyr His Gln Ser Ala Ser Glu His Gly Leu Val Val Ile Ala
65                  70                  75                  80

Pro Asp Thr Ser Pro Arg Gly Cys Asn Ile Lys Gly Glu Asp Glu Ser
                85                  90                  95

Trp Asp Phe Gly Thr Gly Ala Gly Phe Tyr Val Asp Ala Thr Glu Asp
                100                 105                 110

Pro Trp Lys Thr Asn Tyr Arg Met Tyr Ser Tyr Val Thr Glu Glu Leu
                115                 120                 125

Pro Gln Leu Ile Asn Ala Asn Phe Pro Val Asp Pro Gln Arg Met Ser
        130                 135                 140

Ile Phe Gly His Ser Met Gly Gly His Gly Ala Leu Ile Cys Ala Leu
145                 150                 155                 160

Lys Asn Pro Gly Lys Tyr Lys Ser Val Ser Ala Phe Ala Pro Ile Cys
                165                 170                 175

Asn Pro Val Leu Cys Pro Trp Gly Lys Lys Ala Phe Ser Gly Tyr Leu
                180                 185                 190

Gly Thr Asp Gln Ser Lys Trp Lys Ala Tyr Asp Ala Thr His Leu Val
                195                 200                 205

Lys Ser Tyr Pro Gly Ser Gln Leu Asp Ile Leu Ile Asp Gln Gly Lys
        210                 215                 220

Asp Asp Gln Phe Leu Leu Asp Gly Gln Leu Leu Pro Asp Asn Phe Ile
225                 230                 235                 240

Ala Ala Cys Thr Glu Lys Lys Ile Pro Val Val Phe Arg Leu Gln Glu
                245                 250                 255

Gly Tyr Asp His Ser Tyr Tyr Phe Ile Ala Thr Phe Ile Thr Asp His
            260                 265                 270

Ile Arg His His Ala Lys Tyr Leu Asn Ala
        275                 280

<210> SEQ ID NO 4
<211> LENGTH: 200
<212> TYPE: PRT
<213> ORGANISM: Homo sapiens

<400> SEQUENCE: 4

Met Gly Arg Leu His Cys Thr Glu Asp Pro Val Pro Glu Ala Val Gly
1               5                   10                  15

Gly Asp Met Gln Gln Leu Asn Gln Leu Gly Ala Gln Gln Phe Ser Ala
                20                  25                  30
```

-continued

```
Leu Thr Glu Val Leu Phe His Phe Leu Thr Glu Pro Lys Glu Val Glu
        35                  40                  45

Arg Phe Leu Ala Gln Leu Ser Glu Phe Ala Thr Thr Asn Gln Ile Ser
    50                  55                  60

Leu Gly Ser Leu Arg Ser Ile Val Lys Ser Leu Leu Leu Val Pro Asn
65                  70                  75                  80

Gly Ala Leu Lys Lys Ser Leu Thr Ala Lys Gln Val Gln Ala Asp Phe
                85                  90                  95

Ile Thr Leu Gly Leu Ser Glu Glu Lys Ala Thr Tyr Phe Ser Glu Lys
            100                 105                 110

Trp Lys Gln Asn Ala Pro Thr Leu Ala Arg Trp Ala Ile Gly Gln Thr
            115                 120                 125

Leu Met Ile Asn Gln Leu Ile Asp Met Glu Trp Lys Phe Gly Val Thr
        130                 135                 140

Ser Gly Ser Ser Glu Leu Glu Lys Val Gly Ser Ile Phe Leu Gln Leu
145                 150                 155                 160

Lys Leu Val Val Lys Lys Gly Asn Gln Thr Glu Asn Val Tyr Ile Glu
                165                 170                 175

Leu Thr Leu Pro Gln Phe Tyr Ser Phe Leu His Glu Met Glu Arg Val
            180                 185                 190

Arg Thr Ser Met Glu Cys Phe Cys
        195                 200
```

```
<210> SEQ ID NO 5
<211> LENGTH: 210
<212> TYPE: PRT
<213> ORGANISM: Homo sapiens

<400> SEQUENCE: 5
```

```
Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
            115                 120                 125

Pro Phe Glu Thr Leu Leu Ser Gln Asn Gln Gly Gly Lys Thr Phe Ile
        130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190

Phe Leu Ala Ser Pro Glu Tyr Val Asn Leu Pro Ile Asn Gly Asn Gly
```

-continued

```
               195                 200                 205

Lys Gln
    210

<210> SEQ ID NO 6
<211> LENGTH: 1019
<212> TYPE: PRT
<213> ORGANISM: Homo sapiens

<400> SEQUENCE: 6

Met Arg Tyr Arg Leu Ala Trp Leu Leu His Pro Ala Leu Pro Ser Thr
1               5                   10                  15

Phe Arg Ser Val Leu Gly Ala Arg Leu Pro Pro Glu Arg Leu Cys
            20                  25                  30

Gly Phe Gln Lys Lys Thr Tyr Ser Lys Met Asn Asn Pro Ala Ile Lys
        35                  40                  45

Arg Ile Gly Asn His Ile Thr Lys Ser Pro Glu Asp Lys Arg Glu Tyr
    50                  55                  60

Arg Gly Leu Glu Leu Ala Asn Gly Ile Lys Val Leu Leu Ile Ser Asp
65                  70                  75                  80

Pro Thr Thr Asp Lys Ser Ser Ala Ala Leu Asp Val His Ile Gly Ser
                85                  90                  95

Leu Ser Asp Pro Pro Asn Ile Ala Gly Leu Ser His Phe Cys Glu His
            100                 105                 110

Met Leu Phe Leu Gly Thr Lys Lys Tyr Pro Lys Glu Asn Glu Tyr Ser
        115                 120                 125

Gln Phe Leu Ser Glu His Ala Gly Ser Ser Asn Ala Phe Thr Ser Gly
    130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Glu
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
        195                 200                 205

Gly Asn Pro Lys His Pro Phe Ser Lys Phe Gly Thr Gly Asn Lys Tyr
    210                 215                 220

Thr Leu Glu Thr Arg Pro Asn Gln Glu Gly Ile Asp Val Arg Gln Glu
225                 230                 235                 240

Leu Leu Lys Phe His Ser Ala Tyr Tyr Ser Ser Asn Leu Met Ala Val
                245                 250                 255

Cys Val Leu Gly Arg Glu Ser Leu Asp Asp Leu Thr Asn Leu Val Val
            260                 265                 270

Lys Leu Phe Ser Glu Val Glu Asn Lys Asn Val Pro Leu Pro Glu Phe
        275                 280                 285

Pro Glu His Pro Phe Gln Glu Glu His Leu Lys Gln Leu Tyr Lys Ile
    290                 295                 300

Val Pro Ile Lys Asp Ile Arg Asn Leu Tyr Val Thr Phe Pro Ile Pro
305                 310                 315                 320

Asp Leu Gln Lys Tyr Tyr Lys Ser Asn Pro Gly His Tyr Leu Gly His
                325                 330                 335

Leu Ile Gly His Glu Gly Pro Gly Ser Leu Leu Ser Glu Leu Lys Ser
            340                 345                 350
```

Lys Gly Trp Val Asn Thr Leu Val Gly Gly Gln Lys Glu Gly Ala Arg
         355                 360                 365

Gly Phe Met Phe Phe Ile Ile Asn Val Asp Leu Thr Glu Glu Gly Leu
         370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
                 405                 410                 415

Leu Asn Ala Val Ala Phe Arg Phe Lys Asp Lys Glu Arg Pro Arg Gly
                 420                 425                 430

Tyr Thr Ser Lys Ile Ala Gly Ile Leu His Tyr Tyr Pro Leu Glu Glu
         435                 440                 445

Val Leu Thr Ala Glu Tyr Leu Leu Glu Glu Phe Arg Pro Asp Leu Ile
         450                 455                 460

Glu Met Val Leu Asp Lys Leu Arg Pro Glu Asn Val Arg Val Ala Ile
465                 470                 475                 480

Val Ser Lys Ser Phe Glu Gly Lys Thr Asp Arg Thr Glu Glu Trp Tyr
                 485                 490                 495

Gly Thr Gln Tyr Lys Gln Glu Ala Ile Pro Asp Glu Val Ile Lys Lys
                 500                 505                 510

Trp Gln Asn Ala Asp Leu Asn Gly Lys Phe Lys Leu Pro Thr Lys Asn
         515                 520                 525

Glu Phe Ile Pro Thr Asn Phe Glu Ile Leu Pro Leu Glu Lys Glu Ala
         530                 535                 540

Thr Pro Tyr Pro Ala Leu Ile Lys Asp Thr Ala Met Ser Lys Leu Trp
545                 550                 555                 560

Phe Lys Gln Asp Asp Lys Phe Phe Leu Pro Lys Ala Cys Leu Asn Phe
                 565                 570                 575

Glu Phe Phe Ser Pro Phe Ala Tyr Val Asp Pro Leu His Cys Asn Met
                 580                 585                 590

Ala Tyr Leu Tyr Leu Glu Leu Leu Lys Asp Ser Leu Asn Glu Tyr Ala
         595                 600                 605

Tyr Ala Ala Glu Leu Ala Gly Leu Ser Tyr Asp Leu Gln Asn Thr Ile
         610                 615                 620

Tyr Gly Met Tyr Leu Ser Val Lys Gly Tyr Asn Asp Lys Gln Pro Ile
625                 630                 635                 640

Leu Leu Lys Lys Ile Ile Glu Lys Met Ala Thr Phe Glu Ile Asp Glu
                 645                 650                 655

Lys Arg Phe Glu Ile Ile Lys Glu Ala Tyr Met Arg Ser Leu Asn Asn
                 660                 665                 670

Phe Arg Ala Glu Gln Pro His Gln His Ala Met Tyr Tyr Leu Arg Leu
         675                 680                 685

Leu Met Thr Glu Val Ala Trp Thr Lys Asp Glu Leu Lys Glu Ala Leu
         690                 695                 700

Asp Asp Val Thr Leu Pro Arg Leu Lys Ala Phe Ile Pro Gln Leu Leu
705                 710                 715                 720

Ser Arg Leu His Ile Glu Ala Leu Leu His Gly Asn Ile Thr Lys Gln
                 725                 730                 735

Ala Ala Leu Gly Ile Met Gln Met Val Glu Asp Thr Leu Ile Glu His
         740                 745                 750

Ala His Thr Lys Pro Leu Leu Pro Ser Gln Leu Val Arg Tyr Arg Glu
         755                 760                 765

Val Gln Leu Pro Asp Arg Gly Trp Phe Val Tyr Gln Gln Arg Asn Glu

```
               770               775               780

Val His Asn Asn Cys Gly Ile Glu Ile Tyr Tyr Gln Thr Asp Met Gln
785               790               795               800

Ser Thr Ser Glu Asn Met Phe Leu Glu Leu Phe Cys Gln Ile Ile Ser
                   805               810               815

Glu Pro Cys Phe Asn Thr Leu Arg Thr Lys Glu Gln Leu Gly Tyr Ile
                   820               825               830

Val Phe Ser Gly Pro Arg Arg Ala Asn Gly Ile Gln Gly Leu Arg Phe
                   835               840               845

Ile Ile Gln Ser Glu Lys Pro Pro His Tyr Leu Glu Ser Arg Val Glu
                   850               855               860

Ala Phe Leu Ile Thr Met Glu Lys Ser Ile Glu Asp Met Thr Glu Glu
865               870               875               880

Ala Phe Gln Lys His Ile Gln Ala Leu Ala Ile Arg Arg Leu Asp Lys
                   885               890               895

Pro Lys Lys Leu Ser Ala Glu Cys Ala Lys Tyr Trp Gly Glu Ile Ile
                   900               905               910

Ser Gln Gln Tyr Asn Phe Asp Arg Asp Asn Thr Glu Val Ala Tyr Leu
                   915               920               925

Lys Thr Leu Thr Lys Glu Asp Ile Ile Lys Phe Tyr Lys Glu Met Leu
                   930               935               940

Ala Val Asp Ala Pro Arg Arg His Lys Val Ser Val His Val Leu Ala
945               950               955               960

Arg Glu Met Asp Ser Cys Pro Val Val Gly Glu Phe Pro Cys Gln Asn
                   965               970               975

Asp Ile Asn Leu Ser Gln Ala Pro Ala Leu Pro Gln Pro Glu Val Ile
                   980               985               990

Gln Asn Met Thr Glu Phe Lys Arg  Gly Leu Pro Leu Phe  Pro Leu Val
                   995               1000               1005

Lys Pro  His Ile Asn Phe Met  Ala Ala Lys Leu
     1010               1015
```

<210> SEQ ID NO 7
<211> LENGTH: 430
<212> TYPE: PRT
<213> ORGANISM: Homo sapiens

<400> SEQUENCE: 7

```
Met Ala Ala Asn Leu Ser Arg Asn Gly Pro Ala Leu Gln Glu Ala Tyr
1               5               10               15

Val Arg Val Val Thr Glu Lys Ser Pro Thr Asp Trp Ala Leu Phe Thr
                   20               25               30

Tyr Glu Gly Asn Ser Asn Asp Ile Arg Val Ala Gly Thr Gly Glu Gly
                   35               40               45

Gly Leu Glu Glu Met Val Glu Glu Leu Asn Ser Gly Lys Val Met Tyr
                   50               55               60

Ala Phe Cys Arg Val Lys Asp Pro Asn Ser Gly Leu Pro Lys Phe Val
65               70               75               80

Leu Ile Asn Trp Thr Gly Glu Gly Val Asn Asp Val Arg Lys Gly Ala
                   85               90               95

Cys Ala Ser His Val Ser Thr Met Ala Ser Phe Leu Lys Gly Ala His
                   100               105               110

Val Thr Ile Asn Ala Arg Ala Glu Glu Asp Val Glu Pro Glu Cys Ile
                   115               120               125
```

-continued

```
Met Glu Lys Val Ala Lys Ala Ser Gly Ala Asn Tyr Ser Phe His Lys
    130             135                 140

Glu Ser Gly Arg Phe Gln Asp Val Gly Pro Gln Ala Pro Val Gly Ser
145             150                 155                 160

Val Tyr Gln Lys Thr Asn Ala Val Ser Glu Ile Lys Arg Val Gly Lys
                165                 170                 175

Asp Ser Phe Trp Ala Lys Ala Glu Lys Glu Glu Glu Asn Arg Arg Leu
            180                 185                 190

Glu Glu Lys Arg Arg Ala Glu Glu Ala Gln Arg Gln Leu Glu Gln Glu
            195                 200                 205

Arg Arg Glu Arg Glu Leu Arg Glu Ala Ala Arg Arg Glu Gln Arg Tyr
    210                 215                 220

Gln Glu Gln Gly Gly Glu Ala Ser Pro Gln Arg Thr Trp Glu Gln Gln
225                 230                 235                 240

Gln Glu Val Val Ser Arg Asn Arg Asn Glu Gln Glu Ser Ala Val His
                245                 250                 255

Pro Arg Glu Ile Phe Lys Gln Lys Glu Arg Ala Met Ser Thr Thr Ser
            260                 265                 270

Ile Ser Ser Pro Gln Pro Gly Lys Leu Arg Ser Pro Phe Leu Gln Lys
            275                 280                 285

Gln Leu Thr Gln Pro Glu Thr His Phe Gly Arg Glu Pro Ala Ala Ala
    290                 295                 300

Ile Ser Arg Pro Arg Ala Asp Leu Pro Ala Glu Glu Pro Ala Pro Ser
305                 310                 315                 320

Thr Pro Pro Cys Leu Val Gln Ala Glu Glu Glu Ala Val Tyr Glu Glu
                325                 330                 335

Pro Pro Glu Gln Glu Thr Phe Tyr Glu Gln Pro Pro Leu Val Gln Gln
            340                 345                 350

Gln Gly Ala Gly Ser Glu His Ile Asp His His Ile Gln Gly Gln Gly
            355                 360                 365

Leu Ser Gly Gln Gly Leu Cys Ala Arg Ala Leu Tyr Asp Tyr Gln Ala
    370                 375                 380

Ala Asp Asp Thr Glu Ile Ser Phe Asp Pro Glu Asn Leu Ile Thr Gly
385                 390                 395                 400

Ile Glu Val Ile Asp Glu Gly Trp Trp Arg Gly Tyr Gly Pro Asp Gly
                405                 410                 415

His Phe Gly Met Phe Pro Ala Asn Tyr Val Glu Leu Ile Glu
            420                 425                 430

<210> SEQ ID NO 8
<211> LENGTH: 162
<212> TYPE: PRT
<213> ORGANISM: Homo sapiens

<400> SEQUENCE: 8

Met Lys Gly Phe Thr Ala Thr Leu Phe Leu Trp Thr Leu Ile Phe Pro
1               5                   10                  15

Ser Cys Ser Gly Gly Gly Gly Lys Ala Trp Pro Thr His Val Val
                20                  25                  30

Cys Ser Asp Ser Gly Leu Glu Val Leu Tyr Gln Ser Cys Asp Pro Leu
            35                  40                  45

Gln Asp Phe Gly Phe Ser Val Glu Lys Cys Ser Lys Gln Leu Lys Ser
    50                  55                  60

Asn Ile Asn Ile Arg Phe Gly Ile Ile Leu Arg Glu Asp Ile Lys Glu
65                  70                  75                  80
```

-continued

```
Leu Phe Leu Asp Leu Ala Leu Met Ser Gln Gly Ser Ser Val Leu Asn
                85                  90                  95

Phe Ser Tyr Pro Ile Cys Glu Ala Ala Leu Pro Lys Phe Ser Phe Cys
                100                 105                 110

Gly Arg Arg Lys Gly Glu Gln Ile Tyr Tyr Ala Gly Pro Val Asn Asn
                115                 120                 125

Pro Glu Phe Thr Ile Pro Gln Gly Glu Tyr Gln Val Leu Leu Glu Leu
        130                 135                 140

Tyr Thr Glu Lys Arg Ser Thr Val Ala Cys Ala Asn Ala Thr Ile Met
145                 150                 155                 160

Cys Ser

<210> SEQ ID NO 9
<211> LENGTH: 479
<212> TYPE: PRT
<213> ORGANISM: Homo sapiens

<400> SEQUENCE: 9

Met Ala Thr Asp Ser Trp Ala Leu Ala Val Asp Glu Gln Glu Ala Ala
1               5                   10                  15

Ala Glu Ser Leu Ser Asn Leu His Leu Lys Glu Glu Lys Ile Lys Pro
                20                  25                  30

Asp Thr Asn Gly Ala Val Val Lys Thr Asn Ala Asn Ala Glu Lys Thr
            35                  40                  45

Asp Glu Glu Glu Lys Glu Asp Arg Ala Ala Gln Ser Leu Leu Asn Lys
        50                  55                  60

Leu Ile Arg Ser Asn Leu Val Asp Asn Thr Asn Gln Val Glu Val Leu
65                  70                  75                  80

Gln Arg Asp Pro Asn Ser Pro Leu Tyr Ser Val Lys Ser Phe Glu Glu
                85                  90                  95

Leu Arg Leu Lys Pro Gln Leu Leu Gln Gly Val Tyr Ala Met Gly Phe
                100                 105                 110

Asn Arg Pro Ser Lys Ile Gln Glu Asn Ala Leu Pro Leu Met Leu Val
                115                 120                 125

Glu Pro Pro Gln Asn Leu Ile Ala Gln Ser Gln Ser Gly Thr Gly Lys
        130                 135                 140

Thr Ala Ala Phe Val Leu Ala Met Leu Ser Gln Val Glu Pro Ala Asn
145                 150                 155                 160

Lys Tyr Pro Gln Cys Leu Cys Leu Ser Pro Thr Tyr Glu Leu Ala Leu
                165                 170                 175

Gln Thr Gly Lys Val Ile Glu Gln Met Gly Lys Phe Tyr Pro Glu Leu
                180                 185                 190

Lys Leu Ala Tyr Ala Val Arg Gly Asn Lys Leu Glu Arg Gly Gln Lys
                195                 200                 205

Ile Ser Glu Gln Ile Val Ile Gly Thr Pro Gly Thr Val Leu Asp Trp
        210                 215                 220

Cys Ser Lys Leu Lys Phe Ile Asp Pro Lys Lys Ile Lys Val Phe Val
225                 230                 235                 240

Leu Asp Glu Ala Asp Val Met Ile Ala Thr Gln Gly His Gln Asp Gln
                245                 250                 255

Ser Ile Arg Ile Gln Arg Met Leu Pro Arg Asn Cys Gln Met Leu Leu
                260                 265                 270

Phe Ser Ala Thr Phe Glu Asp Ser Val Trp Lys Phe Ala Gln Lys Val
                275                 280                 285
```

```
Val Pro Asp Pro Asn Val Ile Lys Leu Lys Arg Glu Glu Glu Thr Leu
    290             295             300

Asp Thr Ile Lys Gln Tyr Tyr Val Leu Cys Ser Ser Arg Asp Glu Lys
305             310             315             320

Phe Gln Ala Leu Cys Asn Leu Tyr Gly Ala Thr Thr Ile Ala Gln Ala
                325             330             335

Met Ile Phe Cys His Thr Arg Lys Thr Ala Ser Trp Leu Ala Ala Glu
            340             345             350

Leu Ser Lys Glu Gly His Gln Val Ala Leu Leu Ser Gly Glu Met Met
        355             360             365

Val Glu Gln Arg Ala Ala Val Ile Glu Arg Phe Arg Glu Gly Lys Glu
    370             375             380

Lys Val Leu Val Thr Thr Asn Val Cys Ala Arg Gly Ile Asp Val Glu
385             390             395             400

Gln Val Ser Val Val Ile Asn Phe Asp Leu Pro Val Asp Lys Asp Gly
                405             410             415

Asn Pro Asp Asn Glu Thr Tyr Leu His Arg Ile Gly Arg Thr Gly Arg
            420             425             430

Phe Gly Lys Arg Gly Leu Ala Val Asn Met Val Asp Ser Lys His Ser
        435             440             445

Met Asn Ile Leu Asn Arg Ile Gln Glu His Phe Asn Lys Lys Ile Glu
    450             455             460

Arg Leu Asp Thr Asp Asp Leu Asp Glu Ile Glu Lys Ile Ala Asn
465             470             475
```

```
<210> SEQ ID NO 10
<211> LENGTH: 629
<212> TYPE: PRT
<213> ORGANISM: Homo sapiens

<400> SEQUENCE: 10
```

```
Met Asn Gln Val Thr Ile Gln Trp Asp Ala Val Ile Ala Leu Tyr Ile
1               5               10              15

Leu Phe Ser Trp Cys His Gly Gly Ile Thr Asn Ile Asn Cys Ser Gly
            20              25              30

His Ile Trp Val Glu Pro Ala Thr Ile Phe Lys Met Gly Met Asn Ile
        35              40              45

Ser Ile Tyr Cys Gln Ala Ala Ile Lys Asn Cys Gln Pro Arg Lys Leu
    50              55              60

His Phe Tyr Lys Asn Gly Ile Lys Glu Arg Phe Gln Ile Thr Arg Ile
65              70              75              80

Asn Lys Thr Thr Ala Arg Leu Trp Tyr Lys Asn Phe Leu Glu Pro His
            85              90              95

Ala Ser Met Tyr Cys Thr Ala Glu Cys Pro Lys His Phe Gln Glu Thr
            100             105             110

Leu Ile Cys Gly Lys Asp Ile Ser Ser Gly Tyr Pro Pro Asp Ile Pro
        115             120             125

Asp Glu Val Thr Cys Val Ile Tyr Glu Tyr Ser Gly Asn Met Thr Cys
    130             135             140

Thr Trp Asn Ala Gly Lys Leu Thr Tyr Ile Asp Thr Lys Tyr Val Val
145             150             155             160

His Val Lys Ser Leu Glu Thr Glu Glu Glu Gln Gln Tyr Leu Thr Ser
            165             170             175

Ser Tyr Ile Asn Ile Ser Thr Asp Ser Leu Gln Gly Gly Lys Lys Tyr
```

-continued

```
                     180               185               190

Leu Val Trp Val Gln Ala Ala Asn Ala Leu Gly Met Glu Glu Ser Lys
        195               200               205

Gln Leu Gln Ile His Leu Asp Asp Ile Val Ile Pro Ser Ala Ala Val
    210               215               220

Ile Ser Arg Ala Glu Thr Ile Asn Ala Thr Val Pro Lys Thr Ile Ile
225               230               235               240

Tyr Trp Asp Ser Gln Thr Thr Ile Glu Lys Val Ser Cys Glu Met Arg
            245               250               255

Tyr Lys Ala Thr Thr Asn Gln Thr Trp Asn Val Lys Glu Phe Asp Thr
        260               265               270

Asn Phe Thr Tyr Val Gln Gln Ser Glu Phe Tyr Leu Glu Pro Asn Ile
        275               280               285

Lys Tyr Val Phe Gln Val Arg Cys Gln Glu Thr Gly Lys Arg Tyr Trp
    290               295               300

Gln Pro Trp Ser Ser Leu Phe Phe His Lys Thr Pro Glu Thr Val Pro
305               310               315               320

Gln Val Thr Ser Lys Ala Phe Gln His Asp Thr Trp Asn Ser Gly Leu
            325               330               335

Thr Val Ala Ser Ile Ser Thr Gly His Leu Thr Ser Asp Asn Arg Gly
            340               345               350

Asp Ile Gly Leu Leu Leu Gly Met Ile Val Phe Ala Val Met Leu Ser
        355               360               365

Ile Leu Ser Leu Ile Gly Ile Phe Asn Arg Ser Phe Arg Thr Gly Ile
    370               375               380

Lys Arg Arg Ile Leu Leu Leu Ile Pro Lys Trp Leu Tyr Glu Asp Ile
385               390               395               400

Pro Asn Met Lys Asn Ser Asn Val Val Lys Met Leu Gln Glu Asn Ser
            405               410               415

Glu Leu Met Asn Asn Asn Ser Ser Glu Gln Val Leu Tyr Val Asp Pro
        420               425               430

Met Ile Thr Glu Ile Lys Glu Ile Phe Ile Pro Glu His Lys Pro Thr
        435               440               445

Asp Tyr Lys Lys Glu Asn Thr Gly Pro Leu Glu Thr Arg Asp Tyr Pro
    450               455               460

Gln Asn Ser Leu Phe Asp Asn Thr Thr Val Val Tyr Ile Pro Asp Leu
465               470               475               480

Asn Thr Gly Tyr Lys Pro Gln Ile Ser Asn Phe Leu Pro Glu Gly Ser
            485               490               495

His Leu Ser Asn Asn Asn Glu Ile Thr Ser Leu Thr Leu Lys Pro Pro
        500               505               510

Val Asp Ser Leu Asp Ser Gly Asn Asn Pro Arg Leu Gln Lys His Pro
        515               520               525

Asn Phe Ala Phe Ser Val Ser Ser Val Asn Ser Leu Ser Asn Thr Ile
        530               535               540

Phe Leu Gly Glu Leu Ser Leu Ile Leu Asn Gln Gly Glu Cys Ser Ser
545               550               555               560

Pro Asp Ile Gln Asn Ser Val Glu Glu Glu Thr Thr Met Leu Leu Glu
            565               570               575

Asn Asp Ser Pro Ser Glu Thr Ile Pro Glu Gln Thr Leu Leu Pro Asp
            580               585               590

Glu Phe Val Ser Cys Leu Gly Ile Val Asn Glu Glu Leu Pro Ser Ile
        595               600               605
```

-continued

```
Asn Thr Tyr Phe Pro Gln Asn Ile Leu Glu Ser His Phe Asn Arg Ile
    610             615             620

Ser Leu Leu Glu Lys
625

<210> SEQ ID NO 11
<211> LENGTH: 537
<212> TYPE: PRT
<213> ORGANISM: Homo sapiens

<400> SEQUENCE: 11

Met Ala His Cys Val Thr Leu Val Gln Leu Ser Ile Ser Cys Asp His
1               5                   10                  15

Leu Ile Asp Lys Asp Ile Gly Ser Lys Ser Asp Pro Leu Cys Val Leu
            20                  25                  30

Leu Gln Asp Val Gly Gly Gly Ser Trp Ala Glu Leu Gly Arg Thr Glu
        35                  40                  45

Arg Val Arg Asn Cys Ser Ser Pro Glu Phe Ser Lys Thr Leu Gln Leu
    50                  55                  60

Glu Tyr Arg Phe Glu Thr Val Gln Lys Leu Arg Phe Gly Ile Tyr Asp
65                  70                  75                  80

Ile Asp Asn Lys Thr Pro Glu Leu Arg Asp Asp Asp Phe Leu Gly Gly
                85                  90                  95

Ala Glu Cys Ser Leu Gly Gln Ile Val Ser Ser Gln Val Leu Thr Leu
            100                 105                 110

Pro Leu Met Leu Lys Pro Gly Lys Pro Ala Gly Arg Gly Thr Ile Thr
            115                 120                 125

Val Ser Ala Gln Glu Leu Lys Asp Asn Arg Val Val Thr Met Glu Val
    130                 135                 140

Glu Ala Arg Asn Leu Asp Lys Lys Asp Phe Leu Gly Lys Ser Asp Pro
145                 150                 155                 160

Phe Leu Glu Phe Phe Arg Gln Gly Asp Gly Lys Trp His Leu Val Tyr
                165                 170                 175

Arg Ser Glu Val Ile Lys Asn Asn Leu Asn Pro Thr Trp Lys Arg Phe
            180                 185                 190

Ser Val Pro Val Gln His Phe Cys Gly Gly Asn Pro Ser Thr Pro Ile
            195                 200                 205

Gln Val Gln Cys Ser Asp Tyr Asp Ser Asp Gly Ser His Asp Leu Ile
    210                 215                 220

Gly Thr Phe His Thr Ser Leu Ala Gln Leu Gln Ala Val Pro Ala Glu
225                 230                 235                 240

Phe Glu Cys Ile His Pro Glu Lys Gln Gln Lys Lys Lys Ser Tyr Lys
                245                 250                 255

Asn Ser Gly Thr Ile Arg Val Lys Ile Cys Arg Val Glu Thr Glu Tyr
            260                 265                 270

Ser Phe Leu Asp Tyr Val Met Gly Gly Cys Gln Ile Asn Phe Thr Val
            275                 280                 285

Gly Val Asp Phe Thr Gly Ser Asn Gly Asp Pro Ser Ser Pro Asp Ser
    290                 295                 300

Leu His Tyr Leu Ser Pro Thr Gly Val Asn Glu Tyr Leu Met Ala Leu
305                 310                 315                 320

Trp Ser Val Gly Ser Val Val Gln Asp Tyr Asp Ser Asp Lys Leu Phe
                325                 330                 335

Pro Ala Phe Gly Phe Gly Ala Gln Val Pro Pro Asp Trp Gln Val Ser
```

-continued

```
                340              345                350
His Glu Phe Ala Leu Asn Phe Asn Pro Ser Asn Pro Tyr Cys Val Gly
        355             360               365

Ile Gln Gly Ile Val Asp Ala Tyr Arg Gln Ala Leu Pro Gln Val Arg
        370             375           380

Leu Tyr Gly Pro Thr Asn Phe Ala Pro Ile Ile Asn His Val Ala Arg
385                 390               395                 400

Phe Ala Ala Gln Ala Ala His Gln Gly Thr Ala Ser Gln Tyr Phe Met
                405             410               415

Leu Leu Leu Leu Thr Asp Gly Ala Val Thr Asp Val Glu Ala Thr Arg
            420             425               430

Glu Ala Val Val Arg Ala Ser Asn Leu Pro Met Ser Val Ile Ile Val
        435             440               445

Gly Val Gly Gly Ala Asp Phe Glu Ala Met Glu Gln Leu Asp Ala Asp
        450             455               460

Gly Gly Pro Leu His Thr Arg Ser Gly Gln Ala Ala Ala Arg Asp Ile
465                 470             475                 480

Val Gln Phe Val Pro Tyr Arg Arg Phe Gln Asn Ala Pro Arg Glu Ala
            485             490               495

Leu Ala Gln Thr Val Leu Ala Glu Val Pro Thr Gln Leu Val Ser Tyr
            500             505               510

Phe Arg Ala Gln Gly Trp Ala Pro Leu Lys Pro Leu Pro Pro Ser Ala
            515             520               525

Lys Asp Pro Ala Gln Ala Pro Gln Ala
        530             535

<210> SEQ ID NO 12
<211> LENGTH: 623
<212> TYPE: PRT
<213> ORGANISM: Homo sapiens

<400> SEQUENCE: 12

Met Pro Pro Lys Val Thr Ser Glu Leu Leu Arg Gln Leu Arg Gln Ala
1               5               10              15

Met Arg Asn Ser Glu Tyr Val Thr Glu Pro Ile Gln Ala Tyr Ile Ile
            20              25              30

Pro Ser Gly Asp Ala His Gln Ser Glu Tyr Ile Ala Pro Cys Asp Cys
        35              40              45

Arg Arg Ala Phe Val Ser Gly Phe Asp Gly Ser Ala Gly Thr Ala Ile
    50              55              60

Ile Thr Glu Glu His Ala Ala Met Trp Thr Asp Gly Arg Tyr Phe Leu
65              70              75              80

Gln Ala Ala Lys Gln Met Asp Ser Asn Trp Thr Leu Met Lys Met Gly
                85              90              95

Leu Lys Asp Thr Pro Thr Gln Glu Asp Trp Leu Val Ser Val Leu Pro
            100             105             110

Glu Gly Ser Arg Val Gly Val Asp Pro Leu Ile Ile Pro Thr Asp Tyr
            115             120             125

Trp Lys Lys Met Ala Lys Val Leu Arg Ser Ala Gly His His Leu Ile
        130             135             140

Pro Val Lys Glu Asn Leu Val Asp Lys Ile Trp Thr Asp Arg Pro Glu
145             150             155             160

Arg Pro Cys Lys Pro Leu Leu Thr Leu Gly Leu Asp Tyr Thr Gly Ile
                165             170             175
```

-continued

```
Ser Trp Lys Asp Lys Val Ala Asp Leu Arg Leu Lys Met Ala Glu Arg
            180             185             190

Asn Val Met Trp Phe Val Val Thr Ala Leu Asp Glu Ile Ala Trp Leu
            195             200             205

Phe Asn Leu Arg Gly Ser Asp Val Glu His Asn Pro Val Phe Phe Ser
    210             215             220

Tyr Ala Ile Ile Gly Leu Glu Thr Ile Met Leu Phe Ile Asp Gly Asp
225             230             235             240

Arg Ile Asp Ala Pro Ser Val Lys Glu His Leu Leu Leu Asp Leu Gly
            245             250             255

Leu Glu Ala Glu Tyr Arg Ile Gln Val His Pro Tyr Lys Ser Ile Leu
            260             265             270

Ser Glu Leu Lys Ala Leu Cys Ala Asp Leu Ser Pro Arg Glu Lys Val
            275             280             285

Trp Val Ser Asp Lys Ala Ser Tyr Ala Val Ser Glu Thr Ile Pro Lys
            290             295             300

Asp His Arg Cys Cys Met Pro Tyr Thr Pro Ile Cys Ile Ala Lys Ala
305             310             315             320

Val Lys Asn Ser Ala Glu Ser Glu Gly Met Arg Arg Ala His Ile Lys
            325             330             335

Asp Ala Val Ala Leu Cys Glu Leu Phe Asn Trp Leu Glu Lys Glu Val
            340             345             350

Pro Lys Gly Gly Val Thr Glu Ile Ser Ala Ala Asp Lys Ala Glu Glu
            355             360             365

Phe Arg Arg Gln Gln Ala Asp Phe Val Asp Leu Ser Phe Pro Thr Ile
    370             375             380

Ser Ser Thr Gly Pro Asn Gly Ala Ile Ile His Tyr Ala Pro Val Pro
385             390             395             400

Glu Thr Asn Arg Thr Leu Ser Leu Asp Glu Val Tyr Leu Ile Asp Ser
            405             410             415

Gly Ala Gln Tyr Lys Asp Gly Thr Thr Asp Val Thr Arg Thr Met His
            420             425             430

Phe Gly Thr Pro Thr Ala Tyr Glu Lys Glu Cys Phe Thr Tyr Val Leu
            435             440             445

Lys Gly His Ile Ala Val Ser Ala Ala Val Phe Pro Thr Gly Thr Lys
    450             455             460

Gly His Leu Leu Asp Ser Phe Ala Arg Ser Ala Leu Trp Asp Ser Gly
465             470             475             480

Leu Asp Tyr Leu His Gly Thr Gly His Gly Val Gly Ser Phe Leu Asn
            485             490             495

Val His Glu Gly Pro Cys Gly Ile Ser Tyr Lys Thr Phe Ser Asp Glu
            500             505             510

Pro Leu Glu Ala Gly Met Ile Val Thr Asp Glu Pro Gly Tyr Tyr Glu
            515             520             525

Asp Gly Ala Phe Gly Ile Arg Ile Glu Asn Val Val Leu Val Val Pro
    530             535             540

Val Lys Thr Lys Tyr Asn Phe Asn Asn Arg Gly Ser Leu Thr Phe Glu
545             550             555             560

Pro Leu Thr Leu Val Pro Ile Gln Thr Lys Met Ile Asp Val Asp Ser
            565             570             575

Leu Thr Asp Lys Glu Cys Asp Trp Leu Asn Asn Tyr His Leu Thr Cys
            580             585             590

Arg Asp Val Ile Gly Lys Glu Leu Gln Lys Gln Gly Arg Gln Glu Ala
```

-continued

```
            595                 600                 605
Leu Glu Trp Leu Ile Arg Glu Thr Gln Pro Ile Ser Lys Gln His
    610                 615                 620

<210> SEQ ID NO 13
<211> LENGTH: 229
<212> TYPE: PRT
<213> ORGANISM: Homo sapiens

<400> SEQUENCE: 13

Met Ser Gln Gly Asp Ser Asn Pro Ala Ala Ile Pro His Ala Ala Glu
1               5                   10                  15

Asp Ile Gln Gly Asp Asp Arg Trp Met Ser Gln His Asn Arg Phe Val
                20                  25                  30

Leu Asp Cys Lys Asp Lys Glu Pro Asp Val Leu Phe Val Gly Asp Ser
            35                  40                  45

Met Val Gln Leu Met Gln Gln Tyr Glu Ile Trp Arg Glu Leu Phe Ser
        50                  55                  60

Pro Leu His Ala Leu Asn Phe Gly Ile Gly Gly Asp Thr Thr Arg His
65                  70                  75                  80

Val Leu Trp Arg Leu Lys Asn Gly Glu Leu Glu Asn Ile Lys Pro Lys
                85                  90                  95

Val Ile Val Val Trp Val Gly Thr Asn Asn His Glu Asn Thr Ala Glu
            100                 105                 110

Glu Val Ala Gly Gly Ile Glu Ala Ile Val Gln Leu Ile Asn Thr Arg
            115                 120                 125

Gln Pro Gln Ala Lys Ile Ile Val Leu Gly Leu Leu Pro Arg Gly Glu
        130                 135                 140

Lys Pro Asn Pro Leu Arg Gln Lys Asn Ala Lys Val Asn Gln Leu Leu
145                 150                 155                 160

Lys Val Ser Leu Pro Lys Leu Ala Asn Val Gln Leu Leu Asp Thr Asp
                165                 170                 175

Gly Gly Phe Val His Ser Asp Gly Ala Ile Ser Cys His Asp Met Phe
                180                 185                 190

Asp Phe Leu His Leu Thr Gly Gly Gly Tyr Ala Lys Ile Cys Lys Pro
            195                 200                 205

Leu His Glu Leu Ile Met Gln Leu Leu Glu Glu Thr Pro Glu Glu Lys
    210                 215                 220

Gln Thr Thr Ile Ala
225

<210> SEQ ID NO 14
<211> LENGTH: 460
<212> TYPE: PRT
<213> ORGANISM: Homo sapiens

<400> SEQUENCE: 14

Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
                20                  25                  30

Pro Ser Lys Ser Asn Pro Gly Asp Phe Thr Leu Ser Val Arg Arg Asn
            35                  40                  45

Gly Ala Val Thr His Ile Lys Ile Gln Asn Thr Gly Asp Tyr Tyr Asp
        50                  55                  60

Leu Tyr Gly Gly Glu Lys Phe Ala Thr Leu Ala Glu Leu Val Gln Tyr
```

```
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
            115                 120                 125

Lys Gly Lys His Gly Ser Phe Leu Val Arg Glu Ser Gln Ser His Pro
        130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
            195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
            275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
            325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
            355                 360                 365

Lys Tyr Trp Pro Asp Glu Tyr Ala Leu Lys Glu Tyr Gly Val Met Arg
    370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
            405                 410                 415

Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
            435                 440                 445

Ile Met Asp Ala Gly Pro Val Val Val His Cys Arg
    450                 455                 460
```

<210> SEQ ID NO 15
<211> LENGTH: 676
<212> TYPE: PRT
<213> ORGANISM: Homo sapiens -continued

<400> SEQUENCE: 15

```
Met Ala Pro Phe Leu Arg Ile Ala Phe Asn Ser Tyr Glu Leu Gly Ser
1               5                   10                  15

Leu Gln Ala Glu Asp Glu Ala Asn Gln Pro Phe Cys Ala Val Lys Met
                20                  25                  30

Lys Glu Ala Leu Ser Thr Glu Arg Gly Lys Thr Leu Val Gln Lys Lys
        35                  40                  45

Pro Thr Met Tyr Pro Glu Trp Lys Ser Thr Phe Asp Ala His Ile Tyr
        50                  55                  60

Glu Gly Arg Val Ile Gln Ile Val Leu Met Arg Ala Ala Glu Glu Pro
65                  70                  75                  80

Val Ser Glu Val Thr Val Gly Val Ser Val Leu Ala Glu Arg Cys Lys
                85                  90                  95

Lys Asn Asn Gly Lys Ala Glu Phe Trp Leu Asp Leu Gln Pro Gln Ala
                100                 105                 110

Lys Val Leu Met Ser Val Gln Tyr Phe Leu Glu Asp Val Asp Cys Lys
        115                 120                 125

Gln Ser Met Arg Ser Glu Asp Glu Ala Lys Phe Pro Thr Met Asn Arg
        130                 135                 140

Arg Gly Ala Ile Lys Gln Ala Lys Ile His Tyr Ile Lys Asn His Glu
145                 150                 155                 160

Phe Ile Ala Thr Phe Phe Gly Gln Pro Thr Phe Cys Ser Val Cys Lys
                165                 170                 175

Asp Phe Val Trp Gly Leu Asn Lys Gln Gly Tyr Lys Cys Arg Gln Cys
                180                 185                 190

Asn Ala Ala Ile His Lys Lys Cys Ile Asp Lys Ile Ile Gly Arg Cys
        195                 200                 205

Thr Gly Thr Ala Ala Asn Ser Arg Asp Thr Ile Phe Gln Lys Glu Arg
        210                 215                 220

Phe Asn Ile Asp Met Pro His Arg Phe Lys Val His Asn Tyr Met Ser
225                 230                 235                 240

Pro Thr Phe Cys Asp His Cys Gly Ser Leu Leu Trp Gly Leu Val Lys
                245                 250                 255

Gln Gly Leu Lys Cys Glu Asp Cys Gly Met Asn Val His His Lys Cys
        260                 265                 270

Arg Glu Lys Val Ala Asn Leu Cys Gly Ile Asn Gln Lys Leu Leu Ala
        275                 280                 285

Glu Ala Leu Asn Gln Val Thr Gln Arg Ala Ser Arg Arg Ser Asp Ser
        290                 295                 300

Ala Ser Ser Glu Pro Val Gly Ile Tyr Gln Gly Phe Glu Lys Lys Thr
305                 310                 315                 320

Gly Val Ala Gly Glu Asp Met Gln Asp Asn Ser Gly Thr Tyr Gly Lys
                325                 330                 335

Ile Trp Glu Gly Ser Ser Lys Cys Asn Ile Asn Asn Phe Ile Phe His
                340                 345                 350

Lys Val Leu Gly Lys Gly Ser Phe Gly Lys Val Leu Leu Gly Glu Leu
        355                 360                 365

Lys Gly Arg Gly Glu Tyr Phe Ala Ile Lys Ala Leu Lys Lys Asp Val
        370                 375                 380

Val Leu Ile Asp Asp Asp Val Glu Cys Thr Met Val Glu Lys Arg Val
385                 390                 395                 400

Leu Thr Leu Ala Ala Glu Asn Pro Phe Leu Thr His Leu Ile Cys Thr
```

-continued

```
                405                 410                 415

Phe Gln Thr Lys Asp His Leu Phe Phe Val Met Glu Phe Leu Asn Gly
            420                 425                 430

Gly Asp Leu Met Tyr His Ile Gln Asp Lys Gly Arg Phe Glu Leu Tyr
            435                 440                 445

Arg Ala Thr Phe Tyr Ala Ala Glu Ile Met Cys Gly Leu Gln Phe Leu
        450                 455                 460

His Ser Lys Gly Ile Ile Tyr Arg Asp Leu Lys Leu Asp Asn Val Leu
465                 470                 475                 480

Leu Asp Arg Asp Gly His Ile Lys Ile Ala Asp Phe Gly Met Cys Lys
                485                 490                 495

Glu Asn Ile Phe Gly Glu Ser Arg Ala Ser Thr Phe Cys Gly Thr Pro
            500                 505                 510

Asp Tyr Ile Ala Pro Glu Ile Leu Gln Gly Leu Lys Tyr Thr Phe Ser
            515                 520                 525

Val Asp Trp Trp Ser Phe Gly Val Leu Leu Tyr Glu Met Leu Ile Gly
        530                 535                 540

Gln Ser Pro Phe His Gly Asp Asp Glu Asp Glu Leu Phe Glu Ser Ile
545                 550                 555                 560

Arg Val Asp Thr Pro His Tyr Pro Arg Trp Ile Thr Lys Glu Ser Lys
                565                 570                 575

Asp Ile Leu Glu Lys Leu Phe Glu Arg Glu Pro Thr Lys Arg Leu Gly
            580                 585                 590

Val Thr Gly Asn Ile Lys Ile His Pro Phe Phe Lys Thr Ile Asn Trp
            595                 600                 605

Thr Leu Leu Glu Lys Arg Arg Leu Glu Pro Pro Phe Arg Pro Lys Val
        610                 615                 620

Lys Ser Pro Arg Asp Tyr Ser Asn Phe Asp Gln Glu Phe Leu Asn Glu
625                 630                 635                 640

Lys Ala Arg Leu Ser Tyr Ser Asp Lys Asn Leu Ile Asp Ser Met Asp
                645                 650                 655

Gln Ser Ala Phe Ala Gly Phe Ser Phe Val Asn Pro Lys Phe Glu His
            660                 665                 670

Leu Leu Glu Asp
            675

<210> SEQ ID NO 16
<211> LENGTH: 268
<212> TYPE: PRT
<213> ORGANISM: Homo sapiens

<400> SEQUENCE: 16

Met Ser Leu Ser Phe Leu Leu Leu Leu Phe Phe Ser His Leu Ile Leu
1               5                   10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Ser Arg Gln
            35                  40                  45

Ser Ser Ser Ser Ala Met Ser Ser Ser Ala Ser Ser Ser Pro Ala
        50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95
```

-continued

```
Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
        115                 120                 125

Gly Ile Val Gly Ile Arg Gly Val Phe Ser Asn Lys Phe Leu Ala Met
    130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Lys Pro Pro
225                 230                 235                 240

Ser Pro Ile Lys Pro Lys Ile Pro Leu Ser Ala Pro Arg Lys Asn Thr
                245                 250                 255

Asn Ser Val Lys Tyr Arg Leu Lys Phe Arg Phe Gly
            260                 265
```

<210> SEQ ID NO 17
<211> LENGTH: 184
<212> TYPE: PRT
<213> ORGANISM: Homo sapiens

<400> SEQUENCE: 17

```
Met Lys Ser Val Leu Leu Leu Thr Thr Leu Leu Val Pro Ala His Leu
1               5                   10                  15

Val Ala Ala Trp Ser Asn Asn Tyr Ala Val Asp Cys Pro Gln His Cys
            20                  25                  30

Asp Ser Ser Glu Cys Lys Ser Ser Pro Arg Cys Glu Arg Thr Val Leu
        35                  40                  45

Asp Asp Cys Gly Cys Cys Arg Val Cys Ala Ala Gly Arg Gly Glu Thr
    50                  55                  60

Cys Tyr Arg Thr Val Ser Gly Met Asp Gly Met Lys Cys Gly Pro Gly
65                  70                  75                  80

Leu Arg Cys Gln Pro Ser Asn Gly Glu Asp Pro Phe Gly Glu Glu Phe
                85                  90                  95

Gly Ile Cys Lys Asp Cys Pro Tyr Gly Thr Phe Gly Met Asp Cys Arg
            100                 105                 110

Glu Thr Cys Asn Cys Gln Ser Gly Ile Cys Asp Arg Gly Thr Gly Lys
        115                 120                 125

Cys Leu Lys Phe Pro Phe Phe Gln Tyr Ser Val Thr Lys Ser Ser Asn
    130                 135                 140

Arg Phe Val Ser Leu Thr Glu His Asp Met Ala Ser Gly Asp Gly Asn
145                 150                 155                 160

Ile Val Arg Glu Glu Val Val Lys Glu Asn Ala Ala Gly Ser Pro Val
                165                 170                 175

Met Arg Lys Trp Leu Asn Pro Arg
            180
```

<210> SEQ ID NO 18

<211> LENGTH: 101
<212> TYPE: PRT
<213> ORGANISM: Homo sapiens

<400> SEQUENCE: 18

Met Ser Asn Thr Gln Ala Glu Arg Ser Ile Ile Gly Met Ile Asp Met
1               5                   10                  15

Phe His Lys Tyr Thr Arg Arg Asp Asp Lys Ile Asp Lys Pro Ser Leu
            20                  25                  30

Leu Thr Met Met Lys Glu Asn Phe Pro Asn Phe Leu Ser Ala Cys Asp
        35                  40                  45

Lys Lys Gly Thr Asn Tyr Leu Ala Asp Val Phe Glu Lys Lys Asp Lys
    50                  55                  60

Asn Glu Asp Lys Lys Ile Asp Phe Ser Glu Phe Leu Ser Leu Leu Gly
65                  70                  75                  80

Asp Ile Ala Thr Asp Tyr His Lys Gln Ser His Gly Ala Ala Pro Cys
                85                  90                  95

Ser Gly Gly Ser Gln
            100

<210> SEQ ID NO 19
<211> LENGTH: 228
<212> TYPE: PRT
<213> ORGANISM: Homo sapiens

<400> SEQUENCE: 19

Met Ala Asp Phe Asp Thr Tyr Asp Asp Arg Ala Tyr Ser Ser Phe Gly
1               5                   10                  15

Gly Gly Arg Gly Ser Arg Gly Ser Ala Gly Gly His Gly Ser Arg Ser
            20                  25                  30

Gln Lys Glu Leu Pro Thr Glu Pro Pro Tyr Thr Ala Tyr Val Gly Asn
        35                  40                  45

Leu Pro Phe Asn Thr Val Gln Gly Asp Ile Asp Ala Ile Phe Lys Asp
    50                  55                  60

Leu Ser Ile Arg Ser Val Arg Leu Val Arg Asp Lys Asp Thr Asp Lys
65                  70                  75                  80

Phe Lys Gly Phe Cys Tyr Val Glu Phe Asp Glu Val Asp Ser Leu Lys
                85                  90                  95

Glu Ala Leu Thr Tyr Asp Gly Ala Leu Leu Gly Asp Arg Ser Leu Arg
            100                 105                 110

Val Asp Ile Ala Glu Gly Arg Lys Gln Asp Lys Gly Gly Phe Gly Phe
        115                 120                 125

Arg Lys Gly Gly Pro Asp Asp Arg Gly Phe Arg Asp Asp Phe Leu Gly
    130                 135                 140

Gly Arg Gly Gly Ser Arg Pro Gly Asp Arg Arg Thr Gly Pro Pro Met
145                 150                 155                 160

Gly Ser Arg Phe Arg Asp Gly Pro Pro Leu Arg Gly Ser Asn Met Asp
                165                 170                 175

Phe Arg Glu Pro Thr Glu Glu Glu Arg Ala Gln Arg Pro Arg Leu Gln
            180                 185                 190

Leu Lys Pro Arg Thr Val Ala Thr Pro Leu Asn Gln Val Ala Asn Pro
            195                 200                 205

Asn Ser Ala Ile Phe Gly Gly Ala Arg Pro Arg Glu Glu Val Val Gln
        210                 215                 220

Lys Glu Gln Glu
225

```
<210> SEQ ID NO 20
<211> LENGTH: 606
<212> TYPE: PRT
<213> ORGANISM: Homo sapiens

<400> SEQUENCE: 20

Met Arg Arg Arg Ala Ala Arg Gly Pro Gly Pro Pro Pro Gly Pro
1               5                  10                 15

Gly Leu Ser Arg Leu Pro Leu Leu Pro Leu Pro Leu Leu Leu Leu
            20                 25                 30

Ala Leu Gly Thr Arg Gly Gly Cys Ala Ala Pro Ala Pro Ala Pro Arg
        35                 40                 45

Ala Glu Asp Leu Ser Leu Gly Val Glu Trp Leu Ser Arg Phe Gly Tyr
    50                 55                 60

Leu Pro Pro Ala Asp Pro Thr Thr Gly Gln Leu Gln Thr Gln Glu Glu
65                 70                 75                 80

Leu Ser Lys Ala Ile Thr Ala Met Gln Gln Phe Gly Gly Leu Glu Ala
            85                 90                 95

Thr Gly Ile Leu Asp Glu Ala Thr Leu Ala Leu Met Lys Thr Pro Arg
            100                105                110

Cys Ser Leu Pro Asp Leu Pro Val Leu Thr Gln Ala Arg Arg Arg Arg
            115                120                125

Gln Ala Pro Ala Pro Thr Lys Trp Asn Lys Arg Asn Leu Ser Trp Arg
    130                135                140

Val Arg Thr Phe Pro Arg Asp Ser Pro Leu Gly His Asp Thr Val Arg
145                150                155                160

Ala Leu Met Tyr Tyr Ala Leu Lys Val Trp Ser Asp Ile Ala Pro Leu
            165                170                175

Asn Phe His Glu Val Ala Gly Ser Thr Ala Asp Ile Gln Ile Asp Phe
            180                185                190

Ser Lys Ala Asn His Asn Asp Gly Tyr Pro Phe Asp Gly Pro Gly Gly
            195                200                205

Thr Val Ala His Ala Phe Phe Pro Gly His His Asn Thr Ala Gly Asp
    210                215                220

Thr His Phe Asp Asp Asp Glu Ala Trp Thr Phe Arg Ser Ser Asp Ala
225                230                235                240

His Gly Met Asp Leu Phe Ala Val Ala Val His Glu Phe Gly His Ala
            245                250                255

Ile Gly Leu Ser His Val Ala Ala Ala His Ser Ile Met Arg Pro Tyr
            260                265                270

Tyr Gln Gly Pro Val Gly Asp Pro Leu Arg Tyr Gly Leu Pro Tyr Glu
            275                280                285

Asp Lys Val Arg Val Trp Gln Leu Tyr Gly Val Arg Glu Ser Val Ser
    290                295                300

Pro Thr Ala Gln Pro Glu Glu Pro Pro Leu Leu Pro Glu Pro Pro Asp
305                310                315                320

Asn Arg Ser Ser Ala Pro Pro Arg Lys Asp Val Pro His Arg Cys Ser
            325                330                335

Thr His Phe Asp Ala Val Ala Gln Ile Arg Gly Glu Ala Phe Phe Phe
            340                345                350

Lys Gly Lys Tyr Phe Trp Arg Leu Thr Arg Asp Arg His Leu Val Ser
            355                360                365

Leu Gln Pro Ala Gln Met His Arg Phe Trp Arg Gly Leu Pro Leu His
```

```
        370              375              380

Leu Asp Ser Val Asp Ala Val Tyr Glu Arg Thr Ser Asp His Lys Ile
385              390              395              400

Val Phe Phe Lys Gly Asp Arg Tyr Trp Val Phe Lys Asp Asn Asn Val
                 405              410              415

Glu Glu Gly Tyr Pro Arg Pro Val Ser Asp Phe Ser Leu Pro Pro Gly
                 420              425              430

Gly Ile Asp Ala Ala Phe Ser Trp Ala His Asn Asp Arg Thr Tyr Phe
                 435              440              445

Phe Lys Asp Gln Leu Tyr Trp Arg Tyr Asp Asp His Thr Arg His Met
    450              455              460

Asp Pro Gly Tyr Pro Ala Gln Ser Pro Leu Trp Arg Gly Val Pro Ser
465              470              475              480

Thr Leu Asp Asp Ala Met Arg Trp Ser Asp Gly Ala Tyr Tyr Phe Phe
                 485              490              495

Arg Gly Gln Glu Tyr Trp Lys Val Leu Asp Gly Glu Leu Glu Val Ala
                 500              505              510

Pro Gly Tyr Pro Gln Ser Thr Ala Arg Asp Trp Leu Val Cys Gly Asp
                 515              520              525

Ser Gln Ala Asp Gly Ser Val Ala Ala Gly Val Asp Ala Ala Glu Gly
    530              535              540

Pro Arg Ala Pro Pro Gly Gln His Asp Gln Ser Arg Ser Glu Asp Gly
545              550              555              560

Tyr Glu Val Cys Ser Cys Thr Ser Gly Ala Ser Ser Pro Pro Gly Ala
                 565              570              575

Pro Gly Pro Leu Val Ala Ala Thr Met Leu Leu Leu Leu Pro Pro Leu
                 580              585              590

Ser Pro Gly Ala Leu Trp Thr Ala Ala Gln Ala Leu Thr Leu
                 595              600              605
```

<210> SEQ ID NO 21
<211> LENGTH: 425
<212> TYPE: PRT
<213> ORGANISM: Homo sapiens

<400> SEQUENCE: 21

```
Met Ser Ser Ile Leu Pro Phe Thr Pro Pro Ile Val Lys Arg Leu Leu
1               5               10               15

Gly Trp Lys Lys Gly Glu Gln Asn Gly Gln Glu Glu Lys Trp Cys Glu
                 20              25               30

Lys Ala Val Lys Ser Leu Val Lys Lys Leu Lys Lys Thr Gly Gln Leu
                 35              40               45

Asp Glu Leu Glu Lys Ala Ile Thr Thr Gln Asn Val Asn Thr Lys Cys
    50              55               60

Ile Thr Ile Pro Arg Ser Leu Asp Gly Arg Leu Gln Val Ser His Arg
65              70               75               80

Lys Gly Leu Pro His Val Ile Tyr Cys Arg Leu Trp Arg Trp Pro Asp
                 85              90               95

Leu His Ser His His Glu Leu Arg Ala Met Glu Leu Cys Glu Phe Ala
                 100             105              110

Phe Asn Met Lys Lys Asp Glu Val Cys Val Asn Pro Tyr His Tyr Gln
                 115             120              125

Arg Val Glu Thr Pro Val Leu Pro Pro Val Leu Val Pro Arg His Thr
    130             135              140
```

-continued

```
Glu Ile Pro Ala Glu Phe Pro Pro Leu Asp Asp Tyr Ser His Ser Ile
145                 150                 155                 160

Pro Glu Asn Thr Asn Phe Pro Ala Gly Ile Glu Pro Gln Ser Asn Ile
                165                 170                 175

Pro Glu Thr Pro Pro Pro Gly Tyr Leu Ser Glu Asp Gly Glu Thr Ser
                180                 185                 190

Asp His Gln Met Asn His Ser Met Asp Ala Gly Ser Pro Asn Leu Ser
                195                 200                 205

Pro Asn Pro Met Ser Pro Ala His Asn Asn Leu Asp Leu Gln Pro Val
                210                 215                 220

Thr Tyr Cys Glu Pro Ala Phe Trp Cys Ser Ile Ser Tyr Tyr Glu Leu
225                 230                 235                 240

Asn Gln Arg Val Gly Glu Thr Phe His Ala Ser Gln Pro Ser Met Thr
                245                 250                 255

Val Asp Gly Phe Thr Asp Pro Ser Asn Ser Glu Arg Phe Cys Leu Gly
                260                 265                 270

Leu Leu Ser Asn Val Asn Arg Asn Ala Ala Val Glu Leu Thr Arg Arg
                275                 280                 285

His Ile Gly Arg Gly Val Arg Leu Tyr Tyr Ile Gly Gly Glu Val Phe
                290                 295                 300

Ala Glu Cys Leu Ser Asp Ser Ala Ile Phe Val Gln Ser Pro Asn Cys
305                 310                 315                 320

Asn Gln Arg Tyr Gly Trp His Pro Ala Thr Val Cys Lys Ile Pro Pro
                325                 330                 335

Gly Cys Asn Leu Lys Ile Phe Asn Asn Gln Glu Phe Ala Ala Leu Leu
                340                 345                 350

Ala Gln Ser Val Asn Gln Gly Phe Glu Ala Val Tyr Gln Leu Thr Arg
                355                 360                 365

Met Cys Thr Ile Arg Met Ser Phe Val Lys Gly Trp Gly Ala Glu Tyr
                370                 375                 380

Arg Arg Gln Thr Val Thr Ser Thr Pro Cys Trp Ile Glu Leu His Leu
385                 390                 395                 400

Asn Gly Pro Leu Gln Trp Leu Asp Lys Val Leu Thr Gln Met Gly Ser
                405                 410                 415

Pro Ser Ile Arg Cys Ser Ser Val Ser
                420                 425

<210> SEQ ID NO 22
<211> LENGTH: 1356
<212> TYPE: PRT
<213> ORGANISM: Homo sapiens

<400> SEQUENCE: 22

Met Glu Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95
```

```
Asp Thr Gly Ala Tyr Lys Cys Phe Tyr Arg Glu Thr Asp Leu Ala Ser
        100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
        130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Val Gly Tyr Arg Ile Tyr
        210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
                275                 280                 285

Leu Ser Thr Leu Thr Ile Asp Gly Val Thr Arg Ser Asp Gln Gly Leu
        290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
                340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
        370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
        450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
        500                 505                 510
```

```
Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
        530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
                580                 585                 590

Ile His Val Gly Glu Leu Pro Thr Pro Val Cys Lys Asn Leu Asp Thr
                595                 600                 605

Leu Trp Lys Leu Asn Ala Thr Met Phe Ser Asn Ser Thr Asn Asp Ile
        610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
        690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
        740                 745                 750

Ile Ile Glu Gly Ala Gln Glu Lys Thr Asn Leu Glu Ile Ile Ile Leu
        755                 760                 765

Val Gly Thr Ala Val Ile Ala Met Phe Phe Trp Leu Leu Leu Val Ile
        770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
        820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
        850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
```

-continued

```
        930              935              940
Phe Arg Gln Gly Lys Asp Tyr Val Gly Ala Ile Pro Val Asp Leu Lys
945                 950                955                 960

Arg Arg Leu Asp Ser Ile Thr Ser Ser Gln Ser Ser Ala Ser Ser Gly
                965                970                975

Phe Val Glu Glu Lys Ser Leu Ser Asp Val Glu Glu Glu Glu Ala Pro
                980                985                990

Glu Asp Leu Tyr Lys Asp Phe Leu Thr Leu Glu His Leu Ile Cys Tyr
            995                1000               1005

Ser Phe Gln Val Ala Lys Gly Met Glu Phe Leu Ala Ser Arg Lys
        1010               1015               1020

Cys Ile His Arg Asp Leu Ala Ala Arg Asn Ile Leu Leu Ser Glu
        1025               1030               1035

Lys Asn Val Val Lys Ile Cys Asp Phe Gly Leu Ala Arg Asp Ile
        1040               1045               1050

Tyr Lys Asp Pro Asp Tyr Val Arg Lys Gly Asp Ala Arg Leu Pro
        1055               1060               1065

Leu Lys Trp Met Ala Pro Glu Thr Ile Phe Asp Arg Val Tyr Thr
        1070               1075               1080

Ile Gln Ser Asp Val Trp Ser Phe Gly Val Leu Leu Trp Glu Ile
        1085               1090               1095

Phe Ser Leu Gly Ala Ser Pro Tyr Pro Gly Val Lys Ile Asp Glu
        1100               1105               1110

Glu Phe Cys Arg Arg Leu Lys Glu Gly Thr Arg Met Arg Ala Pro
        1115               1120               1125

Asp Tyr Thr Thr Pro Glu Met Tyr Gln Thr Met Leu Asp Cys Trp
        1130               1135               1140

His Gly Glu Pro Ser Gln Arg Pro Thr Phe Ser Glu Leu Val Glu
        1145               1150               1155

His Leu Gly Asn Leu Leu Gln Ala Asn Ala Gln Gln Asp Gly Lys
        1160               1165               1170

Asp Tyr Ile Val Leu Pro Ile Ser Glu Thr Leu Ser Met Glu Glu
        1175               1180               1185

Asp Ser Gly Leu Ser Leu Pro Thr Ser Pro Val Ser Cys Met Glu
        1190               1195               1200

Glu Glu Glu Val Cys Asp Pro Lys Phe His Tyr Asp Asn Thr Ala
        1205               1210               1215

Gly Ile Ser Gln Tyr Leu Gln Asn Ser Lys Arg Lys Ser Arg Pro
        1220               1225               1230

Val Ser Val Lys Thr Phe Glu Asp Ile Pro Leu Glu Glu Pro Glu
        1235               1240               1245

Val Lys Val Ile Pro Asp Asp Asn Gln Thr Asp Ser Gly Met Val
        1250               1255               1260

Leu Ala Ser Glu Glu Leu Lys Thr Leu Glu Asp Arg Thr Lys Leu
        1265               1270               1275

Ser Pro Ser Phe Gly Gly Met Val Pro Ser Lys Ser Arg Glu Ser
        1280               1285               1290

Val Ala Ser Glu Gly Ser Asn Gln Thr Ser Gly Tyr Gln Ser Gly
        1295               1300               1305

Tyr His Ser Asp Asp Thr Asp Thr Thr Val Tyr Ser Ser Glu Glu
        1310               1315               1320

Ala Glu Leu Leu Lys Leu Ile Glu Ile Gly Val Gln Thr Gly Ser
        1325               1330               1335
```

-continued

```
Thr Ala Gln Ile Leu Gln Pro  Asp Ser Gly Thr Thr  Leu Ser Ser
    1340             1345             1350

Pro Pro Val
    1355

<210> SEQ ID NO 23
<211> LENGTH: 1124
<212> TYPE: PRT
<213> ORGANISM: Homo sapiens

<400> SEQUENCE: 23

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
            115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
            165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
            195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
            245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
            275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
            325                 330                 335

Gly Leu Gln Cys Glu Arg Glu Gly Ile Pro Arg Met Thr Pro Lys Ile
```

-continued

```
              340             345                 350

Val Asp Leu Pro Asp His Ile Glu Val Asn Ser Gly Lys Phe Asn Pro
          355             360                 365

Ile Cys Lys Ala Ser Gly Trp Pro Leu Pro Thr Asn Glu Glu Met Thr
          370             375             380

Leu Val Lys Pro Asp Gly Thr Val Leu His Pro Lys Asp Phe Asn His
385                 390             395                 400

Thr Asp His Phe Ser Val Ala Ile Phe Thr Ile His Arg Ile Leu Pro
              405             410                 415

Pro Asp Ser Gly Val Trp Val Cys Ser Val Asn Thr Val Ala Gly Met
          420             425             430

Val Glu Lys Pro Phe Asn Ile Ser Val Lys Val Leu Pro Lys Pro Leu
          435             440             445

Asn Ala Pro Asn Val Ile Asp Thr Gly His Asn Phe Ala Val Ile Asn
          450             455             460

Ile Ser Ser Glu Pro Tyr Phe Gly Asp Gly Pro Ile Lys Ser Lys Lys
465                 470             475                 480

Leu Leu Tyr Lys Pro Val Asn His Tyr Glu Ala Trp Gln His Ile Gln
              485             490                 495

Val Thr Asn Glu Ile Val Thr Leu Asn Tyr Leu Glu Pro Arg Thr Glu
          500             505             510

Tyr Glu Leu Cys Val Gln Leu Val Arg Arg Gly Glu Gly Gly Glu Gly
          515             520             525

His Pro Gly Pro Val Arg Arg Phe Thr Thr Ala Ser Ile Gly Leu Pro
          530             535             540

Pro Pro Arg Gly Leu Asn Leu Leu Pro Lys Ser Gln Thr Thr Leu Asn
545                 550             555                 560

Leu Thr Trp Gln Pro Ile Phe Pro Ser Ser Glu Asp Asp Phe Tyr Val
              565             570                 575

Glu Val Glu Arg Arg Ser Val Gln Lys Ser Asp Gln Gln Asn Ile Lys
              580             585                 590

Val Pro Gly Asn Leu Thr Ser Val Leu Leu Asn Asn Leu His Pro Arg
          595             600             605

Glu Gln Tyr Val Val Arg Ala Arg Val Asn Thr Lys Ala Gln Gly Glu
          610             615             620

Trp Ser Glu Asp Leu Thr Ala Trp Thr Leu Ser Asp Ile Leu Pro Pro
625                 630             635                 640

Gln Pro Glu Asn Ile Lys Ile Ser Asn Ile Thr His Ser Ser Ala Val
              645             650                 655

Ile Ser Trp Thr Ile Leu Asp Gly Tyr Ser Ile Ser Ser Ile Thr Ile
              660             665             670

Arg Tyr Lys Val Gln Gly Lys Asn Glu Asp Gln His Val Asp Val Lys
              675             680             685

Ile Lys Asn Ala Thr Ile Ile Gln Tyr Gln Leu Lys Gly Leu Glu Pro
          690             695             700

Glu Thr Ala Tyr Gln Val Asp Ile Phe Ala Glu Asn Asn Ile Gly Ser
705                 710             715                 720

Ser Asn Pro Ala Phe Ser His Glu Leu Val Thr Leu Pro Glu Ser Gln
              725             730                 735

Ala Pro Ala Asp Leu Gly Gly Gly Lys Met Leu Leu Ile Ala Ile Leu
              740             745             750

Gly Ser Ala Gly Met Thr Cys Leu Thr Val Leu Leu Ala Phe Leu Ile
          755             760             765
```

```
Ile Leu Gln Leu Lys Arg Ala Asn Val Gln Arg Arg Met Ala Gln Ala
    770             775             780
```

```
Phe Gln Asn Val Arg Glu Glu Pro Ala Val Gln Phe Asn Ser Gly Thr
785             790             795             800
```

```
Leu Ala Leu Asn Arg Lys Val Lys Asn Asn Pro Asp Pro Thr Ile Tyr
            805             810             815
```

```
Pro Val Leu Asp Trp Asn Asp Ile Lys Phe Gln Asp Val Ile Gly Glu
            820             825             830
```

```
Gly Asn Phe Gly Gln Val Leu Lys Ala Arg Ile Lys Lys Asp Gly Leu
            835             840             845
```

```
Arg Met Asp Ala Ala Ile Lys Arg Met Lys Glu Tyr Ala Ser Lys Asp
    850             855             860
```

```
Asp His Arg Asp Phe Ala Gly Glu Leu Glu Val Leu Cys Lys Leu Gly
865             870             875             880
```

```
His His Pro Asn Ile Ile Asn Leu Leu Gly Ala Cys Glu His Arg Gly
            885             890             895
```

```
Tyr Leu Tyr Leu Ala Ile Glu Tyr Ala Pro His Gly Asn Leu Leu Asp
    900             905             910
```

```
Phe Leu Arg Lys Ser Arg Val Leu Glu Thr Asp Pro Ala Phe Ala Ile
    915             920             925
```

```
Ala Asn Ser Thr Ala Ser Thr Leu Ser Ser Gln Gln Leu Leu His Phe
    930             935             940
```

```
Ala Ala Asp Val Ala Arg Gly Met Asp Tyr Leu Ser Gln Lys Gln Phe
945             950             955             960
```

```
Ile His Arg Asp Leu Ala Ala Arg Asn Ile Leu Val Gly Glu Asn Tyr
            965             970             975
```

```
Val Ala Lys Ile Ala Asp Phe Gly Leu Ser Arg Gly Gln Glu Val Tyr
            980             985             990
```

```
Val Lys Lys Thr Met Gly Arg Leu  Pro Val Arg Trp Met  Ala Ile Glu
        995             1000                1005
```

```
Ser Leu  Asn Tyr Ser Val Tyr  Thr Thr Asn Ser Asp  Val Trp Ser
    1010            1015                1020
```

```
Tyr Gly  Val Leu Leu Trp Glu  Ile Val Ser Leu Gly  Gly Thr Pro
    1025            1030                1035
```

```
Tyr Cys  Gly Met Thr Cys Ala  Glu Leu Tyr Glu Lys  Leu Pro Gln
    1040            1045                1050
```

```
Gly Tyr  Arg Leu Glu Lys Pro  Leu Asn Cys Asp Asp  Glu Val Tyr
    1055            1060                1065
```

```
Asp Leu  Met Arg Gln Cys Trp  Arg Glu Lys Pro Tyr  Glu Arg Pro
    1070            1075                1080
```

```
Ser Phe  Ala Gln Ile Leu Val  Ser Leu Asn Arg Met  Leu Glu Glu
    1085            1090                1095
```

```
Arg Lys  Thr Tyr Val Asn Thr  Thr Leu Tyr Glu Lys  Phe Thr Tyr
    1100            1105                1110
```

```
Ala Gly  Ile Asp Cys Ser Ala  Glu Glu Ala Ala
    1115            1120
```

<210> SEQ ID NO 24
<211> LENGTH: 669
<212> TYPE: PRT
<213> ORGANISM: Homo sapiens

<400> SEQUENCE: 24

```
Met Gln Arg Leu Met Met Leu Leu Ala Thr Ser Gly Ala Cys Leu Gly
```

-continued

```
1                5               10              15

Leu Leu Ala Val Ala Ala Val Ala Ala Ala Gly Ala Asn Pro Ala Gln
            20              25              30

Arg Asp Thr His Ser Leu Leu Pro Thr His Arg Arg Gln Lys Arg Asp
            35              40              45

Trp Ile Trp Asn Gln Met His Ile Asp Glu Glu Lys Asn Thr Ser Leu
    50              55              60

Pro His His Val Gly Lys Ile Lys Ser Ser Val Ser Arg Lys Asn Ala
65              70              75              80

Lys Tyr Leu Leu Lys Gly Glu Tyr Val Gly Lys Val Phe Arg Val Asp
            85              90              95

Ala Glu Thr Gly Asp Val Phe Ala Ile Glu Arg Leu Asp Arg Glu Asn
            100             105             110

Ile Ser Glu Tyr His Leu Thr Ala Val Ile Val Asp Lys Asp Thr Gly
            115             120             125

Glu Asn Leu Glu Thr Pro Ser Ser Phe Thr Ile Lys Val His Asp Val
    130             135             140

Asn Asp Asn Trp Pro Val Phe Thr His Arg Leu Phe Asn Ala Ser Val
145             150             155             160

Pro Glu Ser Ser Ala Val Gly Thr Ser Val Ile Ser Val Thr Ala Val
            165             170             175

Asp Ala Asp Asp Pro Thr Val Gly Asp His Ala Ser Val Met Tyr Gln
            180             185             190

Ile Leu Lys Gly Lys Glu Tyr Phe Ala Ile Asp Asn Ser Gly Arg Ile
            195             200             205

Ile Thr Ile Thr Lys Ser Leu Asp Arg Glu Lys Gln Ala Arg Tyr Glu
    210             215             220

Ile Val Val Glu Ala Arg Asp Ala Gln Gly Leu Arg Gly Asp Ser Gly
225             230             235             240

Thr Ala Thr Val Leu Val Thr Leu Gln Asp Ile Asn Asp Asn Phe Pro
            245             250             255

Phe Phe Thr Gln Thr Lys Tyr Thr Phe Val Val Pro Glu Asp Thr Arg
            260             265             270

Val Gly Thr Ser Val Gly Ser Leu Phe Val Glu Asp Pro Asp Glu Pro
            275             280             285

Gln Asn Arg Met Thr Lys Tyr Ser Ile Leu Arg Gly Asp Tyr Gln Asp
    290             295             300

Ala Phe Thr Ile Glu Thr Asn Pro Ala His Asn Glu Gly Ile Ile Lys
305             310             315             320

Pro Met Lys Pro Leu Asp Tyr Glu Tyr Ile Gln Gln Tyr Ser Phe Ile
            325             330             335

Val Glu Ala Thr Asp Pro Thr Ile Asp Leu Arg Tyr Met Ser Pro Pro
            340             345             350

Ala Gly Asn Arg Ala Gln Val Ile Ile Asn Ile Thr Asp Val Asp Glu
            355             360             365

Pro Pro Ile Phe Gln Gln Pro Phe Tyr His Phe Gln Leu Val Leu Gln
    370             375             380

Ile Ser Ala Ile Asp Lys Asp Ile Thr Pro Arg Asn Val Lys Phe Lys
385             390             395             400

Phe Thr Leu Asn Thr Glu Asn Asn Phe Thr Leu Thr Asp Asn His Asp
            405             410             415

Asn Thr Ala Asn Ile Thr Val Lys Tyr Gly Gln Phe Asp Arg Glu His
            420             425             430
```

```
Thr Lys Val His Phe Leu Pro Val Val Ile Ser Asp Asn Gly Met Pro
        435             440             445

Ser Arg Thr Gly Thr Ser Thr Leu Thr Val Ala Val Cys Lys Cys Asn
    450             455             460

Glu Gln Gly Glu Phe Thr Phe Cys Glu Asp Met Ala Ala Gln Val Gly
465             470             475             480

Val Ser Ile Gln Ala Val Val Ala Ile Leu Leu Cys Ile Leu Thr Ile
            485             490             495

Thr Val Ile Thr Leu Leu Ile Phe Leu Arg Arg Arg Leu Arg Lys Gln
            500             505             510

Ala Arg Ala His Gly Lys Ser Val Pro Glu Ile His Glu Gln Leu Val
        515             520             525

Thr Tyr Asp Glu Glu Gly Gly Gly Glu Met Asp Thr Thr Ser Tyr Asp
    530             535             540

Val Ser Val Leu Asn Ser Val Arg Arg Gly Gly Ala Lys Pro Pro Arg
545             550             555             560

Pro Ala Leu Asp Ala Arg Pro Ser Leu Tyr Ala Gln Val Gln Lys Pro
            565             570             575

Pro Arg His Ala Pro Gly Ala His Gly Gly Pro Gly Glu Met Ala Ala
        580             585             590

Met Ile Glu Val Lys Lys Asp Glu Ala Asp His Asp Gly Asp Gly Pro
    595             600             605

Pro Tyr Asp Thr Leu His Ile Tyr Gly Tyr Glu Gly Ser Glu Ser Ile
    610             615             620

Ala Glu Ser Leu Ser Ser Leu Gly Thr Asp Ser Ser Asp Ser Asp Val
625             630             635             640

Asp Tyr Asp Phe Leu Asn Asp Trp Gly Pro Arg Phe Lys Met Leu Ala
            645             650             655

Glu Leu Tyr Gly Ser Asp Pro Arg Glu Glu Leu Leu Tyr
            660             665
```

```
<210> SEQ ID NO 25
<211> LENGTH: 2556
<212> TYPE: PRT
<213> ORGANISM: Homo sapiens
<220> FEATURE:
<221> NAME/KEY: MOD_RES
<222> LOCATION: (891)..(891)
<223> OTHER INFORMATION: Any amino acid

<400> SEQUENCE: 25
```

```
Met Pro Pro Leu Leu Ala Pro Leu Leu Cys Leu Ala Leu Leu Pro Ala
1               5               10              15

Leu Ala Ala Arg Gly Pro Arg Cys Ser Gln Pro Gly Glu Thr Cys Leu
        20              25              30

Asn Gly Gly Lys Cys Glu Ala Ala Asn Gly Thr Glu Ala Cys Val Cys
        35              40              45

Gly Gly Ala Phe Val Gly Pro Arg Cys Gln Asp Pro Asn Pro Cys Leu
    50              55              60

Ser Thr Pro Cys Lys Asn Ala Gly Thr Cys His Val Val Asp Arg Arg
65              70              75              80

Gly Val Ala Asp Tyr Ala Cys Ser Cys Ala Leu Gly Phe Ser Gly Pro
            85              90              95

Leu Cys Leu Thr Pro Leu Asp Asn Ala Cys Leu Thr Asn Pro Cys Arg
        100             105             110
```

```
Asn Gly Gly Thr Cys Asp Leu Leu Thr Leu Thr Glu Tyr Lys Cys Arg
        115             120             125

Cys Pro Pro Gly Trp Ser Gly Lys Ser Cys Gln Gln Ala Asp Pro Cys
    130             135             140

Ala Ser Asn Pro Cys Ala Asn Gly Gly Gln Cys Leu Pro Phe Glu Ala
145             150             155             160

Ser Tyr Ile Cys His Cys Pro Pro Ser Phe His Gly Pro Thr Cys Arg
                165             170             175

Gln Asp Val Asn Glu Cys Gly Gln Lys Pro Arg Leu Cys Arg His Gly
            180             185             190

Gly Thr Cys His Asn Glu Val Gly Ser Tyr Arg Cys Val Cys Arg Ala
            195             200             205

Thr His Thr Gly Pro Asn Cys Glu Arg Pro Tyr Val Pro Cys Ser Pro
    210             215             220

Ser Pro Cys Gln Asn Gly Gly Thr Cys Arg Pro Thr Gly Asp Val Thr
225             230             235             240

His Glu Cys Ala Cys Leu Pro Gly Phe Thr Gly Gln Asn Cys Glu Glu
            245             250             255

Asn Ile Asp Asp Cys Pro Gly Asn Asn Cys Lys Asn Gly Gly Ala Cys
            260             265             270

Val Asp Gly Val Asn Thr Tyr Asn Cys Pro Cys Pro Pro Glu Trp Thr
            275             280             285

Gly Gln Tyr Cys Thr Glu Asp Val Asp Glu Cys Gln Leu Met Pro Asn
    290             295             300

Ala Cys Gln Asn Gly Gly Thr Cys His Asn Thr His Gly Gly Tyr Asn
305             310             315             320

Cys Val Cys Val Asn Gly Trp Thr Gly Glu Asp Cys Ser Glu Asn Ile
            325             330             335

Asp Asp Cys Ala Ser Ala Ala Cys Phe His Gly Ala Thr Cys His Asp
            340             345             350

Arg Val Ala Ser Phe Tyr Cys Glu Cys Pro His Gly Arg Thr Gly Leu
            355             360             365

Leu Cys His Leu Asn Asp Ala Cys Ile Ser Asn Pro Cys Asn Glu Gly
    370             375             380

Ser Asn Cys Asp Thr Asn Pro Val Asn Gly Lys Ala Ile Cys Thr Cys
385             390             395             400

Pro Ser Gly Tyr Thr Gly Pro Ala Cys Ser Gln Asp Val Asp Glu Cys
            405             410             415

Ser Leu Gly Ala Asn Pro Cys Glu His Ala Gly Lys Cys Ile Asn Thr
            420             425             430

Leu Gly Ser Phe Glu Cys Gln Cys Leu Gln Gly Tyr Thr Gly Pro Arg
            435             440             445

Cys Glu Ile Asp Val Asn Glu Cys Val Ser Asn Pro Cys Gln Asn Asp
    450             455             460

Ala Thr Cys Leu Asp Gln Ile Gly Glu Phe Gln Cys Met Cys Met Pro
465             470             475             480

Gly Tyr Glu Gly Val His Cys Glu Val Asn Thr Asp Glu Cys Ala Ser
            485             490             495

Ser Pro Cys Leu His Asn Gly Arg Cys Leu Asp Lys Ile Asn Glu Phe
            500             505             510

Gln Cys Glu Cys Pro Thr Gly Phe Thr Gly His Leu Cys Gln Tyr Asp
            515             520             525

Val Asp Glu Cys Ala Ser Thr Pro Cys Lys Asn Gly Ala Lys Cys Leu
```

-continued

```
        530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
                580                 585                 590

Pro Gly Tyr Thr Gly His His Cys Glu Thr Asn Ile Asn Glu Cys Ser
                595                 600                 605

Ser Gln Pro Cys Arg Leu Arg Gly Thr Cys Gln Asp Pro Asp Asn Ala
        610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
                660                 665                 670

Ser Met Cys Asn Ser Asn Ile Asp Glu Cys Ala Gly Asn Pro Cys His
                675                 680                 685

Asn Gly Gly Thr Cys Glu Asp Gly Ile Asn Gly Phe Thr Cys Arg Cys
        690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
                740                 745                 750

Asn Asn Asn Glu Cys Glu Ser Asn Pro Cys Val Asn Gly Gly Thr Cys
                755                 760                 765

Lys Asp Met Thr Ser Gly Ile Val Cys Thr Cys Arg Glu Gly Phe Ser
        770                 775                 780

Gly Pro Asn Cys Gln Thr Asn Ile Asn Glu Cys Ala Ser Asn Pro Cys
785                 790                 795                 800

Leu Asn Lys Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
                820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Ala Gly Ala Lys Gly
        850                 855                 860

Gln Thr Cys Glu Val Asp Ile Asn Glu Cys Val Leu Ser Pro Cys Arg
865                 870                 875                 880

His Gly Ala Ser Cys Gln Asn Thr His Gly Xaa Tyr Arg Cys His Cys
                885                 890                 895

Gln Ala Gly Tyr Ser Gly Arg Asn Cys Glu Thr Asp Ile Asp Asp Cys
                900                 905                 910

Arg Pro Asn Pro Cys His Asn Gly Gly Ser Cys Thr Asp Gly Ile Asn
                915                 920                 925

Thr Ala Phe Cys Asp Cys Leu Pro Gly Phe Arg Gly Thr Phe Cys Glu
        930                 935                 940

Glu Asp Ile Asn Glu Cys Ala Ser Asp Pro Cys Arg Asn Gly Ala Asn
945                 950                 955                 960
```

```
Cys Thr Asp Cys Val Asp Ser Tyr Thr Cys Thr Cys Pro Ala Gly Phe
            965                 970                 975

Ser Gly Ile His Cys Glu Asn Asn Thr Pro Asp Cys Thr Glu Ser Ser
            980                 985                 990

Cys Phe Asn Gly Gly Thr Cys Val  Asp Gly Ile Asn Ser  Phe Thr Cys
        995             1000                1005

Leu Cys Pro Pro Gly Phe Thr  Gly Ser Tyr Cys Gln  His Val Val
    1010            1015            1020

Asn Glu  Cys Asp Ser Arg Pro  Cys Leu Leu Gly Gly  Thr Cys Gln
    1025            1030            1035

Asp Gly  Arg Gly Leu His Arg  Cys Thr Cys Pro Gln  Gly Tyr Thr
    1040            1045            1050

Gly Pro  Asn Cys Gln Asn Leu  Val His Trp Cys Asp  Ser Ser Pro
    1055            1060            1065

Cys Lys  Asn Gly Gly Lys Cys  Trp Gln Thr His Thr  Gln Tyr Arg
    1070            1075            1080

Cys Glu  Cys Pro Ser Gly Trp  Thr Gly Leu Tyr Cys  Asp Val Pro
    1085            1090            1095

Ser Val  Ser Cys Glu Val Ala  Ala Gln Arg Gln Gly  Val Asp Val
    1100            1105            1110

Ala Arg  Leu Cys Gln His Gly  Gly Leu Cys Val Asp  Ala Gly Asn
    1115            1120            1125

Thr His  His Cys Arg Cys Gln  Ala Gly Tyr Thr Gly  Ser Tyr Cys
    1130            1135            1140

Glu Asp  Leu Val Asp Glu Cys  Ser Pro Ser Pro Cys  Gln Asn Gly
    1145            1150            1155

Ala Thr  Cys Thr Asp Tyr Leu  Gly Gly Tyr Ser Cys  Lys Cys Val
    1160            1165            1170

Ala Gly  Tyr His Gly Val Asn  Cys Ser Glu Glu Ile  Asp Glu Cys
    1175            1180            1185

Leu Ser  His Pro Cys Gln Asn  Gly Gly Thr Cys Leu  Asp Leu Pro
    1190            1195            1200

Asn Thr  Tyr Lys Cys Ser Cys  Pro Arg Gly Thr Gln  Gly Val His
    1205            1210            1215

Cys Glu  Ile Asn Val Asp Asp  Cys Asn Pro Pro Val  Asp Pro Val
    1220            1225            1230

Ser Arg  Ser Pro Lys Cys Phe  Asn Asn Gly Thr Cys  Val Asp Gln
    1235            1240            1245

Val Gly  Gly Tyr Ser Cys Thr  Cys Pro Pro Gly Phe  Val Gly Glu
    1250            1255            1260

Arg Cys  Glu Gly Asp Val Asn  Glu Cys Leu Ser Asn  Pro Cys Asp
    1265            1270            1275

Ala Arg  Gly Thr Gln Asn Cys  Val Gln Arg Val Asn  Asp Phe His
    1280            1285            1290

Cys Glu  Cys Arg Ala Gly His  Thr Gly Arg Arg Cys  Glu Ser Val
    1295            1300            1305

Ile Asn  Gly Cys Lys Gly Lys  Pro Cys Lys Asn Gly  Gly Thr Cys
    1310            1315            1320

Ala Val  Ala Ser Asn Thr Ala  Arg Gly Phe Ile Cys  Lys Cys Pro
    1325            1330            1335

Ala Gly  Phe Glu Gly Ala Thr  Cys Glu Asn Asp Ala  Arg Thr Cys
    1340            1345            1350
```

```
Gly Ser Leu Arg Cys Leu Asn Gly Gly Thr Cys Ile Ser Gly Pro
    1355             1360             1365

Arg Ser Pro Thr Cys Leu Cys Leu Gly Pro Phe Thr Gly Pro Glu
    1370             1375             1380

Cys Gln Phe Pro Ala Ser Ser Pro Cys Leu Gly Gly Asn Pro Cys
    1385             1390             1395

Tyr Asn Gln Gly Thr Cys Glu Pro Thr Ser Glu Ser Pro Phe Tyr
    1400             1405             1410

Arg Cys Leu Cys Pro Ala Lys Phe Asn Gly Leu Leu Cys His Ile
    1415             1420             1425

Leu Asp Tyr Ser Phe Gly Gly Gly Ala Gly Arg Asp Ile Pro Pro
    1430             1435             1440

Pro Leu Ile Glu Glu Ala Cys Glu Leu Pro Glu Cys Gln Glu Asp
    1445             1450             1455

Ala Gly Asn Lys Val Cys Ser Leu Gln Cys Asn Asn His Ala Cys
    1460             1465             1470

Gly Trp Asp Gly Gly Asp Cys Ser Leu Asn Phe Asn Asp Pro Trp
    1475             1480             1485

Lys Asn Cys Thr Gln Ser Leu Gln Cys Trp Lys Tyr Phe Ser Asp
    1490             1495             1500

Gly His Cys Asp Ser Gln Cys Asn Ser Ala Gly Cys Leu Phe Asp
    1505             1510             1515

Gly Phe Asp Cys Gln Arg Ala Glu Gly Gln Cys Asn Pro Leu Tyr
    1520             1525             1530

Asp Gln Tyr Cys Lys Asp His Phe Ser Asp Gly His Cys Asp Gln
    1535             1540             1545

Gly Cys Asn Ser Ala Glu Cys Glu Trp Asp Gly Leu Asp Cys Ala
    1550             1555             1560

Glu His Val Pro Glu Arg Leu Ala Ala Gly Thr Leu Val Val Val
    1565             1570             1575

Val Leu Met Pro Pro Glu Gln Leu Arg Asn Ser Ser Phe His Phe
    1580             1585             1590

Leu Arg Glu Leu Ser Arg Val Leu His Thr Asn Val Val Phe Lys
    1595             1600             1605

Arg Asp Ala His Gly Gln Gln Met Ile Phe Pro Tyr Tyr Gly Arg
    1610             1615             1620

Glu Glu Glu Leu Arg Lys His Pro Ile Lys Arg Ala Ala Glu Gly
    1625             1630             1635

Trp Ala Ala Pro Asp Ala Leu Leu Gly Gln Val Lys Ala Ser Leu
    1640             1645             1650

Leu Pro Gly Gly Ser Glu Gly Gly Arg Arg Arg Glu Leu Asp
    1655             1660             1665

Pro Met Asp Val Arg Gly Ser Ile Val Tyr Leu Glu Ile Asp Asn
    1670             1675             1680

Arg Gln Cys Val Gln Ala Ser Ser Gln Cys Phe Gln Ser Ala Thr
    1685             1690             1695

Asp Val Ala Ala Phe Leu Gly Ala Leu Ala Ser Leu Gly Ser Leu
    1700             1705             1710

Asn Ile Pro Tyr Lys Ile Glu Ala Val Gln Ser Glu Thr Val Glu
    1715             1720             1725

Pro Pro Pro Pro Ala Gln Leu His Phe Met Tyr Val Ala Ala Ala
    1730             1735             1740

Ala Phe Val Leu Leu Phe Phe Val Gly Cys Gly Val Leu Leu Ser
```

```
          1745                1750                1755

Arg Lys  Arg Arg Arg Gln His  Gly Gln Leu Trp Phe  Pro Glu Gly
    1760                1765                1770

Phe Lys  Val Ser Glu Ala Ser  Lys Lys Lys Arg Arg  Glu Pro Leu
    1775                1780                1785

Gly Glu  Asp Ser Val Gly Leu  Lys Pro Leu Lys Asn  Ala Ser Asp
    1790                1795                1800

Gly Ala  Leu Met Asp Asp Asn  Gln Asn Glu Trp Gly  Asp Glu Asp
    1805                1810                1815

Leu Glu  Thr Lys Lys Phe Arg  Phe Glu Glu Pro Val  Val Leu Pro
    1820                1825                1830

Asp Leu  Asp Asp Gln Thr Asp  His Arg Gln Trp Thr  Gln Gln His
    1835                1840                1845

Leu Asp  Ala Ala Asp Leu Arg  Met Ser Ala Met Ala  Pro Thr Pro
    1850                1855                1860

Pro Gln  Gly Glu Val Asp Ala  Asp Cys Met Asp Val  Asn Val Arg
    1865                1870                1875

Gly Pro  Asp Gly Phe Thr Pro  Leu Met Ile Ala Ser  Cys Ser Gly
    1880                1885                1890

Gly Gly  Leu Glu Thr Gly Asn  Ser Glu Glu Glu Glu  Asp Ala Pro
    1895                1900                1905

Ala Val  Ile Ser Asp Phe Ile  Tyr Gln Gly Ala Ser  Leu His Asn
    1910                1915                1920

Gln Thr  Asp Arg Thr Gly Glu  Thr Ala Leu His Leu  Ala Ala Arg
    1925                1930                1935

Tyr Ser  Arg Ser Asp Ala Ala  Lys Arg Leu Leu Glu  Ala Ser Ala
    1940                1945                1950

Asp Ala  Asn Ile Gln Asp Asn  Met Gly Arg Thr Pro  Leu His Ala
    1955                1960                1965

Ala Val  Ser Ala Asp Ala Gln  Gly Val Phe Gln Ile  Leu Ile Arg
    1970                1975                1980

Asn Arg  Ala Thr Asp Leu Asp  Ala Arg Met His Asp  Gly Thr Thr
    1985                1990                1995

Pro Leu  Ile Leu Ala Ala Arg  Leu Ala Val Glu Gly  Met Leu Glu
    2000                2005                2010

Asp Leu  Ile Asn Ser His Ala  Asp Val Asn Ala Val  Asp Asp Leu
    2015                2020                2025

Gly Lys  Ser Ala Leu His Trp  Ala Ala Ala Val Asn  Asn Val Asp
    2030                2035                2040

Ala Ala  Val Val Leu Leu Lys  Asn Gly Ala Asn Lys  Asp Met Gln
    2045                2050                2055

Asn Asn  Arg Glu Glu Thr Pro  Leu Phe Leu Ala Ala  Arg Glu Gly
    2060                2065                2070

Ser Tyr  Glu Thr Ala Lys Val  Leu Leu Asp His Phe  Ala Asn Arg
    2075                2080                2085

Asp Ile  Thr Asp His Met Asp  Arg Leu Pro Arg Asp  Ile Ala Gln
    2090                2095                2100

Glu Arg  Met His His Asp Ile  Val Arg Leu Leu Asp  Glu Tyr Asn
    2105                2110                2115

Leu Val  Arg Ser Pro Gln Leu  His Gly Ala Pro Leu  Gly Gly Thr
    2120                2125                2130

Pro Thr  Leu Ser Pro Pro Leu  Cys Ser Pro Asn Gly  Tyr Leu Gly
    2135                2140                2145
```

-continued

```
Ser Leu Lys Pro Gly Val Gln  Gly Lys Lys Val Arg  Lys Pro Ser
    2150             2155              2160

Ser Lys Gly Leu Ala Cys Gly  Ser Lys Glu Ala Lys  Asp Leu Lys
    2165             2170              2175

Ala Arg Arg Lys Lys Ser Gln  Asp Gly Lys Gly Cys  Leu Leu Asp
    2180             2185              2190

Ser Ser Gly Met Leu Ser Pro  Val Asp Ser Leu Glu  Ser Pro His
    2195             2200              2205

Gly Tyr Leu Ser Asp Val Ala  Ser Pro Pro Leu Leu  Pro Ser Pro
    2210             2215              2220

Phe Gln Gln Ser Pro Ser Val  Pro Leu Asn His Leu  Pro Gly Met
    2225             2230              2235

Pro Asp Thr His Leu Gly Ile  Gly His Leu Asn Val  Ala Ala Lys
    2240             2245              2250

Pro Glu Met Ala Ala Leu Gly  Gly Gly Gly Arg Leu  Ala Phe Glu
    2255             2260              2265

Thr Gly Pro Pro Arg Leu Ser  His Leu Pro Val Ala  Ser Gly Thr
    2270             2275              2280

Ser Thr Val Leu Gly Ser Ser  Ser Gly Gly Ala Leu  Asn Phe Thr
    2285             2290              2295

Val Gly Gly Ser Thr Ser Leu  Asn Gly Gln Cys Glu  Trp Leu Ser
    2300             2305              2310

Arg Leu Gln Ser Gly Met Val  Pro Asn Gln Tyr Asn  Pro Leu Arg
    2315             2320              2325

Gly Ser Val Ala Pro Gly Pro  Leu Ser Thr Gln Ala  Pro Ser Leu
    2330             2335              2340

Gln His Gly Met Val Gly Pro  Leu His Ser Ser Leu  Ala Ala Ser
    2345             2350              2355

Ala Leu Ser Gln Met Met Ser  Tyr Gln Gly Leu Pro  Ser Thr Arg
    2360             2365              2370

Leu Ala Thr Gln Pro His Leu  Val Gln Thr Gln Gln  Val Gln Pro
    2375             2380              2385

Gln Asn Leu Gln Met Gln Gln  Gln Asn Leu Gln Pro  Ala Asn Ile
    2390             2395              2400

Gln Gln Gln Gln Ser Leu Gln  Pro Pro Pro Pro Pro  Pro Gln Pro
    2405             2410              2415

His Leu Gly Val Ser Ser Ala  Ala Ser Gly His Leu  Gly Arg Ser
    2420             2425              2430

Phe Leu Ser Gly Glu Pro Ser  Gln Ala Asp Val Gln  Pro Leu Gly
    2435             2440              2445

Pro Ser Ser Leu Ala Val His  Thr Ile Leu Pro Gln  Glu Ser Pro
    2450             2455              2460

Ala Leu Pro Thr Ser Leu Pro  Ser Ser Leu Val Pro  Pro Val Thr
    2465             2470              2475

Ala Ala Gln Phe Leu Thr Pro  Pro Ser Gln His Ser  Tyr Ser Ser
    2480             2485              2490

Pro Val Asp Asn Thr Pro Ser  His Gln Leu Gln Val  Pro Glu His
    2495             2500              2505

Pro Phe Leu Thr Pro Ser Pro  Glu Ser Pro Asp Gln  Trp Ser Ser
    2510             2515              2520

Ser Ser Pro His Ser Asn Val  Ser Asp Trp Ser Glu  Gly Val Ser
    2525             2530              2535
```

```
Ser Pro  Pro Thr Ser Met Gln  Ser Gln Ile Ala Arg  Ile Pro Glu
   2540                2545               2550

Ala Phe  Lys
   2555

<210> SEQ ID NO 26
<211> LENGTH: 205
<212> TYPE: PRT
<213> ORGANISM: Homo sapiens

<400> SEQUENCE: 26

Met Thr Pro Pro Glu Arg Leu Phe Leu Pro Arg Val Arg Gly Thr Thr
1               5                   10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
            35                  40                  45

Arg Gln Pro Pro Lys Met His Leu Ala His Ser Thr Leu Lys Pro Ala
    50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
            115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
            195                 200                 205

<210> SEQ ID NO 27
<211> LENGTH: 244
<212> TYPE: PRT
<213> ORGANISM: Homo sapiens

<400> SEQUENCE: 27

Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
            35                  40                  45

Gln Asp Gln Gly Gly Leu Val Thr Glu Thr Ala Asp Pro Gly Ala Gln
    50                  55                  60

Ala Gln Gln Gly Leu Gly Phe Gln Lys Leu Pro Glu Glu Glu Pro Glu
65                  70                  75                  80

Thr Asp Leu Ser Pro Gly Leu Pro Ala Ala His Leu Ile Gly Ala Pro
                85                  90                  95
```

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
    130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
            195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly

<210> SEQ ID NO 28
<211> LENGTH: 1427
<212> TYPE: PRT
<213> ORGANISM: Homo sapiens

<400> SEQUENCE: 28

Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
            20                  25                  30

Phe Gln Gln Ser Cys Leu Gln Ala Leu Glu Pro Gln Ala Val Ser Ser
        35                  40                  45

Tyr Leu Ser Pro Gly Ala Pro Leu Lys Gly Arg Pro Pro Ser Pro Gly
    50                  55                  60

Phe Gln Arg Gln Arg Gln Arg Gln Arg Ala Ala Gly Gly Ile Leu
65                  70                  75                  80

His Leu Glu Leu Leu Val Ala Val Gly Pro Asp Val Phe Gln Ala His
            85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
                165                 170                 175

Tyr Ile Thr Arg Phe Asp Leu Glu Leu Pro Asp Gly Asn Arg Gln Val
            180                 185                 190

Arg Gly Val Thr Gln Leu Gly Gly Ala Cys Ser Pro Thr Trp Ser Cys
            195                 200                 205

Leu Ile Thr Glu Asp Thr Gly Phe Asp Leu Gly Val Thr Ile Ala His
    210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
                245                 250                 255

Arg Ala Gly Leu Ala Trp Ser Pro Cys Ser Arg Arg Gln Leu Leu Ser
                260                 265                 270

Leu Leu Ser Ala Gly Arg Ala Arg Cys Val Trp Asp Pro Pro Arg Pro
                275                 280                 285

Gln Pro Gly Ser Ala Gly His Pro Pro Asp Ala Gln Pro Gly Leu Tyr
                290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
                325                 330                 335

Cys His Thr Asp Pro Leu Asp Gln Ser Ser Cys Ser Arg Leu Leu Val
                340                 345                 350

Pro Leu Leu Asp Gly Thr Glu Cys Gly Val Glu Lys Trp Cys Ser Lys
                355                 360                 365

Gly Arg Cys Arg Ser Leu Val Glu Leu Thr Pro Ile Ala Ala Val His
                370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Arg Gln Cys Asn Asn Pro Arg Pro
                405                 410                 415

Ala Phe Gly Gly Arg Ala Cys Val Gly Ala Asp Leu Gln Ala Glu Met
                420                 425                 430

Cys Asn Thr Gln Ala Cys Glu Lys Thr Gln Leu Glu Phe Met Ser Gln
                435                 440                 445

Gln Cys Ala Arg Thr Asp Gly Gln Pro Leu Arg Ser Ser Pro Gly Gly
                450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
                485                 490                 495

Lys Arg Gly Asp Ser Phe Leu Asp Gly Thr Arg Cys Met Pro Ser Gly
                500                 505                 510

Pro Arg Glu Asp Gly Thr Leu Ser Leu Cys Val Ser Gly Ser Cys Arg
                515                 520                 525

Thr Phe Gly Cys Asp Gly Arg Met Asp Ser Gln Gln Val Trp Asp Arg
                530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
                580                 585                 590

Thr His Leu Ala Val Arg Ile Gly Gly Arg Tyr Val Val Ala Gly Lys
                595                 600                 605

Met Ser Ile Ser Pro Asn Thr Thr Tyr Pro Ser Leu Leu Glu Asp Gly
                610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln

```
                        645                 650                 655

Val Tyr Arg Arg Tyr Gly Glu Glu Tyr Gly Asn Leu Thr Arg Pro Asp
                660                 665                 670

Ile Thr Phe Thr Tyr Phe Gln Pro Lys Pro Arg Gln Ala Trp Val Trp
            675                 680                 685

Ala Ala Val Arg Gly Pro Cys Ser Val Ser Cys Gly Ala Gly Leu Arg
        690                 695                 700

Trp Val Asn Tyr Ser Cys Leu Asp Gln Ala Arg Lys Glu Leu Val Glu
705                 710                 715                 720

Thr Val Gln Cys Gln Gly Ser Gln Gln Pro Pro Ala Trp Pro Glu Ala
                725                 730                 735

Cys Val Leu Glu Pro Cys Pro Pro Tyr Trp Ala Val Gly Asp Phe Gly
            740                 745                 750

Pro Cys Ser Ala Ser Cys Gly Gly Gly Leu Arg Glu Arg Pro Val Arg
            755                 760                 765

Cys Val Glu Ala Gln Gly Ser Leu Leu Lys Thr Leu Pro Pro Ala Arg
        770                 775                 780

Cys Arg Ala Gly Ala Gln Gln Pro Ala Val Ala Leu Glu Thr Cys Asn
785                 790                 795                 800

Pro Gln Pro Cys Pro Ala Arg Trp Glu Val Ser Glu Pro Ser Ser Cys
            805                 810                 815

Thr Ser Ala Gly Gly Ala Gly Leu Ala Leu Glu Asn Glu Thr Cys Val
            820                 825                 830

Pro Gly Ala Asp Gly Leu Glu Ala Pro Val Thr Glu Gly Pro Gly Ser
            835                 840                 845

Val Asp Glu Lys Leu Pro Ala Pro Glu Pro Cys Val Gly Met Ser Cys
        850                 855                 860

Pro Pro Gly Trp Gly His Leu Asp Ala Thr Ser Ala Gly Glu Lys Ala
865                 870                 875                 880

Pro Ser Pro Trp Gly Ser Ile Arg Thr Gly Ala Gln Ala Ala His Val
            885                 890                 895

Trp Thr Pro Ala Ala Gly Ser Cys Ser Val Ser Cys Gly Arg Gly Leu
            900                 905                 910

Met Glu Leu Arg Phe Leu Cys Met Asp Ser Ala Leu Arg Val Pro Val
            915                 920                 925

Gln Glu Glu Leu Cys Gly Leu Ala Ser Lys Pro Gly Ser Arg Arg Glu
        930                 935                 940

Val Cys Gln Ala Val Pro Cys Pro Ala Arg Trp Gln Tyr Lys Leu Ala
945                 950                 955                 960

Ala Cys Ser Val Ser Cys Gly Arg Gly Val Val Arg Arg Ile Leu Tyr
            965                 970                 975

Cys Ala Arg Ala His Gly Glu Asp Asp Gly Glu Glu Ile Leu Leu Asp
            980                 985                 990

Thr Gln Cys Gln Gly Leu Pro Arg  Pro Glu Pro Gln Glu  Ala Cys Ser
            995                 1000                1005

Leu Glu  Pro Cys Pro Pro Arg  Trp Lys Val Met Ser  Leu Gly Pro
    1010                1015                1020

Cys Ser  Ala Ser Cys Gly Leu  Gly Thr Ala Arg Arg  Ser Val Ala
    1025                1030                1035

Cys Val  Gln Leu Asp Gln Gly  Gln Asp Val Glu Val  Asp Glu Ala
    1040                1045                1050

Ala Cys  Ala Ala Leu Val Arg  Pro Glu Ala Ser Val  Pro Cys Leu
    1055                1060                1065
```

-continued

```
Ile Ala Asp Cys Thr Tyr Arg Trp His Val Gly Thr Trp Met Glu
    1070            1075            1080

Cys Ser Val Ser Cys Gly Asp Gly Ile Gln Arg Arg Arg Asp Thr
    1085            1090            1095

Cys Leu Gly Pro Gln Ala Gln Ala Pro Val Pro Ala Asp Phe Cys
    1100            1105            1110

Gln His Leu Pro Lys Pro Val Thr Val Arg Gly Cys Trp Ala Gly
    1115            1120            1125

Pro Cys Val Gly Gln Gly Thr Pro Ser Leu Val Pro His Glu Glu
    1130            1135            1140

Ala Ala Ala Pro Gly Arg Thr Thr Ala Thr Pro Ala Gly Ala Ser
    1145            1150            1155

Leu Glu Trp Ser Gln Ala Arg Gly Leu Leu Phe Ser Pro Ala Pro
    1160            1165            1170

Gln Pro Arg Arg Leu Leu Pro Gly Pro Gln Glu Asn Ser Val Gln
    1175            1180            1185

Ser Ser Ala Cys Gly Arg Gln His Leu Glu Pro Thr Gly Thr Ile
    1190            1195            1200

Asp Met Arg Gly Pro Gly Gln Ala Asp Cys Ala Val Ala Ile Gly
    1205            1210            1215

Arg Pro Leu Gly Glu Val Val Thr Leu Arg Val Leu Glu Ser Ser
    1220            1225            1230

Leu Asn Cys Ser Ala Gly Asp Met Leu Leu Leu Trp Gly Arg Leu
    1235            1240            1245

Thr Trp Arg Lys Met Cys Arg Lys Leu Leu Asp Met Thr Phe Ser
    1250            1255            1260

Ser Lys Thr Asn Thr Leu Val Val Arg Gln Arg Cys Gly Arg Pro
    1265            1270            1275

Gly Gly Gly Val Leu Leu Arg Tyr Gly Ser Gln Leu Ala Pro Glu
    1280            1285            1290

Thr Phe Tyr Arg Glu Cys Asp Met Gln Leu Phe Gly Pro Trp Gly
    1295            1300            1305

Glu Ile Val Ser Pro Ser Leu Ser Pro Ala Thr Ser Asn Ala Gly
    1310            1315            1320

Gly Cys Arg Leu Phe Ile Asn Val Ala Pro His Ala Arg Ile Ala
    1325            1330            1335

Ile His Ala Leu Ala Thr Asn Met Gly Ala Gly Thr Glu Gly Ala
    1340            1345            1350

Asn Ala Ser Tyr Ile Leu Ile Arg Asp Thr His Ser Leu Arg Thr
    1355            1360            1365

Thr Ala Phe His Gly Gln Gln Val Leu Tyr Trp Glu Ser Glu Ser
    1370            1375            1380

Ser Gln Ala Glu Met Glu Phe Ser Glu Gly Phe Leu Lys Ala Gln
    1385            1390            1395

Ala Ser Leu Arg Gly Gln Tyr Trp Thr Leu Gln Ser Trp Val Pro
    1400            1405            1410

Glu Met Gln Asp Pro Gln Ser Trp Lys Gly Lys Glu Gly Thr
    1415            1420            1425
```

<210> SEQ ID NO 29
<211> LENGTH: 450
<212> TYPE: PRT
<213> ORGANISM: Homo sapiens -continued

```
<400> SEQUENCE: 29

Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Phe Trp Pro
                20                  25                  30

Thr Leu Ala Phe Leu Leu Cys Ser Phe Pro Ala Ala Thr Ser Pro Cys
            35                  40                  45

Lys Ile Leu Lys Cys Asn Ser Glu Phe Trp Ser Ala Thr Ser Gly Ser
        50                  55                  60

His Ala Pro Ala Ser Asp Asp Thr Pro Glu Phe Cys Ala Ala Leu Arg
65                  70                  75                  80

Ser Tyr Ala Leu Cys Thr Arg Arg Thr Ala Arg Thr Cys Arg Gly Asp
                85                  90                  95

Leu Ala Tyr His Ser Ala Val His Gly Ile Glu Asp Leu Met Ser Gln
            100                 105                 110

His Asn Cys Ser Lys Asp Gly Pro Thr Ser Gln Pro Arg Leu Arg Thr
        115                 120                 125

Leu Pro Pro Ala Gly Asp Ser Gln Glu Arg Ser Asp Ser Pro Glu Ile
        130                 135                 140

Cys His Tyr Glu Lys Ser Phe His Lys His Ser Ala Thr Pro Asn Tyr
145                 150                 155                 160

Thr His Cys Gly Leu Phe Gly Asp Pro His Leu Arg Thr Phe Thr Asp
                165                 170                 175

Arg Phe Gln Thr Cys Lys Val Gln Gly Ala Trp Pro Leu Ile Asp Asn
                180                 185                 190

Asn Tyr Leu Asn Val Gln Val Thr Asn Thr Pro Val Leu Pro Gly Ser
            195                 200                 205

Ala Ala Thr Ala Thr Ser Lys Leu Thr Ile Ile Phe Lys Asn Phe Gln
        210                 215                 220

Glu Cys Val Asp Gln Lys Val Tyr Gln Ala Glu Met Asp Glu Leu Pro
225                 230                 235                 240

Ala Ala Phe Val Asp Gly Ser Lys Asn Gly Gly Asp Lys His Gly Ala
                245                 250                 255

Asn Ser Leu Lys Ile Thr Glu Lys Val Ser Gly Gln His Val Glu Ile
            260                 265                 270

Gln Ala Lys Tyr Ile Gly Thr Thr Ile Val Val Arg Gln Val Gly Arg
        275                 280                 285

Tyr Leu Thr Phe Ala Val Arg Met Pro Glu Glu Val Val Asn Ala Val
    290                 295                 300

Glu Asp Trp Asp Ser Gln Gly Leu Tyr Leu Cys Leu Arg Gly Cys Pro
305                 310                 315                 320

Leu Asn Gln Gln Ile Asp Phe Gln Ala Phe His Thr Asn Ala Glu Gly
                325                 330                 335

Thr Gly Ala Arg Arg Leu Ala Ala Ala Ser Pro Ala Pro Thr Ala Pro
            340                 345                 350

Glu Thr Phe Pro Tyr Glu Thr Ala Val Ala Lys Cys Lys Glu Lys Leu
            355                 360                 365

Pro Val Glu Asp Leu Tyr Tyr Gln Ala Cys Val Phe Asp Leu Leu Thr
    370                 375                 380

Thr Gly Asp Val Asn Phe Thr Leu Ala Ala Tyr Tyr Ala Leu Glu Asp
385                 390                 395                 400

Val Lys Met Leu His Ser Asn Lys Asp Lys Leu His Leu Tyr Glu Arg
                405                 410                 415
```

-continued

```
Thr Arg Asp Leu Pro Gly Arg Ala Ala Ala Gly Leu Pro Leu Ala Pro
        420                 425                 430

Arg Pro Leu Leu Gly Ala Leu Val Pro Leu Leu Ala Leu Leu Pro Val
        435                 440                 445

Phe Cys
    450

<210> SEQ ID NO 30
<211> LENGTH: 464
<212> TYPE: PRT
<213> ORGANISM: Homo sapiens

<400> SEQUENCE: 30

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
        20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
        100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
        290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
```

```
                    325                 330                 335
Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
            355                 360                 365

Asp Met Gly Leu Val Asp Leu Phe Ser Pro Glu Lys Ser Lys Leu Pro
            370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                    405                 410                 415

Ser Thr Ala Val Val Ile Ala Gly Arg Ser Leu Asn Pro Asn Arg Val
            420                 425                 430

Thr Phe Lys Ala Asn Arg Leu Phe Leu Val Phe Ile Arg Glu Val Pro
            435                 440                 445

Leu Asn Thr Ile Ile Phe Met Gly Arg Val Ala Asn Pro Cys Val Lys
            450                 455                 460

<210> SEQ ID NO 31
<211> LENGTH: 967
<212> TYPE: PRT
<213> ORGANISM: Homo sapiens

<400> SEQUENCE: 31

Met Gln Arg Ala Val Pro Glu Gly Phe Gly Arg Arg Lys Leu Gly Ser
1                   5                   10                  15

Asp Met Gly Asn Ala Glu Arg Ala Pro Gly Ser Arg Ser Phe Gly Pro
                    20                  25                  30

Val Pro Thr Leu Leu Leu Leu Ala Ala Ala Leu Leu Ala Val Ser Asp
            35                  40                  45

Ala Leu Gly Arg Pro Ser Glu Glu Asp Glu Glu Leu Val Val Pro Glu
            50                  55                  60

Leu Glu Arg Ala Pro Gly His Gly Thr Thr Arg Leu Arg Leu His Ala
65                  70                  75                  80

Phe Asp Gln Gln Leu Asp Leu Glu Leu Arg Pro Asp Ser Ser Phe Leu
                    85                  90                  95

Ala Pro Gly Phe Thr Leu Gln Asn Val Gly Arg Lys Ser Gly Ser Glu
            100                 105                 110

Thr Pro Leu Pro Glu Thr Asp Leu Ala His Cys Phe Tyr Ser Gly Thr
            115                 120                 125

Val Asn Gly Asp Pro Ser Ser Ala Ala Ala Leu Ser Leu Cys Glu Gly
            130                 135                 140

Val Arg Gly Ala Phe Tyr Leu Leu Gly Glu Ala Tyr Phe Ile Gln Pro
145                 150                 155                 160

Leu Pro Ala Ala Ser Glu Arg Leu Ala Thr Ala Ala Pro Gly Glu Lys
                    165                 170                 175

Pro Pro Ala Pro Leu Gln Phe His Leu Leu Arg Arg Asn Arg Gln Gly
            180                 185                 190

Asp Val Gly Gly Thr Cys Gly Val Val Asp Asp Glu Pro Arg Pro Thr
            195                 200                 205

Gly Lys Ala Glu Thr Glu Asp Glu Asp Glu Gly Thr Glu Gly Glu Asp
            210                 215                 220

Glu Gly Pro Gln Trp Ser Pro Gln Asp Pro Ala Leu Gln Gly Val Gly
225                 230                 235                 240
```

```
Gln Pro Thr Gly Thr Gly Ser Ile Arg Lys Lys Arg Phe Val Ser Ser
            245             250             255

His Arg Tyr Val Glu Thr Met Leu Val Ala Asp Gln Ser Met Ala Glu
            260             265             270

Phe His Gly Ser Gly Leu Lys His Tyr Leu Leu Thr Leu Phe Ser Val
            275             280             285

Ala Ala Arg Leu Tyr Lys His Pro Ser Ile Arg Asn Ser Val Ser Leu
        290             295             300

Val Val Val Lys Ile Leu Val Ile His Asp Glu Gln Lys Gly Pro Glu
305             310             315             320

Val Thr Ser Asn Ala Ala Leu Thr Leu Arg Asn Phe Cys Asn Trp Gln
            325             330             335

Lys Gln His Asn Pro Pro Ser Asp Arg Asp Ala Glu His Tyr Asp Thr
            340             345             350

Ala Ile Leu Phe Thr Arg Gln Asp Leu Cys Gly Ser Gln Thr Cys Asp
            355             360             365

Thr Leu Gly Met Ala Asp Val Gly Thr Val Cys Asp Pro Ser Arg Ser
        370             375             380

Cys Ser Val Ile Glu Asp Asp Gly Leu Gln Ala Ala Phe Thr Thr Ala
385             390             395             400

His Glu Leu Gly His Val Phe Asn Met Pro His Asp Asp Ala Lys Gln
            405             410             415

Cys Ala Ser Leu Asn Gly Val Asn Gln Asp Ser His Met Met Ala Ser
            420             425             430

Met Leu Ser Asn Leu Asp His Ser Gln Pro Trp Ser Pro Cys Ser Ala
            435             440             445

Tyr Met Ile Thr Ser Phe Leu Asp Asn Gly His Gly Glu Cys Leu Met
        450             455             460

Asp Lys Pro Gln Asn Pro Ile Gln Leu Pro Gly Asp Leu Pro Gly Thr
465             470             475             480

Ser Tyr Asp Ala Asn Arg Gln Cys Gln Phe Thr Phe Gly Glu Asp Ser
            485             490             495

Lys His Cys Pro Asp Ala Ala Ser Thr Cys Ser Thr Leu Trp Cys Thr
            500             505             510

Gly Thr Ser Gly Gly Val Leu Val Cys Gln Thr Lys His Phe Pro Trp
            515             520             525

Ala Asp Gly Thr Ser Cys Gly Glu Gly Lys Trp Cys Ile Asn Gly Lys
        530             535             540

Cys Val Asn Lys Thr Asp Arg Lys His Phe Asp Thr Pro Phe His Gly
545             550             555             560

Ser Trp Gly Met Trp Gly Pro Trp Gly Asp Cys Ser Arg Thr Cys Gly
            565             570             575

Gly Gly Val Gln Tyr Thr Met Arg Glu Cys Asp Asn Pro Val Pro Lys
            580             585             590

Asn Gly Gly Lys Tyr Cys Glu Gly Lys Arg Val Arg Tyr Arg Ser Cys
            595             600             605

Asn Leu Glu Asp Cys Pro Asp Asn Asn Gly Lys Thr Phe Arg Glu Glu
        610             615             620

Gln Cys Glu Ala His Asn Glu Phe Ser Lys Ala Ser Phe Gly Ser Gly
625             630             635             640

Pro Ala Val Glu Trp Ile Pro Lys Tyr Ala Gly Val Ser Pro Lys Asp
            645             650             655

Arg Cys Lys Leu Ile Cys Gln Ala Lys Gly Ile Gly Tyr Phe Phe Val
```

```
                 660                 665                 670

Leu Gln Pro Lys Val Val Asp Gly Thr Pro Cys Ser Thr Asp Ser Thr
        675                 680                 685

Ser Val Cys Val Gln Gly Gln Cys Val Lys Ala Gly Cys Asp Arg Ile
        690                 695                 700

Ile Asp Ser Lys Lys Lys Phe Asp Lys Cys Gly Val Cys Gly Gly Asn
705                 710                 715                 720

Gly Ser Thr Cys Lys Lys Ile Ser Gly Ser Val Thr Ser Ala Lys Pro
                725                 730                 735

Gly Tyr His Asp Ile Ile Thr Ile Pro Thr Gly Ala Thr Asn Ile Glu
                740                 745                 750

Val Lys Gln Arg Asn Gln Arg Gly Ser Arg Asn Asn Gly Ser Phe Leu
        755                 760                 765

Ala Ile Lys Ala Ala Asp Gly Thr Tyr Ile Leu Asn Gly Asp Tyr Thr
        770                 775                 780

Leu Ser Thr Leu Glu Gln Asp Ile Met Tyr Lys Gly Val Val Leu Arg
785                 790                 795                 800

Tyr Ser Gly Ser Ser Ala Ala Leu Glu Arg Ile Arg Ser Phe Ser Pro
                805                 810                 815

Leu Lys Glu Pro Leu Thr Ile Gln Val Leu Thr Val Gly Asn Ala Leu
                820                 825                 830

Arg Pro Lys Ile Lys Tyr Thr Tyr Phe Val Lys Lys Lys Glu Ser
                835                 840                 845

Phe Asn Ala Ile Pro Thr Phe Ser Ala Trp Val Ile Glu Glu Trp Gly
        850                 855                 860

Glu Cys Ser Lys Ser Cys Glu Leu Gly Trp Gln Arg Arg Leu Val Glu
865                 870                 875                 880

Cys Arg Asp Ile Asn Gly Gln Pro Ala Ser Glu Cys Ala Lys Glu Val
                885                 890                 895

Lys Pro Ala Ser Thr Arg Pro Cys Ala Asp His Pro Cys Pro Gln Trp
                900                 905                 910

Gln Leu Gly Glu Trp Ser Ser Cys Ser Lys Thr Cys Gly Lys Gly Tyr
        915                 920                 925

Lys Lys Arg Ser Leu Lys Cys Leu Ser His Asp Gly Gly Val Leu Ser
        930                 935                 940

His Glu Ser Cys Asp Pro Leu Lys Lys Pro Lys His Phe Ile Asp Phe
945                 950                 955                 960

Cys Thr Met Ala Glu Cys Ser
                965

<210> SEQ ID NO 32
<211> LENGTH: 402
<212> TYPE: PRT
<213> ORGANISM: Homo sapiens

<400> SEQUENCE: 32

Met Gln Met Ser Pro Ala Leu Thr Cys Leu Val Leu Gly Leu Ala Leu
1                 5                 10                 15

Val Phe Gly Glu Gly Ser Ala Val His His Pro Pro Ser Tyr Val Ala
                20                 25                 30

His Leu Ala Ser Asp Phe Gly Val Arg Val Phe Gln Gln Val Ala Gln
        35                 40                 45

Ala Ser Lys Asp Arg Asn Val Val Phe Ser Pro Tyr Gly Val Ala Ser
        50                 55                 60
```

-continued

```
Val Leu Ala Met Leu Gln Leu Thr Thr Gly Gly Glu Thr Gln Gln Gln
65              70              75              80

Ile Gln Ala Ala Met Gly Phe Lys Ile Asp Asp Lys Gly Met Ala Pro
                85              90              95

Ala Leu Arg His Leu Tyr Lys Glu Leu Met Gly Pro Trp Asn Lys Asp
            100             105             110

Glu Ile Ser Thr Thr Asp Ala Ile Phe Val Gln Arg Asp Leu Lys Leu
            115             120             125

Val Gln Gly Phe Met Pro His Phe Phe Arg Leu Phe Arg Ser Thr Val
            130             135             140

Lys Gln Val Asp Phe Ser Glu Val Glu Arg Ala Arg Phe Ile Ile Asn
145             150             155             160

Asp Trp Val Lys Thr His Thr Lys Gly Met Ile Ser Asn Leu Leu Gly
                165             170             175

Lys Gly Ala Val Asp Gln Leu Thr Arg Leu Val Leu Val Asn Ala Leu
            180             185             190

Tyr Phe Asn Gly Gln Trp Lys Thr Pro Phe Pro Asp Ser Ser Thr His
            195             200             205

Arg Arg Leu Phe His Lys Ser Asp Gly Ser Thr Val Ser Val Pro Met
    210             215             220

Met Ala Gln Thr Asn Lys Phe Asn Tyr Thr Glu Phe Thr Thr Pro Asp
225             230             235             240

Gly His Tyr Tyr Asp Ile Leu Glu Leu Pro Tyr His Gly Asp Thr Leu
                245             250             255

Ser Met Phe Ile Ala Ala Pro Tyr Glu Lys Glu Val Pro Leu Ser Ala
            260             265             270

Leu Thr Asn Ile Leu Ser Ala Gln Leu Ile Ser His Trp Lys Gly Asn
            275             280             285

Met Thr Arg Leu Pro Arg Leu Leu Val Leu Pro Lys Phe Ser Leu Glu
    290             295             300

Thr Glu Val Asp Leu Arg Lys Pro Leu Glu Asn Leu Gly Met Thr Asp
305             310             315             320

Met Phe Arg Gln Phe Gln Ala Asp Phe Thr Ser Leu Ser Asp Gln Glu
            325             330             335

Pro Leu His Val Ala Gln Ala Leu Gln Lys Val Lys Ile Glu Val Asn
            340             345             350

Glu Ser Gly Thr Val Ala Ser Ser Ser Thr Ala Val Ile Val Ser Ala
            355             360             365

Arg Met Ala Pro Glu Glu Ile Ile Met Asp Arg Pro Phe Leu Phe Val
    370             375             380

Val Arg His Asn Pro Thr Gly Thr Val Leu Phe Met Gly Gln Val Met
385             390             395             400

Glu Pro
```

<210> SEQ ID NO 33
<211> LENGTH: 211
<212> TYPE: PRT
<213> ORGANISM: Homo sapiens

<400> SEQUENCE: 33

```
Met Thr Pro Trp Leu Gly Leu Ile Val Leu Leu Gly Ser Trp Ser Leu
1               5               10              15

Gly Asp Trp Gly Ala Glu Ala Cys Thr Cys Ser Pro Ser His Pro Gln
        20              25              30
```

-continued

```
Asp Ala Phe Cys Asn Ser Asp Ile Val Ile Arg Ala Lys Val Val Gly
    35              40              45

Lys Lys Leu Val Lys Glu Gly Pro Phe Gly Thr Leu Val Tyr Thr Ile
    50              55              60

Lys Gln Met Lys Met Tyr Arg Gly Phe Thr Lys Met Pro His Val Gln
65              70              75              80

Tyr Ile His Thr Glu Ala Ser Glu Ser Leu Cys Gly Leu Lys Leu Glu
                85              90              95

Val Asn Lys Tyr Gln Tyr Leu Leu Thr Gly Arg Val Tyr Asp Gly Lys
                100             105             110

Met Tyr Thr Gly Leu Cys Asn Phe Val Glu Arg Trp Asp Gln Leu Thr
        115             120             125

Leu Ser Gln Arg Lys Gly Leu Asn Tyr Arg Tyr His Leu Gly Cys Asn
    130             135             140

Cys Lys Ile Lys Ser Cys Tyr Tyr Leu Pro Cys Phe Val Thr Ser Lys
145             150             155             160

Asn Glu Cys Leu Trp Thr Asp Met Leu Ser Asn Phe Gly Tyr Pro Gly
                165             170             175

Tyr Gln Ser Lys His Tyr Ala Cys Ile Arg Gln Lys Gly Gly Tyr Cys
                180             185             190

Ser Trp Tyr Arg Gly Trp Ala Pro Pro Asp Lys Ser Ile Ile Asn Ala
    195             200             205

Thr Asp Pro
    210

<210> SEQ ID NO 34
<211> LENGTH: 101
<212> TYPE: PRT
<213> ORGANISM: Homo sapiens

<400> SEQUENCE: 34

Met Ser Ser Ala Ala Gly Phe Cys Ala Ser Arg Pro Gly Leu Leu Phe
1               5               10              15

Leu Gly Leu Leu Leu Leu Pro Leu Val Val Ala Phe Ala Ser Ala Glu
                20              25              30

Ala Glu Glu Asp Gly Asp Leu Gln Cys Leu Cys Val Lys Thr Thr Ser
        35              40              45

Gln Val Arg Pro Arg His Ile Thr Ser Leu Glu Val Ile Lys Ala Gly
    50              55              60

Pro His Cys Pro Thr Ala Gln Leu Ile Ala Thr Leu Lys Asn Gly Arg
65              70              75              80

Lys Ile Cys Leu Asp Leu Gln Ala Pro Leu Tyr Lys Lys Ile Ile Lys
                85              90              95

Lys Leu Leu Glu Ser
                100
```